(12) United States Patent
McCray et al.

(10) Patent No.: US 8,846,578 B2
(45) Date of Patent: Sep. 30, 2014

(54) ZINC FINGER NUCLEASE FOR THE CFTR GENE AND METHODS OF USE THEREOF

(75) Inventors: Paul McCray, Iowa City, IA (US);
Morgan Maeder, Brookline, MA (US);
Jae Keith Joung, Winchester, MA (US)

(73) Assignees: The General Hospital Corporation, Boston, MA (US); University of Iowa Research Foundation, Iowa City, IA (US)

( * ) Notice: Subject to any disclaimer, the term of this patent is extended or adjusted under 35 U.S.C. 154(b) by 710 days.

(21) Appl. No.: 12/905,824

(22) Filed: Oct. 15, 2010

(65) Prior Publication Data
US 2011/0086015 A1     Apr. 14, 2011

Related U.S. Application Data

(63) Continuation-in-part of application No. PCT/US2009/040617, filed on Apr. 15, 2009.

(60) Provisional application No. 61/124,297, filed on Apr. 16, 2008.

(51) Int. Cl.
| | |
|---|---|
| *C40B 50/06* | (2006.01) |
| *C12N 9/22* | (2006.01) |
| *C07K 14/47* | (2006.01) |
| *C12N 15/10* | (2006.01) |
| *A61K 38/00* | (2006.01) |

(52) U.S. Cl.
CPC .............. *C12N 15/1082* (2013.01); *C12N 9/22* (2013.01); *C07K 14/4702* (2013.01); *A61K 38/00* (2013.01); *C07K 14/4703* (2013.01)
USPC .......................................................... 506/26

(58) Field of Classification Search
None
See application file for complete search history.

(56) References Cited

U.S. PATENT DOCUMENTS

| | | | |
|---|---|---|---|
| 5,436,150 A | 7/1995 | Chandrasegaran | 435/199 |
| 6,242,568 B1 | 6/2001 | Barbas, III et al. | 530/350 |
| 6,503,717 B2 | 1/2003 | Case et al. | 435/6 |
| 7,393,318 B2 | 7/2008 | Joung et al. | 506/17 |
| 2005/0208489 A1 | 9/2005 | Carroll et al. | 435/6 |
| 2005/0215502 A1 | 9/2005 | Cox et al. | 514/44 R |
| 2006/0153826 A1 | 7/2006 | Arnould et al. | 424/94.61 |

FOREIGN PATENT DOCUMENTS

| | | |
|---|---|---|
| WO | WO 03/087341 | 10/2003 |
| WO | WO 2007/014181 | 2/2007 |

OTHER PUBLICATIONS

Bae et al., "Human zinc fingers as building blocks in the construction of artificial transcription factors," *Nat. Biotechnol.*, 21:275-280, 2003.
Beerli and Barbas, "Engineering polydactyl zinc-finger transcription factors," *Nat. Biotechnol.*, 20:135-141, 2002.
Carroll et al., "Design, construction and in vitro testing of zinc finger nucleases," *Nature Protocols*, 1(3): 1329-1341, 2006.
Cornu et al., "DNA-binding specificity is a major determinant of the activity and toxicity of zinc-finger nucleases," *Mol. Ther.*, 16:352-358, 2008.
Durai et al., "Zinc finger nucleases: custom-designed molecular scissors for genome engineering of plant and mammalian cells," *Nucleic Acids Res.*, 33:5978-5990, 2005.

(Continued)

*Primary Examiner* — Christian Boesen
(74) *Attorney, Agent, or Firm* — Parker Highlander PLLC

(57) ABSTRACT

The present invention provides new zinc finger proteins and zinc finger nuclease (ZFNs) that find particular using in repairing the cystic fibrosis transmembrane conductance regulator (CFTR) gene.

15 Claims, 32 Drawing Sheets

TGTCA (introduces BspH1 site)
↓
ACTT████████TGATGA████████ adenovirus

The donor template is 1320 nucleotides long. 350 nts of left arm and 970 nts of right arm. It is packaged in an adenoviral vector but could be delivered by other vectors (viral or non-viral).

The nts highlighted green on the sequence is the region where the ZFNs bind. In between the two is a 6-nucleotide spacer. The TGTCA fragment is introduced between the spacer region TGATGA which will introduce the unique Bsph1-TCATGA only in the donor.

<u>Keith lab nomenclature for L1, R1</u>

L1 = SZS21-1
R1 = SZS96-5

(56) References Cited

OTHER PUBLICATIONS

Elrod-Erickson et al., "Zif268 protein-DNA complex refined at 1.6 Å: a model system for understanding zinc finger-DNA interactions," *Structure*, 4:1171-1180, 1996.

Greisman and Pabo, "A general strategy for selecting high-affinity zinc finger proteins for diverse DNA target sites," *Science*, 275:657-661, 1997.

Hurt et al. "Highly specific zinc finger proteins obtained by directed domain shuffling and cell-based selection," *Proc. Natl. Acad. Sci. USA*, 100:12271-12276, 2003.

International Search Report issued in Application No. PCT/US2009/040617, dated Sep. 14, 2009.

Isalan and Choo, "Rapid, high-throughput engineering of sequence-specific zinc finger DNA-binding proteins," *Methods Enzymol.*, 340:593-609, 2001.

Isalan et al., "Comprehensive DNA recognition through concerted interactions from adjacent zinc fingers," *Biochemistry*, 37:12026-12033, 1998.

Jasin, "Genetic manipulation of genomes with rare-cutting endonucleases," *Trends in Genet.*, 12:224-228, 1996.

Liu et al., "Validated zinc finger protein designs for all 16 GNN DNA triplet targets," *J. Biol. Chem.*, 277:3850-3856, 2002.

Lombardo et al., "Gene editing in human stem cells using zinc finger nucleases and integrase-defective lentiviral vector delivery," *Nat. Biotechnol.*, 25:1298-1306, 2007.

Maeder et al., "Oligomerized pool engineering (OPEN): an 'open source' protocol for making customized zinc-finger arrays," *Nature Protocols*, 4(10):1471-1501, 2009.

Maeder et al., "Rapid 'Open-source' engineering of customized zinc-finger nucleases for highly efficient gene modification." *Molecular Cell*, 31:294-301, 2008.

Mandell and Barbas, "Zinc Finger Tools: custom DNA-binding domains for transcription factors and nucleases," *Nucleic Acids Research*, 34:W516-523, 2006.

Miller et al., "An improved zinc-finger nuclease architecture for highly specific genome editing," *Nat. Biotechnology*, 25:778-785, 2007.

Porteus and Baltimore, "Chimeric nucleases stimulate gene targeting in human cells," *Science*, 300:763, 2003.

Porteus and Carroll, "Gene targeting using zinc finger nucleases," *Nat. Biotechonl.*, 23:967-673, 2005.

Pruett-Miller et al., "Comparison of zinc finger nucleases for use in gene targeting in mammalian cells," *Molec. Therapy*, 16:707-17, 2008.

Ramirez et al., "Unexpected failure rates for modular assembly of engineered zinc fingers," *Nature Methods*, 5:374-375, 2008.

Sander et al., "Zinc Finger Targeter (ZiFiT): an engineered zinc finger/target site design tool," *Nucleic Acids Res.*, 35:W599-605, 2007.

Sander et al., "ZiFiT (Zince Finger Targeter): an updated zinc finger engineering tool," Nucleic Acids Research, 38:W462-W468, 2010.

Segal et al., "Evaluation of a modular strategy for the construction of novel polydactyl zinc finger DNA-binding proteins," *Biochemistry*, 42:2137-2148, 2003.

Segal, "The use of zinc finger peptides to study the role of specific factor binding sites in the chromatin environment," *Methods*, 26:76-83, 2002.

Szczepek et al., "Structure-based redesign of the dimerization interface reduces the toxicity of zinc-finger nucleases," *Nat. Biotechnol.*, 25:786-793, 2007.

Urnov et al., "Highly efficient endogenous human gene correction using designed zinc-finger nucleases," *Nature*, 435:646-651, 2005.

Wolfe et al., "Analysis of zinc fingers optimized via phage display: evaluating the utility of a recognition code," *J. Mol. Biol.*, 285:1917-1934, 1999.

Wright et al., "Standardized reagents and protocols for engineering zinc finger nucleases by modular assembly," *Nat. Protoc.*, 1:1637-1652, 2006.

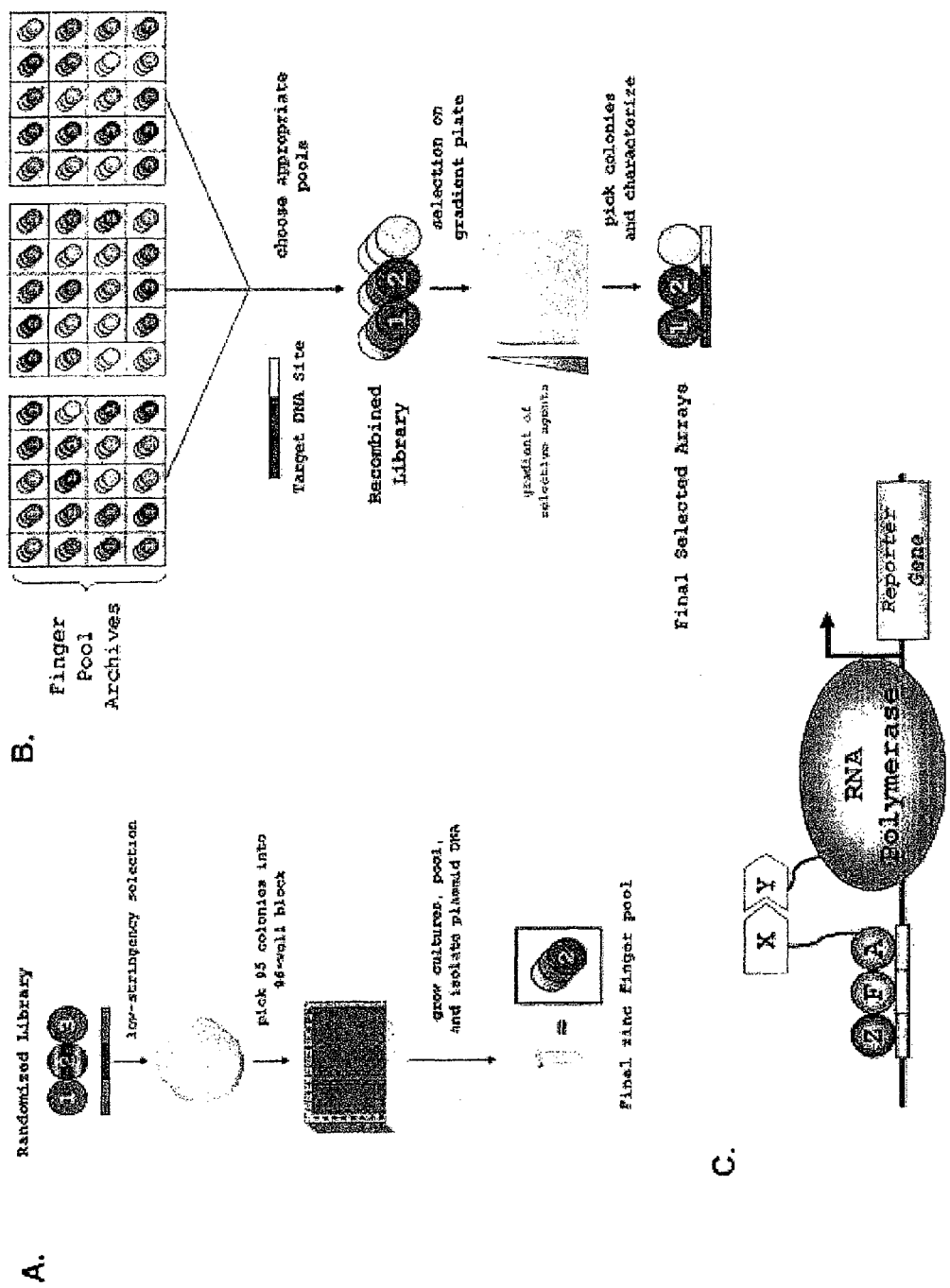
FIG. 1A-C

```
                              SR2163 ZFN site
wild-type SuRA:    GCACACACATACCTGGGGAATCCTTCTaatgaGGCCGGAGATCTTTCCTAATATGTTG
wild-type SuRB:    GCACACACATACCTGGGGAATCCTTCTaatgaGGCCGGAGATCTTTCCTAATATGCTG deletion in SuRA:  GCACACACATACCTGGGGAATCCTTCTA▩TGAGGCCGGAGATCTTTCCTAATATGCTG
```

FIG. 3G

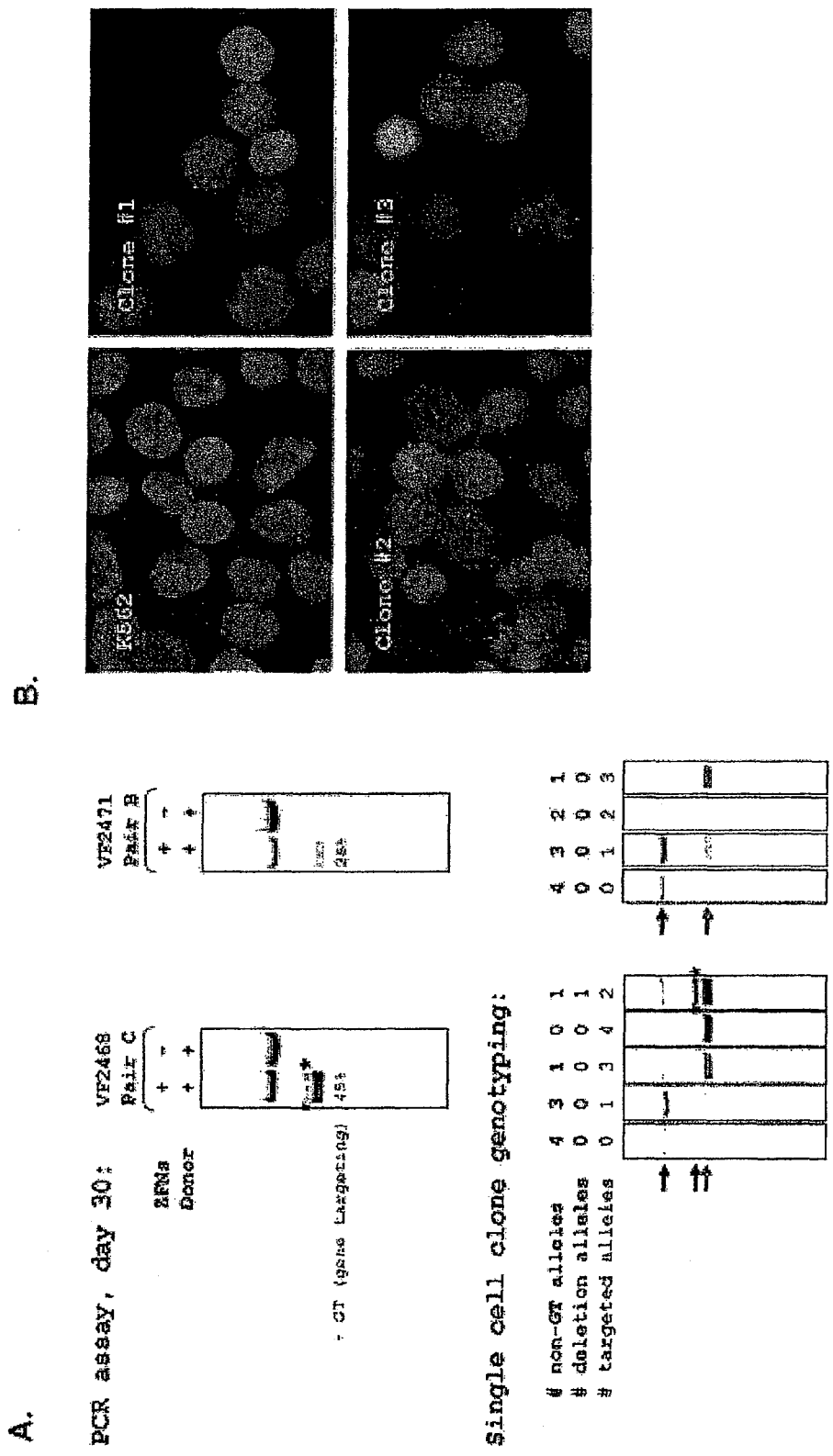
FIG. 5A-B

FIG. 8

```
ATAGAACAGC ACTCGACACA GAGTGAGCAC TTGGCAACTG TTAGCTGTTA
CTAACCTTTC CCATTCTTCC TCCAAACCTA TTCCAACTAT CTGAATCATG
TGCCCCTTCT CTGTGAACCT CTATCATAAT ACTTGTCACA CTGTATTGTA
ATTGTCTCTT TTACTTTCCC TTGTATCTTT TGTGCATAGC AGAGTACCTG
AAACAGGAAG TATTTTAAAT ATTTTGAATC AAATGAGTTA ATAGAATCTT
TACAAATAAG AATATACACt tctgttaGG  ATGAtaattg gagGCAAGTG
AATCCTGAGC GTGATTTGAT AATGACCTAA TAATGATGGG TTTTATTTCC
AGACTTCACT TCTAATGATGTCATG ATTATGGGAG AACTGGAGCC TTCAGAGGGT
AAAATTAAGC ACAGTGGAAG AATTTCATTC TGTTCTCAGT TTTCCTGGAT
TATGCCTGGC ACCATTAAAG AAAATATCAT CTTTGGTGTT TCCTATGATG
AATATAGATA CAGAAGCGTC ATCAAAGCAT GCCAACTAGA AGAGGTAAGA
AACTATGTGA AAACTTTTTG ATTATGCATA TGAACCCTTC ACACTACCCA
AATTATATAT TTGGCTCCAT ATTCAATCGG TTAGTCTACA TATATTTATG
TTTCCTCTAT GGGTAAGCTA CTGTGAATGG ATCAATTAAT AAAACACATG
ACCTATGCTT TAAGAAGCTT GCAAACACAT GAAATAAATG CAATTTATTT
TTTAAATAAT GGGTTCATTT GATCACAATA AATGCATTTT ATGAAATGGT
GAGAATTTTG TTCACTCATT AGTGAGACAA ACGTCCTCAA TGGTTATTTA
TATGGCATGC ATATAAGTGA TATGTGGTAT CTTTTAAAA  GATACCACAA
AATATGCATC TTTAAAAATA TACTCCAAAA ATTATTAAGA TTATTTTAAT
AATTTTAATA ATACTATAGC CTAATGGAAT GAGCATTGAT CTGCCAGCAG
AGAATTAGAG GGGTAAAATT GTGAAGATAT TGTATCCCTG GCTTTGAACA
AATACCATAT AACTTCTAGT GACTGCAATT CTTTGATGCA GAGGCAAAAT
GAAGATGATG TCATTACTCA TTTCACAACA ATATTGGAGA ATGAGCTAAT
TATCTGAAAA TTACATGAAG TATTCCAAGA GAAACCAGTA TATGGATCTT
GTGCTGTTCA CTATGTAAAT TGTGTGATGG TGGGTTCAGT AGTTATTGCT
GTAAATGTTA GGGCAGGGAA TATGTTACTA TGAAGTTTAT TGACAGTATA
CTCCAAATAG
```

FIG. 10

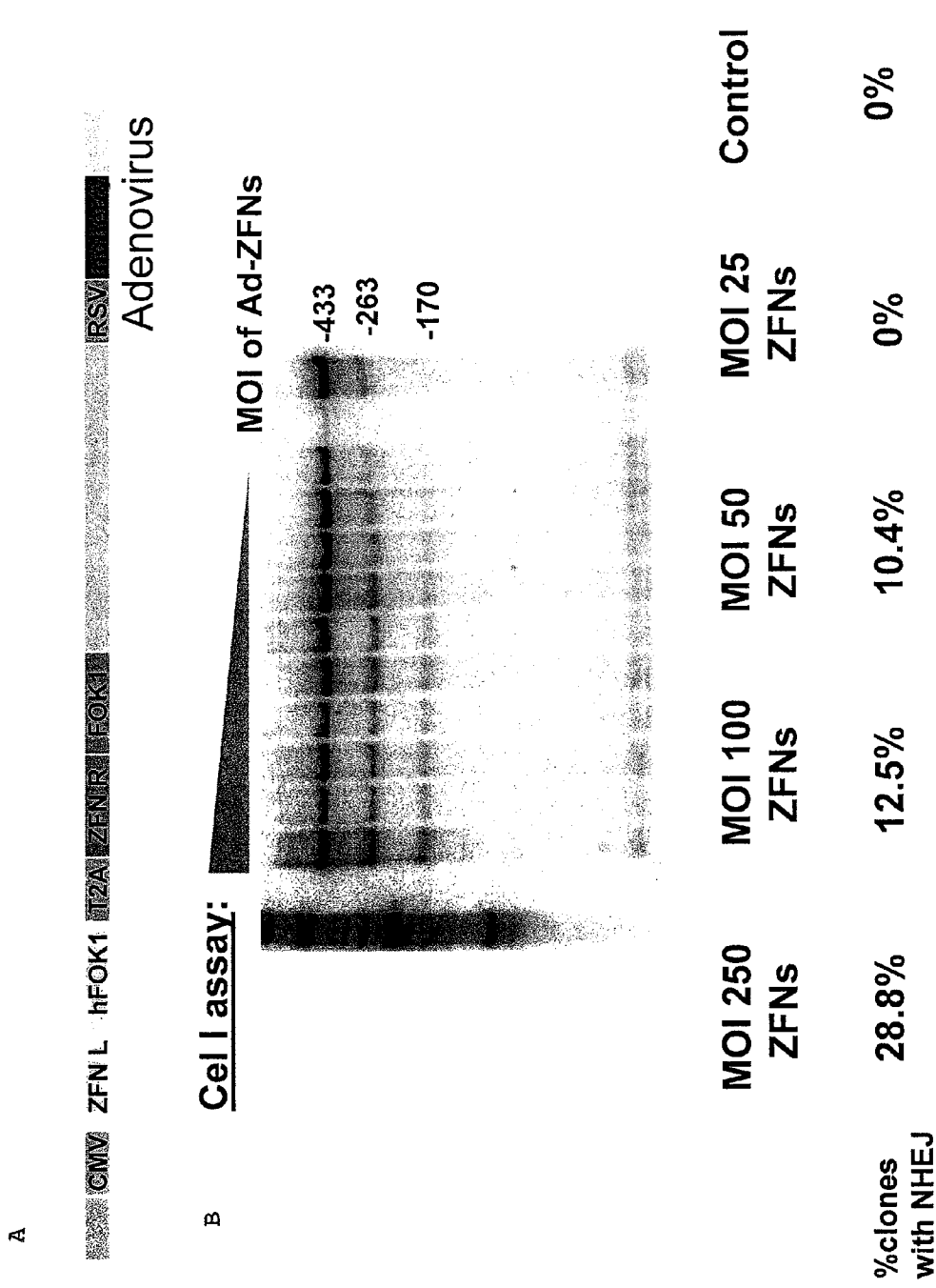
FIG. 11A-B

SEQUENCE LISTING

```
<160> NUMBER OF SEQ ID NOS: 133

<210> SEQ ID NO 1
<211> LENGTH: 9
<212> TYPE: DNA
<213> ORGANISM: Homo sapiens

<400> SEQUENCE: 1 gtggaatta                                                            9

<210> SEQ ID NO 2
<211> LENGTH: 9
<212> TYPE: DNA
<213> ORGANISM: Homo sapiens

<400> SEQUENCE: 2 gagtggtta                                                            9

<210> SEQ ID NO 3
<211> LENGTH: 7
<212> TYPE: PRT
<213> ORGANISM: Artificial Sequence
<220> FEATURE:
<223> OTHER INFORMATION: Synthetic peptide

<400> SEQUENCE: 3

Arg Lys His Ile Leu Asp Thr
1               5

<210> SEQ ID NO 4
<211> LENGTH: 7
<212> TYPE: PRT
```

```
<213> ORGANISM: Artificial Sequence
<220> FEATURE:
<223> OTHER INFORMATION: Synthetic peptide

<400> SEQUENCE: 4

Gln Gly Gly Asn Leu Val Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic peptide

<400> SEQUENCE: 5

Gln Gln Thr Gly Leu Ala Ala
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic peptide

<400> SEQUENCE: 6

Arg Lys Ser Val Leu Leu Val
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide

<400> SEQUENCE: 7

Gln Gly Gly Asn Leu Val Arg
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic peptide

<400> SEQUENCE: 8

Gln Thr Thr Gly Leu Lys Ser
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic peptide

<400> SEQUENCE: 9

Arg Thr Ser Ser Leu Lys Arg
1               5

<210> SEQ ID NO 10
<211> LENGTH: 7
<212> TYPE: PRT
<213> ORGANISM: Artificial Sequence
```

```
<220> FEATURE:
<223> OTHER INFORMATION: Synthetic peptide

<400> SEQUENCE: 10

Arg Arg Glu His Leu Thr Arg
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic peptide

<400> SEQUENCE: 11

Gln Pro Thr Gly Leu Thr Ala
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic peptide

<400> SEQUENCE: 12

Arg Asn Phe Ile Leu Gln Arg
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic peptide

<400> SEQUENCE: 13

Gln Gly Gly Asn Leu Val Arg
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic peptide

<400> SEQUENCE: 14

Gln Val Asn Gly Leu Lys Ala
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic peptide

<400> SEQUENCE: 15

Arg Lys Gly Val Leu Arg Ile
1               5

<210> SEQ ID NO 16
<211> LENGTH: 7
<212> TYPE: PRT
<213> ORGANISM: Artificial Sequence
<220> FEATURE:
```

<223> OTHER INFORMATION: Synthetic peptide

<400> SEQUENCE: 16

Gln Gly Gly Asn Leu Val Arg
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic peptide

<400> SEQUENCE: 17

Gln Gln Thr Gly Leu Asn Val
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic peptide

<400> SEQUENCE: 18

Arg Thr Ser Ser Leu Lys Arg
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic peptide

<400> SEQUENCE: 19

Arg Arg Glu His Leu Thr Arg
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic peptide

<400> SEQUENCE: 20

Gln Pro Thr Gly Leu Thr Ala
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic peptide

<400> SEQUENCE: 21

Arg Lys Ser Val Leu His Asn
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic peptide

```
<400> SEQUENCE: 22

Gln Gly Gly Asn Leu Val Arg
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic peptide

<400> SEQUENCE: 23

Gln Thr Thr Gly Leu Lys Ser
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic peptide

<400> SEQUENCE: 24

Arg Asn Phe Ile Leu Gln Arg
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic peptide

<400> SEQUENCE: 25

Gln Gly Gly Asn Leu Val Arg
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic peptide

<400> SEQUENCE: 26

Gln Gln Thr Gly Leu Ala Ala
1               5

<210> SEQ ID NO 27
<211> LENGTH: 7
<212> TYPE: PRT
<213> ORGANISM: Artificial Sequence
<220> FEATURE:
<223> OTHER INFORMATION: Synthetic peptide

<400> SEQUENCE: 27

Arg Asn Phe Ile Leu Gln Arg
1               5

<210> SEQ ID NO 28
<211> LENGTH: 7
<212> TYPE: PRT
<213> ORGANISM: Artificial Sequence
<220> FEATURE:
<223> OTHER INFORMATION: Synthetic peptide
```

```
<400> SEQUENCE: 28

Gln Gly Gly Asn Leu Val Arg
1               5

<210> SEQ ID NO 29
<211> LENGTH: 7
<212> TYPE: PRT
<213> ORGANISM: Artificial Sequence
<220> FEATURE:
<223> OTHER INFORMATION: Synthetic peptide

<400> SEQUENCE: 29

Gln Val Asn Gly Leu Lys Ala
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic peptide

<400> SEQUENCE: 30

Arg Arg His Val Leu Glu Arg
1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic peptide

<400> SEQUENCE: 31

Gln Gly Gly Asn Leu Val Arg
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic peptide

<400> SEQUENCE: 32

Gln Gln Thr Gly Leu Asn Val
1               5

<210> SEQ ID NO 33
<211> LENGTH: 7
<212> TYPE: PRT
<213> ORGANISM: Artificial Sequence
<220> FEATURE:
<223> OTHER INFORMATION: Synthetic peptide

<400> SEQUENCE: 33

Arg Lys Ser Val Leu Leu Val
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic peptide

<400> SEQUENCE: 34
```

```
Gln Gly Gly Asn Leu Val Arg
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic peptide

<400> SEQUENCE: 35

Gln Gln Thr Gly Leu Ala Ala
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic peptide

<400> SEQUENCE: 36

Arg Asn Phe Ile Leu Gln Arg
1               5

<210> SEQ ID NO 37
<211> LENGTH: 7
<212> TYPE: PRT
<213> ORGANISM: Artificial Sequence
<220> FEATURE:
<223> OTHER INFORMATION: Synthetic peptide

<400> SEQUENCE: 37

Gln Gly Gly Asn Leu Val Arg
1               5

<210> SEQ ID NO 38
<211> LENGTH: 7
<212> TYPE: PRT
<213> ORGANISM: Artificial Sequence
<220> FEATURE:
<223> OTHER INFORMATION: Synthetic peptide

<400> SEQUENCE: 38

Gln Gln Thr Gly Leu Asn Val
1               5

<210> SEQ ID NO 39
<211> LENGTH: 7
<212> TYPE: PRT
<213> ORGANISM: Artificial Sequence
<220> FEATURE:
<223> OTHER INFORMATION: Synthetic peptide

<400> SEQUENCE: 39

Arg Gln Ser Asn Leu Ser Arg
1               5

<210> SEQ ID NO 40
<211> LENGTH: 7
<212> TYPE: PRT
<213> ORGANISM: Artificial Sequence
<220> FEATURE:
<223> OTHER INFORMATION: Synthetic peptide

<400> SEQUENCE: 40
```

Arg Lys Glu His Leu Asp Ile
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic peptide

<400> SEQUENCE: 41

Gln Met Thr Gly Leu Asn Ala
1               5

<210> SEQ ID NO 42
<211> LENGTH: 7
<212> TYPE: PRT
<213> ORGANISM: Artificial Sequence
<220> FEATURE:
<223> OTHER INFORMATION: Synthetic peptide

<400> SEQUENCE: 42

Arg Gln Ser Asn Leu Ala Arg
1               5

<210> SEQ ID NO 43
<211> LENGTH: 7
<212> TYPE: PRT
<213> ORGANISM: Artificial Sequence
<220> FEATURE:
<223> OTHER INFORMATION: Synthetic peptide

<400> SEQUENCE: 43

Arg Lys Glu His Leu Val Gly
1               5

<210> SEQ ID NO 44
<211> LENGTH: 7
<212> TYPE: PRT
<213> ORGANISM: Artificial Sequence
<220> FEATURE:
<223> OTHER INFORMATION: Synthetic peptide

<400> SEQUENCE: 44

Gln Ala Ser Gly Leu Asn Ser
1               5

<210> SEQ ID NO 45
<211> LENGTH: 7
<212> TYPE: PRT
<213> ORGANISM: Artificial Sequence
<220> FEATURE:
<223> OTHER INFORMATION: Synthetic peptide

<400> SEQUENCE: 45

Arg Gln Ser Asn Leu Ser Arg
1               5

<210> SEQ ID NO 46
<211> LENGTH: 7
<212> TYPE: PRT
<213> ORGANISM: Artificial Sequence
<220> FEATURE:
<223> OTHER INFORMATION: Synthetic peptide

<400> SEQUENCE: 46

Arg Lys Glu His Leu Ser Ile

```
<210> SEQ ID NO 47
<211> LENGTH: 7
<212> TYPE: PRT
<213> ORGANISM: Artificial Sequence
<220> FEATURE:
<223> OTHER INFORMATION: Synthetic peptide

<400> SEQUENCE: 47

Gln Arg Thr Gly Leu Thr Ala
1               5

<210> SEQ ID NO 48
<211> LENGTH: 7
<212> TYPE: PRT
<213> ORGANISM: Artificial Sequence
<220> FEATURE:
<223> OTHER INFORMATION: Synthetic peptide

<400> SEQUENCE: 48

Thr Thr His Asn Leu Met Arg
1               5

<210> SEQ ID NO 49
<211> LENGTH: 7
<212> TYPE: PRT
<213> ORGANISM: Artificial Sequence
<220> FEATURE:
<223> OTHER INFORMATION: Synthetic peptide

<400> SEQUENCE: 49

Arg Ala Asp His Leu Lys Val
1               5

<210> SEQ ID NO 50
<211> LENGTH: 7
<212> TYPE: PRT
<213> ORGANISM: Artificial Sequence
<220> FEATURE:
<223> OTHER INFORMATION: Synthetic peptide

<400> SEQUENCE: 50

Gln Gly Thr Gly Leu Arg Ala
1               5

<210> SEQ ID NO 51
<211> LENGTH: 7
<212> TYPE: PRT
<213> ORGANISM: Artificial Sequence
<220> FEATURE:
<223> OTHER INFORMATION: Synthetic peptide

<400> SEQUENCE: 51

Thr Lys His Asn Leu Val Arg
1               5

<210> SEQ ID NO 52
<211> LENGTH: 7
<212> TYPE: PRT
<213> ORGANISM: Artificial Sequence
<220> FEATURE:
<223> OTHER INFORMATION: Synthetic peptide

<400> SEQUENCE: 52

Arg Arg Glu His Leu Asn Ile
1               5
```

<210> SEQ ID NO 53
<211> LENGTH: 7
<212> TYPE: PRT
<213> ORGANISM: Artificial Sequence
<220> FEATURE:
<223> OTHER INFORMATION: Synthetic peptide

<400> SEQUENCE: 53

Gln Thr Ser Gly Leu Thr Ala
1               5

<210> SEQ ID NO 54
<211> LENGTH: 7
<212> TYPE: PRT
<213> ORGANISM: Artificial Sequence
<220> FEATURE:
<223> OTHER INFORMATION: Synthetic peptide

<400> SEQUENCE: 54

Thr Lys His Asn Leu Val Arg
1               5

<210> SEQ ID NO 55
<211> LENGTH: 7
<212> TYPE: PRT
<213> ORGANISM: Artificial Sequence
<220> FEATURE:
<223> OTHER INFORMATION: Synthetic peptide

<400> SEQUENCE: 55

Arg Arg Glu His Leu Asn Ile
1               5

<210> SEQ ID NO 56
<211> LENGTH: 7
<212> TYPE: PRT
<213> ORGANISM: Artificial Sequence
<220> FEATURE:
<223> OTHER INFORMATION: Synthetic peptide

<400> SEQUENCE: 56

Gln Thr Ser Gly Leu Thr Ala
1               5

<210> SEQ ID NO 57
<211> LENGTH: 7
<212> TYPE: PRT
<213> ORGANISM: Artificial Sequence
<220> FEATURE:
<223> OTHER INFORMATION: Synthetic peptide

<400> SEQUENCE: 57

Thr Lys His Asn Leu Val Arg
1               5

<210> SEQ ID NO 58
<211> LENGTH: 7
<212> TYPE: PRT
<213> ORGANISM: Artificial Sequence
<220> FEATURE:
<223> OTHER INFORMATION: Synthetic peptide

<400> SEQUENCE: 58

Arg Gln Glu His Leu Asn Ile
1               5

<210> SEQ ID NO 59
<211> LENGTH: 7
<212> TYPE: PRT
<213> ORGANISM: Artificial Sequence
<220> FEATURE:
<223> OTHER INFORMATION: Synthetic peptide

<400> SEQUENCE: 59

Gln Pro Thr Gly Leu Lys Val
1               5

<210> SEQ ID NO 60
<211> LENGTH: 7
<212> TYPE: PRT
<213> ORGANISM: Artificial Sequence
<220> FEATURE:
<223> OTHER INFORMATION: Synthetic peptide

<400> SEQUENCE: 60

Thr Ala His Asn Leu Met Arg
1               5

<210> SEQ ID NO 61
<211> LENGTH: 7
<212> TYPE: PRT
<213> ORGANISM: Artificial Sequence
<220> FEATURE:
<223> OTHER INFORMATION: Synthetic peptide

<400> SEQUENCE: 61

Arg Arg Glu His Leu Thr Ile
1               5

<210> SEQ ID NO 62
<211> LENGTH: 7
<212> TYPE: PRT
<213> ORGANISM: Artificial Sequence
<220> FEATURE:
<223> OTHER INFORMATION: Synthetic peptide

<400> SEQUENCE: 62

Gln Met Thr Gly Leu Asn Ala
1               5

<210> SEQ ID NO 63
<211> LENGTH: 7
<212> TYPE: PRT
<213> ORGANISM: Artificial Sequence
<220> FEATURE:
<223> OTHER INFORMATION: Synthetic peptide

<400> SEQUENCE: 63

Arg Met Ser Asn Leu Asp Arg
1               5

<210> SEQ ID NO 64
<211> LENGTH: 7
<212> TYPE: PRT
<213> ORGANISM: Artificial Sequence
<220> FEATURE:
<223> OTHER INFORMATION: Synthetic peptide

<400> SEQUENCE: 64

Arg Arg Glu His Leu Thr Ile
1               5

```
<210> SEQ ID NO 65
<211> LENGTH: 7
<212> TYPE: PRT
<213> ORGANISM: Artificial Sequence
<220> FEATURE:
<223> OTHER INFORMATION: Synthetic peptide

<400> SEQUENCE: 65

Gln Gly Thr Gly Leu Arg Ala
1               5

<210> SEQ ID NO 66
<211> LENGTH: 7
<212> TYPE: PRT
<213> ORGANISM: Artificial Sequence
<220> FEATURE:
<223> OTHER INFORMATION: Synthetic peptide

<400> SEQUENCE: 66

Thr Thr His Asn Leu Met Arg
1               5

<210> SEQ ID NO 67
<211> LENGTH: 7
<212> TYPE: PRT
<213> ORGANISM: Artificial Sequence
<220> FEATURE:
<223> OTHER INFORMATION: Synthetic peptide

<400> SEQUENCE: 67

Arg Lys Glu His Leu Ser Ile
1               5

<210> SEQ ID NO 68
<211> LENGTH: 7
<212> TYPE: PRT
<213> ORGANISM: Artificial Sequence
<220> FEATURE:
<223> OTHER INFORMATION: Synthetic peptide

<400> SEQUENCE: 68

Gln Met Thr Gly Leu Asn Ala
1               5

<210> SEQ ID NO 69
<211> LENGTH: 7
<212> TYPE: PRT
<213> ORGANISM: Artificial Sequence
<220> FEATURE:
<223> OTHER INFORMATION: Synthetic peptide

<400> SEQUENCE: 69

Arg Gln Ser Asn Leu Ser Arg
1               5

<210> SEQ ID NO 70
<211> LENGTH: 7
<212> TYPE: PRT
<213> ORGANISM: Artificial Sequence
<220> FEATURE:
<223> OTHER INFORMATION: Synthetic peptide

<400> SEQUENCE: 70

Arg Lys Glu His Leu Asp Ile
1               5

<210> SEQ ID NO 71
```

```
<211> LENGTH: 7
<212> TYPE: PRT
<213> ORGANISM: Artificial Sequence
<220> FEATURE:
<223> OTHER INFORMATION: Synthetic peptide

<400> SEQUENCE: 71

Gln Met Thr Gly Leu Asn Ala
1               5

<210> SEQ ID NO 72
<211> LENGTH: 7
<212> TYPE: PRT
<213> ORGANISM: Artificial Sequence
<220> FEATURE:
<223> OTHER INFORMATION: Synthetic peptide

<400> SEQUENCE: 72

Arg Pro His Asn Leu Leu Arg
1               5

<210> SEQ ID NO 73
<211> LENGTH: 7
<212> TYPE: PRT
<213> ORGANISM: Artificial Sequence
<220> FEATURE:
<223> OTHER INFORMATION: Synthetic peptide

<400> SEQUENCE: 73

Arg Ala Asp His Leu Lys Val
1               5

<210> SEQ ID NO 74
<211> LENGTH: 7
<212> TYPE: PRT
<213> ORGANISM: Artificial Sequence
<220> FEATURE:
<223> OTHER INFORMATION: Synthetic peptide

<400> SEQUENCE: 74

Gln Thr Thr Gly Leu Asn Ala
1               5

<210> SEQ ID NO 75
<211> LENGTH: 7
<212> TYPE: PRT
<213> ORGANISM: Artificial Sequence
<220> FEATURE:
<223> OTHER INFORMATION: Synthetic peptide

<400> SEQUENCE: 75

Lys His Ser Asn Leu Thr Arg
1               5

<210> SEQ ID NO 76
<211> LENGTH: 7
<212> TYPE: PRT
<213> ORGANISM: Artificial Sequence
<220> FEATURE:
<223> OTHER INFORMATION: Synthetic peptide

<400> SEQUENCE: 76

Arg Arg Glu His Leu Thr Ile
1               5

<210> SEQ ID NO 77
<211> LENGTH: 7
```

```
<212> TYPE: PRT
<213> ORGANISM: Artificial Sequence
<220> FEATURE:
<223> OTHER INFORMATION: Synthetic peptide

<400> SEQUENCE: 77

Gln Pro Thr Gly Leu Arg Ala
1               5

<210> SEQ ID NO 78
<211> LENGTH: 7
<212> TYPE: PRT
<213> ORGANISM: Artificial Sequence
<220> FEATURE:
<223> OTHER INFORMATION: Synthetic peptide

<400> SEQUENCE: 78

Arg Gln Ser Asn Leu Ser Arg
1               5

<210> SEQ ID NO 79
<211> LENGTH: 7
<212> TYPE: PRT
<213> ORGANISM: Artificial Sequence
<220> FEATURE:
<223> OTHER INFORMATION: Synthetic peptide

<400> SEQUENCE: 79

Arg Ser Glu His Leu Ala Ile
1               5

<210> SEQ ID NO 80
<211> LENGTH: 7
<212> TYPE: PRT
<213> ORGANISM: Artificial Sequence
<220> FEATURE:
<223> OTHER INFORMATION: Synthetic peptide

<400> SEQUENCE: 80

Gln Arg Val Gly Leu His Ala
1               5

<210> SEQ ID NO 81
<211> LENGTH: 7
<212> TYPE: PRT
<213> ORGANISM: Artificial Sequence
<220> FEATURE:
<223> OTHER INFORMATION: Synthetic peptide

<400> SEQUENCE: 81

Lys His Ser Asn Leu Thr Arg
1               5

<210> SEQ ID NO 82
<211> LENGTH: 7
<212> TYPE: PRT
<213> ORGANISM: Artificial Sequence
<220> FEATURE:
<223> OTHER INFORMATION: Synthetic peptide

<400> SEQUENCE: 82

Arg Ala Asp His Leu Lys Val
1               5

<210> SEQ ID NO 83
<211> LENGTH: 7
<212> TYPE: PRT
```

<213> ORGANISM: Artificial Sequence
<220> FEATURE:
<223> OTHER INFORMATION: Synthetic peptide

<400> SEQUENCE: 83

Gln Asn Thr Gly Leu His Ala
1               5

<210> SEQ ID NO 84
<211> LENGTH: 7
<212> TYPE: PRT
<213> ORGANISM: Artificial Sequence
<220> FEATURE:
<223> OTHER INFORMATION: Synthetic peptide

<400> SEQUENCE: 84

Arg Gln Ser Asn Leu Ser Arg
1               5

<210> SEQ ID NO 85
<211> LENGTH: 7
<212> TYPE: PRT
<213> ORGANISM: Artificial Sequence
<220> FEATURE:
<223> OTHER INFORMATION: Synthetic peptide

<400> SEQUENCE: 85

Arg Asn Glu His Leu Val Leu
1               5

<210> SEQ ID NO 86
<211> LENGTH: 7
<212> TYPE: PRT
<213> ORGANISM: Artificial Sequence
<220> FEATURE:
<223> OTHER INFORMATION: Synthetic peptide

<400> SEQUENCE: 86

Gln Lys Thr Gly Leu Arg Val
1               5

<210> SEQ ID NO 87
<211> LENGTH: 7
<212> TYPE: PRT
<213> ORGANISM: Artificial Sequence
<220> FEATURE:
<223> OTHER INFORMATION: Synthetic peptide

<400> SEQUENCE: 87

Lys His Ser Asn Leu Thr Arg
1               5

<210> SEQ ID NO 88
<211> LENGTH: 7
<212> TYPE: PRT
<213> ORGANISM: Artificial Sequence
<220> FEATURE:
<223> OTHER INFORMATION: Synthetic peptide

<400> SEQUENCE: 88

Arg Arg Glu His Leu Thr Ile
1               5

<210> SEQ ID NO 89
<211> LENGTH: 7
<212> TYPE: PRT
<213> ORGANISM: Artificial Sequence
<220> FEATURE:
<223> OTHER INFORMATION: Synthetic peptide

<400> SEQUENCE: 89

Gln Met Thr Gly Leu Asn Ala
1               5

<210> SEQ ID NO 90
<211> LENGTH: 7
<212> TYPE: PRT
<213> ORGANISM: Artificial Sequence
<220> FEATURE:
<223> OTHER INFORMATION: Synthetic peptide

<400> SEQUENCE: 90

Lys His Ser Asn Leu Thr Arg
1               5

<210> SEQ ID NO 91
<211> LENGTH: 7
<212> TYPE: PRT
<213> ORGANISM: Artificial Sequence
<220> FEATURE:
<223> OTHER INFORMATION: Synthetic peptide

<400> SEQUENCE: 91

Arg Arg Glu His Leu Thr Ile
1               5

<210> SEQ ID NO 92
<211> LENGTH: 7
<212> TYPE: PRT
<213> ORGANISM: Artificial Sequence
<220> FEATURE:
<223> OTHER INFORMATION: Synthetic peptide

<400> SEQUENCE: 92

Gln Met Thr Gly Leu Asn Ala
1               5

<210> SEQ ID NO 93
<211> LENGTH: 7
<212> TYPE: PRT
<213> ORGANISM: Artificial Sequence
<220> FEATURE:
<223> OTHER INFORMATION: Synthetic peptide

<400> SEQUENCE: 93

Arg His Ser Asn Leu Thr Arg
1               5

<210> SEQ ID NO 94
<211> LENGTH: 7
<212> TYPE: PRT
<213> ORGANISM: Artificial Sequence
<220> FEATURE:
<223> OTHER INFORMATION: Synthetic peptide

<400> SEQUENCE: 94

Arg Gln Glu His Leu Asn Ile
1               5

<210> SEQ ID NO 95
<211> LENGTH: 7
<212> TYPE: PRT
<213> ORGANISM: Artificial Sequence
<220> FEATURE:

<223> OTHER INFORMATION: Synthetic peptide

<400> SEQUENCE: 95

Gln Met Thr Gly Leu Asn Ala
1               5

<210> SEQ ID NO 96
<211> LENGTH: 7
<212> TYPE: PRT
<213> ORGANISM: Artificial Sequence
<220> FEATURE:
<223> OTHER INFORMATION: Synthetic peptide

<400> SEQUENCE: 96

Lys Lys Thr Asn Leu Thr Arg
1               5

<210> SEQ ID NO 97
<211> LENGTH: 7
<212> TYPE: PRT
<213> ORGANISM: Artificial Sequence
<220> FEATURE:
<223> OTHER INFORMATION: Synthetic peptide

<400> SEQUENCE: 97

Arg Arg Glu His Leu Thr Ile
1               5

<210> SEQ ID NO 98
<211> LENGTH: 7
<212> TYPE: PRT
<213> ORGANISM: Artificial Sequence
<220> FEATURE:
<223> OTHER INFORMATION: Synthetic peptide

<400> SEQUENCE: 98

Gln Gln Thr Gly Leu Asn Val
1               5

<210> SEQ ID NO 99
<211> LENGTH: 7
<212> TYPE: PRT
<213> ORGANISM: Artificial Sequence
<220> FEATURE:
<223> OTHER INFORMATION: Synthetic peptide

<400> SEQUENCE: 99

Lys His Ser Asn Leu Thr Arg
1               5

<210> SEQ ID NO 100
<211> LENGTH: 7
<212> TYPE: PRT
<213> ORGANISM: Artificial Sequence
<220> FEATURE:
<223> OTHER INFORMATION: Synthetic peptide

<400> SEQUENCE: 100

Arg Lys Glu His Leu Ser Ile
1               5

<210> SEQ ID NO 101
<211> LENGTH: 7
<212> TYPE: PRT
<213> ORGANISM: Artificial Sequence
<220> FEATURE:
<223> OTHER INFORMATION: Synthetic peptide

<400> SEQUENCE: 101

Gln Met Thr Gly Leu Asn Ala
1               5

<210> SEQ ID NO 102
<211> LENGTH: 7
<212> TYPE: PRT
<213> ORGANISM: Artificial Sequence
<220> FEATURE:
<223> OTHER INFORMATION: Synthetic peptide

<400> SEQUENCE: 102

Lys His Ser Asn Leu Thr Arg
1               5

<210> SEQ ID NO 103
<211> LENGTH: 7
<212> TYPE: PRT
<213> ORGANISM: Artificial Sequence
<220> FEATURE:
<223> OTHER INFORMATION: Synthetic peptide

<400> SEQUENCE: 103

Arg Lys Glu His Leu Thr Ile
1               5

<210> SEQ ID NO 104
<211> LENGTH: 7
<212> TYPE: PRT
<213> ORGANISM: Artificial Sequence
<220> FEATURE:
<223> OTHER INFORMATION: Synthetic peptide

<400> SEQUENCE: 104

Gln Arg Thr Gly Leu Ser Ile
1               5

<210> SEQ ID NO 105
<211> LENGTH: 7
<212> TYPE: PRT
<213> ORGANISM: Artificial Sequence
<220> FEATURE:
<223> OTHER INFORMATION: Synthetic peptide

<400> SEQUENCE: 105

Lys His Gly Asn Leu Thr Arg
1               5

<210> SEQ ID NO 106
<211> LENGTH: 7
<212> TYPE: PRT
<213> ORGANISM: Artificial Sequence
<220> FEATURE:
<223> OTHER INFORMATION: Synthetic peptide

<400> SEQUENCE: 106

Arg Arg Glu His Leu Thr Ile
1               5

<210> SEQ ID NO 107
<211> LENGTH: 7
<212> TYPE: PRT
<213> ORGANISM: Artificial Sequence
<220> FEATURE:
<223> OTHER INFORMATION: Synthetic peptide

```
<400> SEQUENCE: 107

Gln Gln Thr Gly Leu Asn Val
1               5

<210> SEQ ID NO 108
<211> LENGTH: 7
<212> TYPE: PRT
<213> ORGANISM: Artificial Sequence
<220> FEATURE:
<223> OTHER INFORMATION: Synthetic peptide

<400> SEQUENCE: 108

Lys His Ser Asn Leu Thr Arg
1               5

<210> SEQ ID NO 109
<211> LENGTH: 7
<212> TYPE: PRT
<213> ORGANISM: Artificial Sequence
<220> FEATURE:
<223> OTHER INFORMATION: Synthetic peptide

<400> SEQUENCE: 109

Arg Lys Glu His Leu Asp Ile
1               5

<210> SEQ ID NO 110
<211> LENGTH: 7
<212> TYPE: PRT
<213> ORGANISM: Artificial Sequence
<220> FEATURE:
<223> OTHER INFORMATION: Synthetic peptide

<400> SEQUENCE: 110

Gln Met Thr Gly Leu Asn Ala
1               5

<210> SEQ ID NO 111
<211> LENGTH: 14
<212> TYPE: PRT
<213> ORGANISM: Artificial Sequence
<220> FEATURE:
<223> OTHER INFORMATION: Synthetic peptide

<400> SEQUENCE: 111

Cys Asn Asn Cys Asn Asn Asn His Asn Asn Asn Cys
1               5                   10

<210> SEQ ID NO 112
<211> LENGTH: 24
<212> TYPE: PRT
<213> ORGANISM: Artificial Sequence
<220> FEATURE:
<223> OTHER INFORMATION: Synthetic peptide

<400> SEQUENCE: 112

Cys Asn Asn Asn Asn Asn Cys Asn Asn Asn Asn Asn Asn Asn Asn
1               5                   10                  15

Asn His Asn Asn Asn Asn Asn Cys
            20

<210> SEQ ID NO 113
<211> LENGTH: 10
<212> TYPE: PRT
<213> ORGANISM: Artificial Sequence
<220> FEATURE:
```

<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 113

Cys Xaa Cys Xaa Phe Xaa Leu His Xaa His
1               5                   10

<210> SEQ ID NO 114
<211> LENGTH: 6132
<212> TYPE: DNA
<213> ORGANISM: Homo sapiens

<400> SEQUENCE: 114

| | | | | | |
|---|---|---|---|---|---|
| aattggaagc | aaatgacatc | acagcaggtc | agagaaaaag | ggttgagcgg | caggcaccca | 60 |
| gagtagtagg | tctttggcat | taggagcttg | agcccagacg | gccctagcag | ggaccccagc | 120 |
| gcccgagaga | ccatgcagag | gtcgcctctg | gaaaaggcca | gcgttgtctc | caaacttttt | 180 |
| ttcagctgga | ccagaccaat | tttgaggaaa | ggatacagac | agcgcctgga | attgtcagac | 240 |
| atataccaaa | tcccttctgt | tgattctgct | gacaatctat | ctgaaaaatt | ggaaagagaa | 300 |
| tgggatagag | agctggcttc | aaagaaaaat | cctaaactca | ttaatgccct | tcggcgatgt | 360 |
| ttttttctgga | gatttatgtt | ctatggaatc | tttttatatt | taggggaagt | caccaaagca | 420 |
| gtacagcctc | tcttactggg | aagaatcata | gcttcctatg | acccggataa | caaggaggaa | 480 |
| cgctctatcg | cgatttatct | aggcataggc | ttatgcctttc | tctttattgt | gaggacactg | 540 |
| ctcctacacc | cagccatttt | tggccttcat | cacattggaa | tgcagatgag | aatagctatg | 600 |
| tttagtttga | tttataagaa | gactttaaag | ctgtcaagcc | gtgttctaga | taaaataagt | 660 |
| attggacaac | ttgttagtct | ccttttccaac | aacctgaaca | aatttgatga | aggacttgca | 720 |
| ttggcacatt | tcgtgtggat | cgctccttttg | caagtggcac | tcctcatggg | gctaatctgg | 780 |
| gagttgttac | aggcgtctgc | cttctgtgga | cttggtttcc | tgatagtcct | tgcccttttt | 840 |
| caggctgggc | tagggagaat | gatgatgaag | tacagagatc | agagagctgg | aagatcagt | 900 |
| gaaagacttg | tgattacctc | agaaatgatt | gaaaatatcc | aatctgttaa | ggcatactgc | 960 |
| tgggaagaag | caatggaaaa | aatgattgaa | aacttaagac | aaacagaact | gaaactgact | 1020 |
| cggaaggcag | cctatgtgag | atacttcaat | agctcagcct | tcttcttctc | agggttcttt | 1080 |
| gtggtgtttt | tatctgtgct | tccctatgca | ctaatcaaag | gaatcatcct | ccggaaaata | 1140 |
| ttcaccacca | tctcattctg | cattgttctg | cgcatggcgg | tcactcggca | atttcccctgg | 1200 |
| gctgtacaaa | catggtatga | ctctcttgga | gcaataaaca | aaatacagga | tttcttacaa | 1260 |
| aagcaagaat | ataagacatt | ggaatataac | ttaacgacta | cagaagtagt | gatggagaat | 1320 |
| gtaacagcct | tctggagga | gggatttggg | gaattatttg | agaaagcaaa | acaaaacaat | 1380 |
| aacaatagaa | aaacttctaa | tggtgatgac | agcctcttct | tcagtaattt | ctcacttctt | 1440 |

-continued

```
ggtactcctg tcctgaaaga tattaatttc aagatagaaa gaggacagtt gttggcggtt       1500
gctggatcca ctggagcagg caagacttca cttctaatgg tgattatggg agaactggag       1560
ccttcagagg gtaaaattaa gcacagtgga agaatttcat tctgttctca gttttcctgg       1620
attatgcctg gcaccattaa agaaaatatc atctttggtg tttcctatga tgaatataga       1680
tacagaagcg tcatcaaagc atgccaacta gaagaggaca tctccaagtt tgcagagaaa       1740
gacaatatag ttcttggaga aggtggaatc acactgagtg gaggtcaacg agcaagaatt       1800
tctttagcaa gagcagtata caaagatgct gatttgtatt tattagactc tccttttgga       1860
tacctagatg ttttaacaga aaagaaata tttgaaagct gtgtctgtaa actgatggct        1920
aacaaaacta ggattttggt cacttctaaa atggaacatt taaagaaagc tgacaaaata       1980
ttaattttgc atgaaggtag cagctatttt tatgggacat tttcagaact ccaaaatcta       2040
cagccagact ttagctcaaa actcatggga tgtgattctt tcgaccaatt tagtgcagaa       2100
agaagaaatt caatcctaac tgagacctta caccgtttct cattagaagg agatgctcct       2160
gtctcctgga cagaaacaaa aaaacaatct tttaaacaga ctggagagtt tggggaaaaa       2220
aggaagaatt ctattctcaa tccaatcaac tctatacgaa aattttccat tgtgcaaaag       2280
actcccttac aaatgaatgg catcgaagag gattctgatg agcctttaga gagaaggctg       2340
tccttagtac cagattctga gcagggagag gcgatactgc ctcgcatcag cgtgatcagc       2400
actggcccca cgcttcaggc acgaaggagg cagtctgtcc tgaacctgat gacacactca       2460
gttaaccaag gtcagaacat tcaccgaaag acaacagcat ccacacgaaa agtgtcactg       2520
gcccctcagg caaacttgac tgaactggat atatattcaa gaaggttatc tcaagaaact       2580
ggcttggaaa taagtgaaga aattaacgaa gaagacttaa aggagtgctt ttttgatgat       2640
atggagagca taccagcagt gactacatgg aacacatacc ttcgatatat tactgtccac       2700
aagagcttaa ttttttgtgct aatttggtgc ttagtaattt ttctggcaga ggtggctgct       2760
tctttggttg tgctgtggct ccttggaaac actcctcttc aagacaaagg gaatagtact       2820
catagtagaa ataacagcta tgcagtgatt atcaccagca ccagttcgta ttatgtgttt       2880
tacatttacg tgggagtagc cgacactttg cttgctatgg gattcttcag aggtctacca       2940
ctggtgcata ctctaatcac agtgtcgaaa attttacacc acaaaatgtt acattctgtt       3000
cttcaagcac ctatgtcaac cctcaacacg ttgaaagcag gtgggattct taatagattc       3060
tccaaagata tagcaatttt ggatgacctt ctgcctctta ccatatttga cttcatccag       3120
ttgttattaa ttgtgattgg agctatagca gttgtcgcag ttttacaacc ctacatcttt       3180
gttgcaacag tgccagtgat agtggctttt attatgttga gagcatattt cctccaaacc       3240
tcacagcaac tcaaacaact ggaatctgaa ggcaggagtc caattttcac tcatcttgtt       3300
acaagcttaa aaggactatg gacacttcgt gccttcggac ggcagcctta ctttgaaact       3360
ctgttccaca agctctgaa tttacatact gccaactggt tcttgtacct gtcaacactg       3420
cgctggttcc aaatgagaat agaaatgatt tttgtcatct tcttcattgc tgttaccttc       3480
atttccattt taacaacagg agaaggagaa ggaagagttg gtattatcct gactttagcc       3540
atgaatatca tgagtacatt gcagtgggct gtaaactcca gcatagatgt ggatagcttg       3600
atgcgatctg tgagccgagt ctttaagttc attgacatgc caacagaagg taaacctacc       3660
aagtcaacca aaccatacaa gaatggccaa ctctcgaaag ttatgattat tgagaattca       3720
cacgtgaaga aagatgacat ctggcccctca ggggccaaa tgactgtcaa agatctcaca       3780
gcaaaataca cagaaggtgg aaatgccata ttagagaaca tttccttctc aataagtcct       3840
```

```
ggccagaggg tgggcctctt gggaagaact ggatcaggga agagtacttt gttatcagct    3900
tttttgagac tactgaacac tgaaggagaa atccagatcg atggtgtgtc ttgggattca    3960
ataactttgc aacagtggag gaaagccttt ggagtgatac cacagaaagt atttattttt    4020
tctggaacat ttagaaaaaa cttggatccc tatgaacagt ggagtgatca agaaatatgg    4080
aaagttgcag atgaggttgg gctcagatct gtgatagaac agtttcctgg gaagcttgac    4140
tttgtccttg tggatggggg ctgtgtccta agccatggcc acaagcagtt gatgtgcttg    4200
gctagatctg ttctcagtaa ggcgaagatc ttgctgcttg atgaacccag tgctcatttg    4260
gatccagtaa cataccaaat aattagaaga actctaaaac aagcatttgc tgattgcaca    4320
gtaattctct gtgaacacag gatagaagca atgctggaat gccaacaatt tttggtcata    4380
gaagagaaca aagtgcggca gtacgattcc atccagaaac tgctgaacga gaggagcctc    4440
ttccggcaag ccatcagccc ctccgacagg gtgaagctct tccccaccg gaactcaagc     4500 aagtgcaagt ctaagcccca gattgctgct ctgaaagagg agacagaaga agaggtgcaa    4560
gatacaaggc tttagagagc agcataaatg ttgacatggg acatttgctc atggaattgg    4620
agctcgtggg acagtcacct catggaattg gagctcgtgg aacagttacc tctgcctcag    4680
aaaacaagga tgaattaagt ttttttttaa aaagaaaca tttggtaagg ggaattgagg     4740
acactgatat gggtcttgat aaatggcttc ctggcaatag tcaaattgtg tgaaaggtac    4800
ttcaaatcct tgaagattta ccacttgtgt tttgcaagcc agattttcct gaaaacccctt   4860 gccatgtgct agtaattgga aaggcagctc taaatgtcaa tcagcctagt tgatcagctt    4920
attgtctagt gaaactcgtt aatttgtagt gttggagaag aactgaaatc atacttctta    4980
gggttatgat taagtaatga taactggaaa cttcagcggt ttatataagc ttgtattcct    5040
ttttctctcc tctcccatg atgtttagaa acacaactat attgtttgct aagcattcca     5100
actatctcat ttccaagcaa gtattagaat accacaggaa ccacaagact gcacatcaaa    5160
atatgcccca ttcaacatct agtgagcagt caggaaagag aacttccaga tcctggaaat    5220
cagggttagt attgtccagg tctaccaaaa atctcaatat ttcagataat cacaatacat    5280
cccttacctg ggaaagggct gttataatct ttcacagggg acaggatggt tcccttgatg    5340
aagaagttga tatgcctttt cccaactcca gaaagtgaca agctcacaga cctttgaact    5400
agagtttagc tggaaaagta tgttagtgca aattgtcaca ggacagccct tctttccaca    5460
gaagctccag gtagagggtg tgtaagtaga taggccatgg gcactgtggg tagacacaca    5520
tgaagtccaa gcatttagat gtataggttg atggtggtat gttttcaggc tagatgtatg    5580
tacttcatgc tgtctacact aagagagaat gagagacaca ctgaagaagc accaatcatg    5640
aattagtttt atatgcttct gttttataat tttgtgaagc aaaattttt ctctaggaaa     5700 tatttatttt aataatgttt caaacatata taacaatgct gtattttaaa agaatgatta    5760
tgaattacat ttgtataaaa taattttat atttgaaata ttgactttt atggcactag      5820 tatttctatg aaatattatg ttaaaactgg gacaggggag aacctagggt gatattaacc    5880 agggggccatg aatcaccttt tggtctggag ggaagccttg gggctgatgc agttgttgcc   5940
cacagctgta tgattcccag ccagcacagc ctcttagatg cagttctgaa gaagatggta    6000
ccaccagtct gactgtttcc atcaagggta cactgccttc tcaactccaa actgactctt    6060
aagaagactg cattatattt attactgtaa gaaaatatca cttgtcaata aaatccatac    6120
atttgtgtga aa                                                        6132
```

<210> SEQ ID NO 115
<211> LENGTH: 1480
<212> TYPE: PRT
<213> ORGANISM: Homo sapiens

<400> SEQUENCE: 115

```
Met Gln Arg Ser Pro Leu Glu Lys Ala Ser Val Val Ser Lys Leu Phe
1               5                   10                  15

Phe Ser Trp Thr Arg Pro Ile Leu Arg Lys Gly Tyr Arg Gln Arg Leu
            20                  25                  30

Glu Leu Ser Asp Ile Tyr Gln Ile Pro Ser Val Asp Ser Ala Asp Asn
        35                  40                  45

Leu Ser Glu Lys Leu Glu Arg Glu Trp Asp Arg Glu Leu Ala Ser Lys
    50                  55                  60

Lys Asn Pro Lys Leu Ile Asn Ala Leu Arg Arg Cys Phe Phe Trp Arg
65                  70                  75                  80

Phe Met Phe Tyr Gly Ile Phe Leu Tyr Leu Gly Glu Val Thr Lys Ala
                85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
        115                 120                 125

Leu Leu Phe Ile Val Arg Thr Leu Leu Leu His Pro Ala Ile Phe Gly
    130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
        195                 200                 205

Ala Leu Leu Met Gly Leu Ile Trp Glu Leu Leu Gln Ala Ser Ala Phe
    210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
            260                 265                 270

Lys Ala Tyr Cys Trp Glu Glu Ala Met Glu Lys Met Ile Glu Asn Leu
        275                 280                 285

Arg Gln Thr Glu Leu Lys Leu Thr Arg Lys Ala Ala Tyr Val Arg Tyr
    290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
            340                 345                 350

Gln Phe Pro Trp Ala Val Gln Thr Trp Tyr Asp Ser Leu Gly Ala Ile
        355                 360                 365

Asn Lys Ile Gln Asp Phe Leu Gln Lys Gln Glu Tyr Lys Thr Leu Glu
    370                 375                 380
```

```
Tyr Asn Leu Thr Thr Thr Glu Val Val Met Glu Asn Val Thr Ala Phe
385                 390                 395                 400

Trp Glu Glu Gly Phe Gly Leu Phe Glu Lys Ala Lys Gln Asn Asn
            405                 410                 415

Asn Asn Arg Lys Thr Ser Asn Gly Asp Asp Ser Leu Phe Phe Ser Asn
            420                 425                 430

Phe Ser Leu Leu Gly Thr Pro Val Leu Lys Asp Ile Asn Phe Lys Ile
            435                 440                 445

Glu Arg Gly Gln Leu Leu Ala Val Ala Gly Ser Thr Gly Ala Gly Lys
            450                 455                 460

Thr Ser Leu Leu Met Val Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr
            500                 505                 510

Asp Glu Tyr Arg Tyr Arg Ser Val Ile Lys Ala Cys Gln Leu Glu Glu
            515                 520                 525

Asp Ile Ser Lys Phe Ala Glu Lys Asp Asn Ile Val Leu Gly Glu Gly
            530                 535                 540

Gly Ile Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
                565                 570                 575

Tyr Leu Asp Val Leu Thr Glu Lys Glu Ile Phe Glu Ser Cys Val Cys
            580                 585                 590

Lys Leu Met Ala Asn Lys Thr Arg Ile Leu Val Thr Ser Lys Met Glu
            595                 600                 605

His Leu Lys Lys Ala Asp Lys Ile Leu Ile Leu His Glu Gly Ser Ser
            610                 615                 620

Tyr Phe Tyr Gly Thr Phe Ser Glu Leu Gln Asn Leu Gln Pro Asp Phe
625                 630                 635                 640

Ser Ser Lys Leu Met Gly Cys Asp Ser Phe Asp Gln Phe Ser Ala Glu
                645                 650                 655

Arg Arg Asn Ser Ile Leu Thr Glu Thr Leu His Arg Phe Ser Leu Glu
            660                 665                 670

Gly Asp Ala Pro Val Ser Trp Thr Glu Thr Lys Lys Gln Ser Phe Lys
            675                 680                 685

Gln Thr Gly Glu Phe Gly Glu Lys Arg Lys Asn Ser Ile Leu Asn Pro
            690                 695                 700

Ile Asn Ser Ile Arg Lys Phe Ser Ile Val Gln Lys Thr Pro Leu Gln
705                 710                 715                 720

Met Asn Gly Ile Glu Glu Asp Ser Asp Glu Pro Leu Glu Arg Arg Leu
                725                 730                 735

Ser Leu Val Pro Asp Ser Glu Gln Gly Glu Ala Ile Leu Pro Arg Ile
            740                 745                 750

Ser Val Ile Ser Thr Gly Pro Thr Leu Gln Ala Arg Arg Arg Gln Ser
            755                 760                 765

Val Leu Asn Leu Met Thr His Ser Val Asn Gln Gly Gln Asn Ile His
            770                 775                 780

Arg Lys Thr Thr Ala Ser Thr Arg Lys Val Ser Leu Ala Pro Gln Ala
785                 790                 795                 800
```

```
Asn Leu Thr Glu Leu Asp Ile Tyr Ser Arg Arg Leu Ser Gln Glu Thr
                805                 810                 815
Gly Leu Glu Ile Ser Glu Glu Ile Asn Glu Glu Asp Leu Lys Glu Cys
                820                 825                 830
Phe Phe Asp Asp Met Glu Ser Ile Pro Ala Val Thr Thr Trp Asn Thr
                835                 840                 845
Tyr Leu Arg Tyr Ile Thr Val His Lys Ser Leu Ile Phe Val Leu Ile
                850                 855                 860
Trp Cys Leu Val Ile Phe Leu Ala Glu Val Ala Ala Ser Leu Val Val
865                 870                 875                 880
Leu Trp Leu Leu Gly Asn Thr Pro Leu Gln Asp Lys Gly Asn Ser Thr
                885                 890                 895
His Ser Arg Asn Asn Ser Tyr Ala Val Ile Ile Thr Ser Thr Ser Ser
                900                 905                 910
Tyr Tyr Val Phe Tyr Ile Tyr Val Gly Val Ala Asp Thr Leu Leu Ala
                915                 920                 925
Met Gly Phe Phe Arg Gly Leu Pro Leu Val His Thr Leu Ile Thr Val
                930                 935                 940
Ser Lys Ile Leu His His Lys Met Leu His Ser Val Leu Gln Ala Pro
945                 950                 955                 960
Met Ser Thr Leu Asn Thr Leu Lys Ala Gly Gly Ile Leu Asn Arg Phe
                965                 970                 975
Ser Lys Asp Ile Ala Ile Leu Asp Asp Leu Leu Pro Leu Thr Ile Phe
                980                 985                 990
Asp Phe Ile Gln Leu Leu Leu Ile Val Ile Gly Ala Ile Ala Val Val
                995                 1000                1005
Ala Val Leu Gln Pro Tyr Ile Phe Val Ala Thr Val Pro Val Ile
                1010                1015                1020
Val Ala Phe Ile Met Leu Arg Ala Tyr Phe Leu Gln Thr Ser Gln
                1025                1030                1035
Gln Leu Lys Gln Leu Glu Ser Glu Gly Arg Ser Pro Ile Phe Thr
                1040                1045                1050
His Leu Val Thr Ser Leu Lys Gly Leu Trp Thr Leu Arg Ala Phe
                1055                1060                1065
Gly Arg Gln Pro Tyr Phe Glu Thr Leu Phe His Lys Ala Leu Asn
                1070                1075                1080
Leu His Thr Ala Asn Trp Phe Leu Tyr Leu Ser Thr Leu Arg Trp
                1085                1090                1095
Phe Gln Met Arg Ile Glu Met Ile Phe Val Ile Phe Phe Ile Ala
                1100                1105                1110
Val Thr Phe Ile Ser Ile Leu Thr Thr Gly Glu Gly Glu Gly Arg
                1115                1120                1125
Val Gly Ile Ile Leu Thr Leu Ala Met Asn Ile Met Ser Thr Leu
                1130                1135                1140
Gln Trp Ala Val Asn Ser Ser Ile Asp Val Asp Ser Leu Met Arg
                1145                1150                1155
Ser Val Ser Arg Val Phe Lys Phe Ile Asp Met Pro Thr Glu Gly
                1160                1165                1170
Lys Pro Thr Lys Ser Thr Lys Pro Tyr Lys Asn Gly Gln Leu Ser
                1175                1180                1185
Lys Val Met Ile Ile Glu Asn Ser His Val Lys Lys Asp Asp Ile
                1190                1195                1200
Trp Pro Ser Gly Gly Gln Met Thr Val Lys Asp Leu Thr Ala Lys
```

```
                    1205                 1210                 1215
Tyr Thr Glu Gly Gly Asn Ala Ile Leu Glu Asn Ile Ser Phe Ser
        1220                 1225                 1230

Ile Ser Pro Gly Gln Arg Val Gly Leu Leu Gly Arg Thr Gly Ser
        1235                 1240                 1245

Gly Lys Ser Thr Leu Leu Ser Ala Phe Leu Arg Leu Leu Asn Thr
        1250                 1255                 1260

Glu Gly Glu Ile Gln Ile Asp Gly Val Ser Trp Asp Ser Ile Thr
        1265                 1270                 1275

Leu Gln Gln Trp Arg Lys Ala Phe Gly Val Ile Pro Gln Lys Val
        1280                 1285                 1290

Phe Ile Phe Ser Gly Thr Phe Arg Lys Asn Leu Asp Pro Tyr Glu
        1295                 1300                 1305

Gln Trp Ser Asp Gln Glu Ile Trp Lys Val Ala Asp Glu Val Gly
        1310                 1315                 1320

Leu Arg Ser Val Ile Glu Gln Phe Pro Gly Lys Leu Asp Phe Val
        1325                 1330                 1335

Leu Val Asp Gly Gly Cys Val Leu Ser His Gly His Lys Gln Leu
        1340                 1345                 1350

Met Cys Leu Ala Arg Ser Val Leu Ser Lys Ala Lys Ile Leu Leu
        1355                 1360                 1365

Leu Asp Glu Pro Ser Ala His Leu Asp Pro Val Thr Tyr Gln Ile
        1370                 1375                 1380

Ile Arg Arg Thr Leu Lys Gln Ala Phe Ala Asp Cys Thr Val Ile
        1385                 1390                 1395

Leu Cys Glu His Arg Ile Glu Ala Met Leu Glu Cys Gln Gln Phe
        1400                 1405                 1410

Leu Val Ile Glu Glu Asn Lys Val Arg Gln Tyr Asp Ser Ile Gln
        1415                 1420                 1425

Lys Leu Leu Asn Glu Arg Ser Leu Phe Arg Gln Ala Ile Ser Pro
        1430                 1435                 1440

Ser Asp Arg Val Lys Leu Phe Pro His Arg Asn Ser Ser Lys Cys
        1445                 1450                 1455

Lys Ser Lys Pro Gln Ile Ala Ala Leu Lys Glu Glu Thr Glu Glu
        1460                 1465                 1470

Glu Val Gln Asp Thr Arg Leu
        1475                 1480

<210> SEQ ID NO 116
<211> LENGTH: 258
<212> TYPE: DNA
<213> ORGANISM: Homo sapiens
<220> FEATURE:
<221> NAME/KEY: misc_feature
<222> LOCATION: (66)..(66)
<223> OTHER INFORMATION: n is a, c, g, or t

<400> SEQUENCE: 116
cccggggagc gccccttcca gtgtcgcatt tgcatgcgga acttttcgag gaacttcatc      60
cttcanaggc atacccgtac tcataccggt gaaaaaccgt ttcagtgtcg gatctgtatg     120
cgaaatttct cccagggggg gaatttggtg cggcatctac gtacgcacac cggcgagaag     180
ccattccaat gccgaatatg catgcgcaac ttcagtcagc agacggggct gaacgtgcac     240
ctaaaaaccc acctgagg                                                    258
```

```
<210> SEQ ID NO 117
<211> LENGTH: 258
<212> TYPE: DNA
<213> ORGANISM: Homo sapiens

<400> SEQUENCE: 117
cccggggagc gcccccttcca gtgtcgcatt tgcatgcgga acttttcgac caagcacaac      60
cttgtcaggc atacccgtac tcataccggt gaaaaaccgt ttcagtgtcg gatctgtatg     120
cgaaatttct cccggcgcga gcacttgaac atccatctac gtacgcacac cggcgagaag     180
ccattccaat gccgaatatg catgcgcaac ttcagtcaga ccagcgggct gaccgcccac     240
ctaaaaaccc acctgagg                                                   258

<210> SEQ ID NO 118
<211> LENGTH: 258
<212> TYPE: DNA
<213> ORGANISM: Homo sapiens

<400> SEQUENCE: 118
cccggggagc gcccccttcca gtgtcgcatt tgcatgcgga acttttcgag gaacttcatc      60
cttcagaggc atacccgtac tcataccggt gaaaaaccgt ttcagtgtcg gatctgtatg     120
cgaaatttct cccaggggggg gaatttggtg cggcatctac gtacgcacac cggcgagaag     180
ccattccaat gccgaatatg catgcgcaac ttcagtcagc agacggggct gaacgtgcac     240
ctaaaaaccc acctgagg                                                   258

<210> SEQ ID NO 119
<211> LENGTH: 258
<212> TYPE: DNA
<213> ORGANISM: Homo sapiens

<400> SEQUENCE: 119
cccggggagc gcccccttcca gtgtcgcatt tgcatgcgga acttttcgag acagagcaac      60
cttagcaggc atacccgtac tcataccggt gaaaaaccgt ttcagtgtcg gatctgtatg     120
cgaaatttct cccgcaacga gcacttggtc ctgcatctac gtacgcacac cggcgagaag     180
ccattccaat gccgaatatg catgcgcaac ttcagtcaga agaccggcct gcgggtgcac     240
ctaaaaaccc acctgagg                                                   258

<210> SEQ ID NO 120
<211> LENGTH: 60
<212> TYPE: DNA
<213> ORGANISM: Artificial
<220> FEATURE:
<223> OTHER INFORMATION: Synthetic oligonucleotide

<400> SEQUENCE: 120
tcggcggagc cgccaaagca atgccaccca tgccctgggg tgcccaggg gacgtcccca       60

<210> SEQ ID NO 121
<211> LENGTH: 40
<212> TYPE: DNA
<213> ORGANISM: Artificial
<220> FEATURE:
<223> OTHER INFORMATION: Synthetic oligonucleotide

<400> SEQUENCE: 121
ccagacttca cttctaatgg tgattatggg agaactggag                            40

<210> SEQ ID NO 122
```

```
<211> LENGTH: 57
<212> TYPE: DNA
<213> ORGANISM: Artificial
<220> FEATURE:
<223> OTHER INFORMATION: Synthetic oligonucleotide

<400> SEQUENCE: 122
gcacacacat acctggggaa tccttctaat gaggcggaga tctttcctaa tatgttg      57

<210> SEQ ID NO 123
<211> LENGTH: 57
<212> TYPE: DNA
<213> ORGANISM: Artificial
<220> FEATURE:
<223> OTHER INFORMATION: Synthetic oligonucleotide

<400> SEQUENCE: 123
gcacacacat acctggggaa tccttctaat gaggcggaga tctttcctaa tatgctg      57

<210> SEQ ID NO 124
<211> LENGTH: 56
<212> TYPE: DNA
<213> ORGANISM: Artificial
<220> FEATURE:
<223> OTHER INFORMATION: Synthetic oligonucleotide

<400> SEQUENCE: 124
gcacacacat acctggggaa tccttctatg aggcggagat ctttcctaat atgctg       56

<210> SEQ ID NO 125
<211> LENGTH: 61
<212> TYPE: DNA
<213> ORGANISM: Artificial
<220> FEATURE:
<223> OTHER INFORMATION: Synthetic oligonucleotide

<400> SEQUENCE: 125
aagctgggtg aatggagcga gcagcgtctt cgagagtgag gacgtgtgtg tctgtgtggg   60
t                                                                  61

<210> SEQ ID NO 126
<211> LENGTH: 11
<212> TYPE: DNA
<213> ORGANISM: Artificial
<220> FEATURE:
<223> OTHER INFORMATION: Synthetic oligonucleotide

<400> SEQUENCE: 126
tggggtcgac c                                                        11

<210> SEQ ID NO 127
<211> LENGTH: 15
<212> TYPE: DNA
<213> ORGANISM: Artificial
<220> FEATURE:
<223> OTHER INFORMATION: Synthetic oligonucleotide

<400> SEQUENCE: 127
tggggtcgac cgacc                                                    15

<210> SEQ ID NO 128
<211> LENGTH: 63
<212> TYPE: DNA
<213> ORGANISM: Artificial
<220> FEATURE:
<223> OTHER INFORMATION: Synthetic oligonucleotide
```

-continued

<400> SEQUENCE: 128
gctgggtgaa tggagcgagc agcgtcttcg agagtgagga cgtgtgtgtc tgtgtgggtg       60
agt                                                                    63

<210> SEQ ID NO 129
<211> LENGTH: 63
<212> TYPE: DNA
<213> ORGANISM: Artificial
<220> FEATURE:
<223> OTHER INFORMATION: Synthetic oligonucleotide

<400> SEQUENCE: 129
cacgtttcgt gttcggagcc gctttaaccc actctgtgga agtgctcagc attggagtga       60
atg                                                                    63

<210> SEQ ID NO 130
<211> LENGTH: 33
<212> TYPE: DNA
<213> ORGANISM: Artificial
<220> FEATURE:
<223> OTHER INFORMATION: Synthetic oligonucleotide

<400> SEQUENCE: 130
acttcacttc taatgatgtc atgattatgg gag                                   33

<210> SEQ ID NO 131
<211> LENGTH: 1314
<212> TYPE: DNA
<213> ORGANISM: Artificial
<220> FEATURE:
<223> OTHER INFORMATION: Synthetic oligonucleotide

<400> SEQUENCE: 131
atagaacagc actcgacaca gagtgagcac ttggcaactg ttagctgtta ctaacctttc       60
ccattcttcc tccaaaccta ttccaactat ctgaatcatg tgccccttct ctgtgaacct      120
ctatcataat acttgtcaca ctgtattgta attgtctctt ttactttccc ttgtatcttt      180
tgtgcatagc agagtacctg aaacaggaag tattttaaat attttgaatc aaatgagtta      240
atagaatctt tacaaataag aatatacact tctgttagga tgataattgg aggcaagtga      300
atcctgagcg tgatttgata atgacctaat aatgatgggt tttatttcca gacttcactt      360
ctaatgatgt catgattatg ggagaactgg agccttcaga gggtaaaatt aagcacagtg      420
gaagaatttc attctgttct cagttttcct ggattatgcc tggcaccatt aaagaaaata      480
tcatctttgg tgtttcctat gatgaatata gatacagaag cgtcatcaaa gcatgccaac      540
tagaagaggt aagaaactat gtgaaaactt tttgattatg catatgaacc cttcacacta      600
cccaaattat atatttggct ccatattcaa tcggttagtc tacatatatt tatgtttcct      660
ctatgggtaa gctactgtga atggatcaat taataaaaca catgacctat gctttaagaa      720
gcttgcaaac acatgaaata aatgcaattt attttttaaa taatgggttc atttgatcac      780
aataaatgca ttttatgaaa tggtgagaat tttgttcact cattagtgag acaaacgtcc      840
tcaatggtta tttatatggc atgcataaa gtgatatgtg gtatcttttt aaaagatacc      900 acaaatatg catctttaaa aatatactcc aaaaattatt aagattattt taataatttt      960
aataatacta tagcctaatg gaatgagcat tgatctgcca gcagagaatt agagggtaa      1020 aattgtgaag atattgtatc cctggctttg aacaaatacc atataacttc tagtgactgc      1080

```
aattctttga tgcagaggca aaatgaagat gatgtcatta ctcatttcac aacaatattg    1140
gagaatgagc taattatctg aaaattacat gaagtattcc aagagaaacc agtatatgga    1200
tcttgtgctg ttcactatgt aaattgtgtg atggtgggtt cagtagttat tgctgtaaat    1260
gttagggcag ggaatatgtt actatgaagt ttattgacag tatactccaa atag          1314
```

<210> SEQ ID NO 132
<211> LENGTH: 9
<212> TYPE: DNA
<213> ORGANISM: Homo sapiens

<400> SEQUENCE: 132 ttagaagtg                                                                9

<210> SEQ ID NO 133
<211> LENGTH: 9
<212> TYPE: DNA
<213> ORGANISM: Homo sapiens

<400> SEQUENCE: 133 ttatgggag                                                                9

US 8,846,578 B2

ZINC FINGER NUCLEASE FOR THE CFTR GENE AND METHODS OF USE THEREOF

The present application is a continuation-in-part of PCT Application PCT/US2009/040617, filed Apr. 15, 2009, which claims benefit of priority to U.S. Provisional Application Ser. No. 61/124,297, filed Apr. 16, 2008, the entire contents of both applications being hereby incorporated by reference.

This invention was made with government support under 1R21HL91808-01 awarded by the National Institutes of Health. The government has certain rights in the invention.

BACKGROUND OF THE INVENTION

I. Field of the Invention

The present invention relates to the fields of molecular biology and medicine. More particularly, it relates to zinc finger nucleases and their use in treating cystic fibrosis.

II. Related Art

A. Cystic Fibrosis

Cystic fibrosis, or CF, is an inherited disease of epithelia-lined organs, including the glands that make mucus and sweat. "Inherited" means that the disease is passed through the genes from parents to children. People who have CF inherit two faulty cystic fibrosis transmembrane conductance regulator (CFTR) genes, one from each parent. CF mostly affects the lungs, pancreas, liver, intestines, sinuses, and sex organs. The symptoms and severity of CF vary from person to person—some people who have CF have serious lung and digestive problems, while others have more mild disease that does not show up until they are adolescents or adults. The symptoms and severity of CF also vary over time.

The disease manifests because if one has CF, mucus becomes thick and sticky. In the lungs, airway innate immunity is impaired, mucus builds up and blocks airways. The buildup of mucus makes it easy for bacteria to grow, which leads to repeated, serious lung infections. Over time, these infections can severely damage lungs. The abnormal secretions also can block ducts in the pancreas. As a result, the digestive enzymes that your pancreas makes cannot reach your small intestine, causing vitamin deficiency and malnutrition because nutrients leave the body unused. It also can cause bulky stools, intestinal gas, a swollen belly from partial or complete intestinal obstruction, and pain or discomfort. CF also causes your sweat to become very salty and, as a result, your body loses large amounts of salt when you sweat. This can upset the balance of minerals in your blood and cause a number of health problem, including dehydration, increased heart rate, tiredness, weakness, decreased blood pressure, heat stroke, and, rarely, death.

As treatments for CF continue to improve, so does life expectancy for those who have the disease. Today, some people who have CF are living into their thirties, forties, fifties, or older. However, CF remains the leading genetic cause of premature death in the United States. As such, improved methods of treating CF are in great need.

B. Zinc Finger Nucleases

Zinc fingers are among the most common DNA binding motifs found in eukaryotes. It is estimated that there are 500 zinc finger proteins encoded by the yeast genome and that perhaps 1% of all mammalian genes encode zinc finger containing proteins. These proteins are classified according to the number and position of the cysteine and histidine residues available for zinc coordination.

The CCHH class, typified by the *Xenopus* transcription factor IIIA, is the largest. These proteins contain two or more fingers in tandem repeats. In contrast, the steroid receptors contain only cysteine residues that form two types of zinc-coordinated structures with four ($C_4$) and five ($C_5$) cysteines. Another class of zinc fingers contains the CCHC fingers. The CCHC fingers, which are found in *Drosophila*, and in mammalian and retroviral proteins, display the consensus sequence C—$N_2$—C—$N_4$—H—$N_4$—C (SEQ ID NO:111). Recently, a novel configuration of CCHC finger, of the C—$N_5$—C—$N_{12}$—H—$N_4$—C (SEQ ID NO:112) type, was found in the neural zinc finger factor/myelin transcription factor family. Finally, several yeast transcription factors such as GAL4 and CHA4 contain an atypical $C_6$ zinc finger structure that coordinates two zinc ions. Zinc fingers are usually found in multiple copies (up to 37) per protein. These copies can be organized in a tandem array, forming a single cluster or multiple clusters, or they can be dispersed throughout the protein.

Zinc finger nucleases (ZFNs) can be used to "rewrite" the sequence of an allele by invoking the homologous recombination machinery to repair the double-strand breaks using a supplied DNA fragment as a template. The homologous recombination machinery searches for homology between the damaged chromosome and the extra-chromosomal fragment and copies the sequence of the fragment between the two broken ends of the chromosome, regardless of whether the fragment contains the original sequence. If the subject is homozygous for the target allele, the efficiency of the technique is reduced since the undamaged copy of the allele may be used as a template for repair instead of the supplied fragment.

Custom-designed ZFNs that combine the non-specific cleavage domain (N) of FokI endonuclease with zinc finger proteins (ZFPs) offer a general way to deliver a site-specific double-strand breaks to the genome, and stimulate local homologous recombination by several orders of magnitude. This makes targeted gene correction or genome editing a viable option in human cells. Since ZFN-encoded plasmids can be used to transiently express ZFNs to target a double-strand break to a specific gene locus in human cells, they offer an excellent way for targeted delivery of the therapeutic genes to a pre-selected chromosomal site. The ZFN-encoded plasmid-based approach has the potential to circumvent problems associated with viral delivery of therapeutic genes. Alternatively, ZFN pairs can be packaged in a variety of viral vectors to improve delivery to specific cell types.

SUMMARY OF THE INVENTION

Thus, in accordance with the present invention, there is provided a zinc three-finger binding domain that targets a nucleotide sequence selected from the group consisting of GTGGAATTA (SEQ ID NO:1) and GAGTGGTTA (SEQ ID NO:2). The zinc three-finger binding domain may comprise a sequence selected from wherein one monomer of said dimer comprises a sequence selected from SEQ ID NOS: 3-5, 6-8, 9-11, 12-14, 15-17, 18-20, 21-23, 24-26, 27-29, 30-32, 33-35 and 36-38 for GTGGAATTA (SEQ ID NO:1) and selected from the group consisting of SEQ ID NOS: SEQ ID NOS: 39-41, 42-44, 45-47, 48-50, 51-53, 54-56, 57-59, 60-62, 63-65, 66-68, 69-71, 72-74, 75-77, 78-80, 81-83, 84-86, 87-89, 90-92, 91-93, 94-96, 97-99, 100-102, 103-105, 106-108, and 109-111 for GAGTGGTTA (SEQ ID NO:2). The zinc three-finger binding domain may be linked to a non-specific nuclease, such as FokI.

In another embodiment, there is provided a zinc three-finger binding domain dimer that targets a double-stranded nucleic acid comprising a first monomer that targets nucleotide sequence GTGGAATTA (SEQ ID NO:1) in one strand and a second monomer that targets nucleotide sequence GAGTGGTTA (SEQ ID NO:2) in the other strand. A particular monomer combination is SEQ ID NO:116 and SEQ ID NO:117. In a particular form, each monomer of said zinc three-finger binding domain dimer is linked to a non-specific nuclease monomer, such as FokI. The resulting zinc finger nuclease may be homo- or heterodimeric.

In yet another embodiment, there is provided a vector comprising a nucleic acid segment encoding a zinc three-finger binding domain that targets a nucleotide sequence selected from the group consisting of GTGGAATTA (SEQ ID NO:1) and GAGTGGTTA (SEQ ID NO:2), said nucleic acid under the control of a promoter operable in a eukaryotic cell. The vector may further comprise a selectable or screenable marker and or an origin of replication. The vector may be a viral vector, such as an adenoviral vector, an adeno-associated viral vector, a pox viral vector, a herpes viral vector, a retroviral vector, a lentiviral vector, including an integrase defective lentivirus vector. The vector may comprises two nucleic acid segements, each encoding a zinc three-finger binding domain, one that targets GTGGAATTA (SEQ ID NO:1) and one that targets GAGTGGTTA (SEQ ID NO:2). In such situations, each of said nucleic acid segments may be under the control of a separate promoter active in said eukaryotic cell, or both of said nucleic acid segments may be under the control of a the same promoter. The nucleic acid segments may be separated by a transcription termination signal, separated by an internal ribosome entry site, or by a picornavirus T2A sequence.

In still yet another embodiment, there is provided a method of promoting recombination within a CTFR gene in a human cell comprising contacting said cell with a first zinc three-finger binding domain that targets a nucleotide sequence GTGGAATTA (SEQ ID NO:1) and a second zinc three-finger binding domain that targets a nucleotide sequence GAGTGGTTA (SEQ ID NO:2), wherein each of said first and second zinc three-finger binding domains are linked to a non-specific nuclease. The zinc three-finger binding domain may comprise a sequence selected from SEQ ID NOS: 3-5, 6-8, 9-11, 12-14, 15-17, 18-20, 21-23, 24-26, 27-29, 30-32, 33-35 and 36-38 for GTGGAATTA (SEQ ID NO:1) and selected from the group consisting of SEQ ID NOS: 39-41, 42-44, 45-47, 48-50, 51-53, 54-56, 57-59, 60-62, 63-65, 66-68, 69-71, 72-74, 75-77, 78-80, 81-83, 84-86, 87-89, 90-92, 91-93, 94-96, 97-99, 100-102, 103-105, 106-108, and 109-111 for GAGTGGTTA (SEQ ID NO:2). The human cell may be a lung epithelial cell, and intestinal epithelial cell, a biliary duct epithelial cell, a gall bladder epithelial cell or pancreatic epithelial cell. The lung cell or pancreatic cell may comprise a CFTR gene with a ΔF508 mutation.

The lung epithelial cell or pancreatic cell may be located in a living human subject, and contacting may comprise administering said first and second zinc three-finger binding domains to lung or pancreatic tissue of said subject. The administration to lung tissue may comprise inhalation or topical instillation. The administration to pancreatic tissue may comprise injection. Contacting may comprise administering to said subject an expression vector comprising a first nucleic acid segment encoding a first zinc three-finger binding domain that targets GTGGAATTA (SEQ ID NO:1) and a second nucleic acid segment encoding a second zinc three-finger binding domain that targets GAGTGGTTA (SEQ ID NO:2), said nucleic acids under the control of one or more promoters operable in a eukaryotic cell. The vector may be a viral vector, such as an adenoviral vector, an adeno-associated viral vector, a pox viral vector, a herpes viral vector, a retroviral vector, a lentiviral vector, including an integrase-defective lentiviral vector. The nucleic acid segments may be under the control of a separate promoter active in said eukaryotic cell or under the control of a the same promoter. The nucleic acid segments may be separated by a transcription termination signal and/or an internal ribosome entry site and/or a picornavirus T2A sequence.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions and kits of the invention can be used to achieve methods of the invention.

Throughout this application, the term "about" is used to indicate that a value includes the inherent variation of error for the device, the method being employed to determine the value, or the variation that exists among the study subjects.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-C—OPEN Method for Constructing Zinc-finger Arrays. (FIG. 1A) Schematic overview of OPEN zinc-finger pool construction. Zinc-finger domains are represented as spheres and their associated 3 bp subsites as rectangles. The randomized finger in the library is multi-colored. The strategy for making finger pools for the middle finger in a three-finger domain is illustrated. Note that finger pools for amino- or carboxy-terminal fingers were obtained by building additional libraries in which finger 1 or finger 3 were randomized, respectively. Details in the text and Experimental Procedures. (FIG. 1B) Schematic overview of OPEN selections. Zinc-fingers and associated subsites represented as in FIG. 1A. Details in Experimental Procedures. (FIG. 1C) Schematic of the bacterial two-hybrid (B2H) system. ZFA=zinc-finger array.

(FIG. 2A) Map of sites in EGFP targeted by OPEN selections. (FIG. 2B) DNA-binding activities of zinc-finger arrays made by modular assembly (MA) and OPEN assessed by quantitative B2H assays. The source of modules used to construct modularly assembled arrays is indicated as Barbas, Sangamo, or Toolgen. Mean fold-activation values (colored bars) and standard deviations (error bars) obtained from three independent assays are shown. (FIG. 2C) EGFP-disruption assay for testing ZFN activities in human cells. (FIG. 2D) Modularly assembled and OPEN ZFN activities assessed using the EGFP-disruption assay. Error bars represent standard deviations. Single and double asterisks indicate p values <0.05 and <0.01, respectively.

FIGS. 3A-G—Highly efficient mutagenesis of endogenous human and plant genes by OPEN ZFNs. (FIG. 3A) Map of sites in human VEGF-A, HoxB13, and CFTR targeted by OPEN selections. (FIG. 3B) Schematic of CEL I assay for assaying ZFN-induced mutations. (FIGS. 3C-D) Mutation of the endogenous human VEGF-A promoter (FIG. 3C) and HoxB13 gene (FIG. 3D) by OPEN ZFNs. Colored arrows indicate expected CEL I digestion products. Images shown are from representative experiments. (FIGS. 3E-G) Sequences of (FIG. 3E) HoxB13 alleles from human 293 cells transfected with HX587 ZFN pair B (wild-type=SEQ ID NO:120), (FIG. 3F) CFTR alleles from human K562 cells transfected with CF877 ZFNs (wild-type=SEQ ID NO:121), and (FIG. 3G) SuRA alleles from tobacco plants transfected with SR2163 ZFNs (SuRA=SEQ ID NO:122; SuRB=SEQ ID NO:123; and SuRA with deletion=SEQ ID NO:124). Numbers of each allele identified are shown in parentheses. ZFN recognition sites are in bold orange print.

(FIG. 4A) Gene targeting of human VEGF-A and IL2Rγ genes by homologous recombination with an exogenous "donor construct." Arrows indicate primers used for limited-cycle PCR/restriction digest assay described in the text. (FIG. 4B) OPEN ZFNs induce efficient gene targeting at the VEGF-A promoter in human 293 cells. Top part shows representative gel images from limited-cycle PCR/restriction digest assays and bottom part shows gene targeting frequency means (colored bars) and standard errors (error bars) from multiple experiments. (FIG. 4C) OPEN VEGF-A and Sangamo IL2Rγ ZFNs induce efficient gene targeting at endogenous genes in human K562 cells. Data presented as in FIG. 4B. (FIG. 4D) Gene targeting efficiencies of OPEN VEGF-A ZFNs assessed nine days post-transfection by limited-cycle PCR/restriction digest and Southern blot assays. (FIG. 4E) Comparison of PCR-based and Southern blot methods for assaying gene targeting efficiencies. Dotted red line represents where data points would fall if the two methods were perfectly concordant. (FIG. 4F) G2 arrest by vinblastine enhances gene targeting by OPEN VEGF-A and Sangamo IL2Rγ ZFNs. Assays performed four days post-transfection. Data presented as in FIG. 4B. (FIGS. 4G-I) Sequences of alleles sequenced from human K562 cells transfected with (FIG. 4G) VF2468 ZFNs and donor (wild-type=SEQ ID NO:125; GT events=SEQ ID NO:126; and GT+insertions=SEQ ID NO:127), (FIG. 4H) VF2471 ZFNs and donor (wild-type=SEQ ID NO:128; and GT events=SEQ ID NO:126), and (FIG. 4I) IL2Rγ ZFNs and donor (wild-type=SEQ ID NO:129). Data are presented as in FIG. 3E. (FIG. 4J) Toxicities of OPEN VEGF-A and Sangamo IL2Rγ ZFNs in human K562 cells. Means and standard deviations of GFP (green bars) and gene targeting ratios (purple bars) are shown. Single and double asterisks indicate p values <0.05 and <0.01, respectively. (FIG. 4K) Gene targeting efficiencies of OPEN VEGF-A and Sangamo IL2Rγ ZFNs in toxicity experiments 25 of FIG. 4J. Means and standard deviations are shown of PCR-based assays performed four days post-transfection.

FIGS. 5A-B—OPEN ZFNs induce permanent alterations of multiple gene copies in human cells. (FIG. 5A) OPEN ZFNs can induce stable alteration of as many as four copies of the VEGF-A gene in a single human cell. Altered clonal cells were genotyped using the limited-cycle PCR/restriction digest assay. Representative results from each genotype observed are shown in the bottom panels. Additional details in the text. (FIG. 5B) FISH analysis of wild-type K562 cells and three K562 cell lines (modified by VF2468 ZFNs) in which all copies of the VEGF-A gene have undergone a gene targeting event. FISH was performed with a probe for VEGF-A (red) and a control probe for 14q which is present in two copies per cell (green).

FIG. 8—Diagram of a ZFN pair package in an adenovirus vector. ZFN pairs are packaged in a single adenoviral vector. The construct is driven by the CMV promoter. Heterodimeric FOK1 nucleases are employed. The two ZFN expression cassettes are joined by an intervening picornavirus T2A sequence. An mCherry reporter cassette is packaged in the E3 region of the vector.

FIG. 10—Sequence of the 2 kb region around the ΔF508 mutation in the CFTR gene. (SEQ ID NO. 131) Sequence in exon 10 region is in bold. CTT (outlined font) is absent in ΔF508 individuals. Lower case is the 790 ZFN binding sites. Double underline is the 877 ZFN binding sites. TGTCA 5 by insertion between TGA/TGA of 877 spacer TGATGA to introduce unique restriction site BspH1. Repeat regions are in italics.

FIGS. 11A-B—(FIG. 11A) Depiction of an adenoviral vector expressing the ZFN pair targeting the CF877 site as a single expression cassette with an intervening picornavirus T2A sequence. (FIG. 11B) The frequency of NHEJ increased in a dose-dependent manner from ~10% at MOI of 50 to ~29% at MOI of 250 in CFBE41o-cells.

DETAILED DESCRIPTION OF THE INVENTION

Figure 2A:
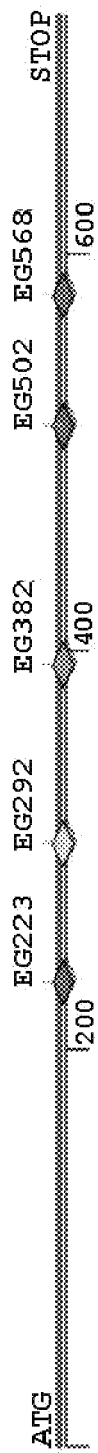
FIGS. 2A-D—OPEN ZFNs Engineered to Cleave EGFP Reporter Gene Sequences.

Engineered zinc-finger nucleases (ZFNs) are broadly applicable tools that have been shown to mediate highly efficient genome modification in Drosophila, C. elegans, plant, and human cells (Alwin et al., 2005; Beumer et al., 2006; Bibikova et al., 2003; Bibikova et al., 2002; Cornu et al., 2008; Lloyd et al., 2005; Lombardo et al., 2007; Miller et al., 2007; Moehle et al., 2007; Morton et al., 2006; Porteus and Baltimore, 2003; Szczepek et al., 2007; Urnov et al., 2005; Wright et al., 2005). ZFNs function as dimers with each monomer consisting of a non-specific cleavage domain from the FokI endonuclease fused to an array of artificial zinc-fingers engineered to bind a target DNA sequence of interest (Durai et al., 2005; Porteus and Carroll, 2005). Individual zinc-finger domains bind to 3 bp subsites, and arrays of fingers can recognize extended 9 or 12 bp sequence targets. ZFNs introduce site-specific, double-stranded DNA breaks (DSBs) that stimulate either highly efficient gene targeting by homologous recombination with an exogenously introduced template (Jasin, 1996) or gene mutation by error-prone non-homologous endjoining (NHEJ). Absolute rates of ZFN-enhanced gene modification can be as high as 50% (Lombardo et al., 2007).

Lack of access to a rapid and effective zinc-finger engineering platform has significantly limited the efforts of academic scientists to use and further develop ZFN technology. It is striking that in the five years since ZFNs were first shown to work in human cells, not one academic group has successfully made ZFNs for even a single endogenous mammalian or plant gene (although endogenous Drosophila genes have been modified (Beumer et al., 2006; Bibikova et al., 2003)). The proprietary zinc-finger engineering platform of the company Sangamo Biosciences is not freely available to academic scientists and thus remains a "black box" with respect to both its implementation and efficacy (Scott, 2005). The published literature describes many different publicly available zinc-finger engineering methods which can be broadly grouped into two general categories: (1) "modular assembly" methods in which individual fingers with pre-characterized specificities are joined together (Bae et al., 2003; Beerli and Barbas, 2002; Liu et al., 2002; Mandell and Barbas, 2006; Segal, 2002; Segal et al., 2003) or (2) labor-intensive selection-based methods which require multiple large randomized libraries (Greisman and Pabo, 1997; Hurt et al., 2003; Isalan and Choo, 2001; Isalan et al., 2001).

Although modular assembly is easy to perform, the inventors have recently shown that its overall efficacy for making functional ZFN pairs is predicted to be less than 6% (Ramirez et al., 2008) and that even when "successful" it yields ZFNs with low activities and/or high toxicities (Cornu et al., 2008; Pruett-Miller et al., 2008). Selection-based methods require construction and interrogation of multiple, large randomized libraries (typically >$10^8$ in size) and therefore remain intractable for all but a small number of academic labs. Thus, unlike other broadly accessible technologies like RNA interference, ZFN-induced genome modification has been utilized by very few academic scientists.

The inventors describe here the development and validation of OPEN (Oligomerized Pool ENgineering), a facile and robust platform for engineering customized zinc-finger arrays. OPEN is enabled by the construction of a large archive of zinc-finger pools designed to bind various DNA sequences. This archive was constructed by the Zinc Finger Consortium, a group of academic laboratories committed to the development of engineered zinc-finger technology (world-wide-web at zincfingers.org). They employed OPEN to rapidly and successfully engineer a large set of zinc-finger arrays: 269 unique multi-finger arrays for 34 different target sites. The inventors then used a subset of these arrays to construct 37 active ZFN pairs for 11 different target sites located within three endogenous human genes (VEGF-A, HoxB13, CFTR), an endogenous plant gene (tobacco SuRA), and the EGFP reporter gene. Using these ZFNs, they show that: (i) OPEN is significantly more robust than the existing modular assembly engineering method, (ii) OPEN ZFNs induce stable genome modifications with high efficiency (absolute rates ranging from 1-50% and with changes in as many as four alleles in a single cell), and (iii) OPEN ZFNs possess activities and toxicities comparable to those of an extensively optimized ZFN pair previously reported.

Moreover, the inventors have identified specific ZFNs that are designed to target the cystic fibrosis transmembrane conductance regulator (CFTR) gene, thereby providing a potential therapy for cystic fibrosis. In the present embodiment the focus is on modification of exon 10 of the CFTR gene, site of the most common human disease associated mutation, ΔF508, cause by a 3 bp deletion. Delivery methods and vectors for expression ZFNs are provided that enhance the homologous recombination within the CFTR gene. These and other aspects of the invention are described further below.

I. ZINC FINGER NUCLEASES

A. Zinc Finger Proteins

Zinc fingers are part of a large superfamily of protein domains that can bind to DNA. A zinc finger consists of two antiparallel β strands, and an α helix. The zinc ion is crucial for the stability of this domain type—in the absence of the metal ion the domain unfolds as it is too small to have a hydrophobic core. One very well explored subset of zinc-fingers (the $C_2H_2$ class) comprises a pair of cysteine residues in the beta strands and two histidine residues in the alpha helix which are responsible for binding a zinc ion. The two other classes of zinc finger proteins are the $C_4$ and $C_6$ classes. Zinc fingers are important in regulation because when interacted with DNA and zinc ion, they provide a unique structural motif for DNA-binding proteins.

The structure of each individual finger is highly conserved and consists of about 30 amino acid residues, constructed as a ββα fold and held together by the zinc ion. The α-helix occurs at the C-terminal part of the finger, while the β-sheet occurs at the N-terminal part. This is most useful in tanscription process. The consensus sequence of a single finger is:

(SEQ ID NO: 113)
Cys-$X_{2-4}$-Cys-$X_3$-Phe-$X_5$-Leu-$X_2$-His-X3-His

Many transcription factors (such as Zif268), regulatory proteins, and other proteins that interact with DNA contain zinc fingers. These proteins typically interact with the major groove along the double helix of DNA in which case the zinc fingers are arranged around the DNA strand in such a way that the α-helix of each finger contacts the DNA, forming an almost continuous stretch of α-helices around the DNA molecule. Some primary neuron-specific transcriptional regulator that may be involved in mediating early neural development are also zinc finger-based.

The binding specificity for 3-4 base pairs is conferred by a short stretch of amino acid residues in the α-helix. The primary position of the amino acid residues within the α-helix interacting with the DNA are at positions −1, 3 and 6 relative to the first amino acid residue of the α-helix. Other amino acid positions can also influence binding specificity by assisting amino acid residues to bind a specific base or by contacting a fourth base in the opposite strand, causing target-site overlap.

B. ZFNs

Zinc finger nucleases (ZFNs) are protein chimera comprised of a zinc finger-based DNA-binding domain and a DNA-cleavage domain. They are able to introduce double-strand breaks (DSB; breaks at the same or very close points in both strands of a double-stranded DNA molecule) at specific locations within a DNA molecule which may subsequently be used to disable a specific allele or even rewrite the code it contains. Inventor of the zinc finger nuclease is Srinivasan Chandrasegaran from Johns Hopkins University in Baltimore, Md. ZFNs are undergoing development for use in gene therapy and research applications.

The DNA-binding domain of a ZFN may be composed of two to six zinc fingers due to their supposed modularity (appositeness to be used interchangeably). Each zinc finger motif is typically considered to recognise and bind to a three-base pair sequence and as such, a protein including more zinc fingers targets a longer sequence and therefore has a greater specificity and affinity to the target site. Depending upon the required specifications of the end-product, the included zinc fingers may be selected via a parallel, sequential or bipartite technique or through an in vitro cell-based technique.

The non-specific nuclease domain of FokI is functionally independent of its natural DNA-binding domain and is therefore employed in the construction of ZFNs. Since the domain must dimerise to accomplish a double-strand break it is necessary that a nuclease is also bound to the opposite strand by virtue of another ZFN molecule bound to its target sequence as shown in the diagram. The two target sites need not be the same, so long as ZFNs targeting both sites are present. In order to form a dimer, two ZFN molecules must meet with their respective recognition sites not less than 4-6 base pairs apart but also not so far apart that they may not dimerise. While one ZFN molecule binds its target sequence on one strand, another ZFN molecule binds its target sequence on the opposite strand, as shown in the diagram. The nuclease domains dimerise and each cleaves its own strand, producing a DSB. FokI can be employed as a homo- or a heterodimer. The advantage of the heterodimer is that it may reduce off target effects (Miller et al., 2007).

ZFNs can be used to disable dominant mutations in heterozygous individuals by producing DSBs in the mutant allele which will, in the absence of a homologous template, be repaired by non-homologous end-joining (NHEJ). NHEJ repairs double-strand breaks by joining the two ends together and usually produces no mutations, provided that the cut is clean and uncomplicated. In some instances however, the repair will be imperfect, resulting in deletion or insertion of base-pairs, producing frame-shift and preventing the production of the harmful protein.

C. Expression Systems for ZFNs

In particular embodiments, the ZFN may advantageously be delivered to a host cell or subject using a recombinant vector encoding the ZFN. The term "recombinant" generally refers to a polypeptide produced from a nucleic acid molecule that has been manipulated in vitro or that is the replicated product of such a molecule.

The nucleic acid segments used in the present invention, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (Sambrook et al., 1989; Ausubel et al., 1996, both incorporated herein by reference). In addition to encoding a modified polypeptide such as modified gelonin, a vector may encode non-modified polypeptide sequences such as a tag or targetting molecule. Useful vectors encoding such fusion proteins include pIN vectors (Inouye et al., 1985), vectors encoding a stretch of histidines, and pGEX vectors, for use in generating glutathione S-transferase (GST) soluble fusion proteins for later purification and separation or cleavage. A targetting molecule is one that directs the modified polypeptide to a particular organ, tissue, cell, or other location in a subject's body.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. No. 4,683,202, U.S. Pat. No. 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it may be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous. The identity of tissue-specific promoters or elements, as well as assays to characterize their activity, is well known to those of skill in the art.

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5'-methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference). The picornavirus-derived, self-cleaving 2A peptide, designated T2A, allows for the efficient translation of multiple cistrons and therefore is an additional element that can be employed in multi-cistronic messages.

3. Multiple Cloning Sites

Vectors can include a multiple cloning site (MCS), which is a nucleic acid region that contains multiple restriction enzyme sites, any of which can be used in conjunction with standard recombinant technology to digest the vector. (See Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression. (See Chandler et al., 1997, incorporated herein by reference.)

5. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and/or to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

6. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

7. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

8. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

9. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid, such as a modified protein-encoding sequence, is transferred or introduced into the host cell. A transformed cell includes the primary subject cell and its progeny.

Host cells may be derived from prokaryotes or eukaryotes, including yeast cells, insect cells, and mammalian cells, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials (world-wide-web at atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla, Calif.). Alternatively, bacterial cells such as E. coli LE392 could be used as host cells for phage viruses. Appropriate yeast cells include Saccharomyces cerevisiae, Saccharomyces pombe, and Pichia pastoris.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

10. Commercial Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

In addition to the disclosed expression systems of the invention, other examples of expression systems include STRATAGENE®'S COMPLETE CONTROL™ Inducible Mammalian Expression System, which involves a synthetic ecdysone-inducible receptor, or its pET Expression System, an E. coli expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the Pichia methanolica Expression System, which is designed for high-level production of recombinant proteins in the methylotrophic yeast Pichia methanolica. One of skill in the art would know how to express a vector, such as an expression construct, to produce a nucleic acid sequence or its cognate polypeptide, protein, or peptide.

11. Viral Vectors

There are a number of ways in which expression vectors may be introduced into cells. In certain embodiments of the invention, the expression vector comprises a virus or engineered vector derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubinstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubinstein, 1988; Temin, 1986).

The retroviruses are a group of single-stranded RNA viruses characterized by an ability to convert their RNA to double-stranded DNA in infected cells; they can also be used as vectors. Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

12. Methods of Gene Transfer

Suitable methods for nucleic acid delivery to effect expression of compositions of the present invention are believed to include virtually any method by which a nucleic acid (e.g., DNA, including viral and nonviral vectors) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981, 274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

II. CYSTIC FIBROSIS AND CFTR

A. Cystic Fibrosis (CF)

Cystic Fibrosis (also known as CF) is a hereditary disease affecting the exocrine (mucus) glands of the lungs, liver, pancreas, and intestines, causing progressive disability due to multisystem failure. Abnormally thick mucus results in frequent lung infections. Diminished secretion of pancreatic enzymes is the main cause of poor growth, greasy stools, and deficiency in fat-soluble vitamins. Males can be infertile due to the condition congenital bilateral absence of the vas deferens. Often, symptoms of CF appear in infancy and childhood. Meconium ileus is a typical finding in newborn babies with CF.

There is no known cure for CF, and most individuals with cystic fibrosis die young: many in their 20's and 30's from lung failure. The predicted median age of survival for a person with CF is 37 years. However, with the continuous introduction of many new treatments, the life expectancy of a person with CF is increasing to ages as high as 40 or 50. Lung transplantation is often necessary as CF worsens.

Cystic fibrosis is one of the most common life-shortening genetic diseases. In the United States, 1 in 4,000 children is born with CF. It is most common among western European populations; one in twenty-two people of Mediterranean descent is a carrier of one gene for CF, making it the most common genetic disease in these populations. In 1997, about 1 in 3,300 caucasian children in the United States was born with cystic fibrosis. In contrast, only 1 in 15,000 African American children suffered from cystic fibrosis, and in Asian Americans the rate was even lower at 1 in 32,000.

CF is caused by a mutation in the gene, cystic fibrosis transmembrane conductance regulator (CFTR). The product of this gene is a chloride ion channel important in creating sweat, digestive juices, and mucus. Although most people without CF have two working copies (alleles) of the CFTR gene, only one is needed to prevent cystic fibrosis. CF develops when neither allele can produce a functional CFTR protein. Therefore, CF is considered an autosomal recessive disease.

Cystic fibrosis may be diagnosed by many different categories of testing including those such as, newborn screening, sweat testing, or genetic testing. As of 2006 in the United States, 10 percent of cases are diagnosed shortly after birth as part of newborn screening programs. The newborn screen initially measures for raised blood concentration of immunoreactive trypsinogen. Infants with an abnormal newborn screen need a sweat test in order to confirm the CF diagnosis. Trypsinogen levels can be increased in individuals who have a single mutated copy of the CFTR gene (carriers) or, in rare instances, even in individuals with two normal copies of the CFTR gene. Due to these false positives, CF screening in newborns is somewhat controversial. Most states and countries do not screen for CF routinely at birth. Therefore, most individuals are diagnosed after symptoms prompt an evaluation for cystic fibrosis. The most commonly-used form of testing is the sweat test. Sweat-testing involves application of a medication that stimulates sweating (pilocarpine) to one electrode of an apparatus and running electric current to a separate electrode on the skin. This process, called iontophoresis, causes sweating; the sweat is then collected on filter paper or in a capillary tube and analyzed for abnormal amounts of sodium and chloride. People with CF have increased amounts of sodium and chloride in their sweat. CF can also be diagnosed by identification of mutations in the CFTR gene.

A multitude of tests are used to identify complications of CF and to monitor disease progression. X-rays and CAT scans are used to examine the lungs for signs of damage or infection. Examination of the sputum under a microscope is used to identify which bacteria are causing infection so that effective antibiotics can be given. Pulmonary function tests measure how well the lungs are functioning, and are used to measure the need for and response to antibiotic therapy. Blood tests can identify liver abnormalities, vitamin deficiencies, and the onset of diabetes. DEXA scans can screen for osteoporosis and testing for fecal elastase can help diagnose insufficient digestive enzymes.

As discussed above, cystic fibrosis occurs when there is a mutation in both copies of the CFTR gene. The protein created by this gene is anchored to the outer membrane of cells in the sweat glands, lungs, pancreas, and other affected organs. The protein spans this membrane and acts as a channel connecting the inner part of the cell (cytoplasm) to the surrounding fluid. In the airway this channel is primarily responsible for controlling the movement of chloride from inside to outside of the cell, however in the sweat ducts it facilitates the movement of chloride from the sweat into the cytoplasm. When the CFTR protein does not work, chloride is trapped inside the cells in the airway and outside in the skin. Because chloride is negatively charged, positively charged ions cross into the cell because they are affected by the electrical attraction of the chloride ions. Sodium is the most common ion in the extracellular space and the combination of sodium and chloride creates the salt, which is lost in high amounts in the sweat of individuals with CF. This lost salt forms the basis for the sweat test.

How this malfunction of cells in cystic fibrosis causes the clinical manifestations of CF is not well understood. One theory suggests that the lack of chloride exodus through the CFTR protein leads to the accumulation of more viscous, nutrient-rich mucus in the lungs that allows bacteria to hide from the body's immune system. Another theory proposes that the CFTR protein failure leads to a paradoxical increase in sodium and chloride uptake, which, by leading to increased water reabsorption, creates dehydrated and thick mucus. Yet another theory focuses on abnormal chloride movement out of the cell, which also leads to dehydration of mucus, pancreatic secretions, biliary secretions, etc. These theories all support the observation that the majority of the damage in CF is due to blockage of the narrow passages of affected organs with thickened secretions. These blockages lead to remodeling and infection in the lung, damage by accumulated digestive enzymes in the pancreas, blockage of the intestines by thick faeces, etc.

B. CFTR

The CFTR gene is found at the q31.2 locus of chromosome 7, is 230,000 base pairs long, and creates a protein that is 1,480 amino acids long. The most common mutation, $\Delta$F508 is a deletion ($\Delta$) of three nucleotides in exon 10 that results in a loss of the amino acid phenylalanine (F) at the 508th (508) position on the protein. This mutation accounts for two-thirds of CF cases worldwide and 90% of cases in the United States; however, there are over 1,400 other mutations that can produce CF.

There are several mechanisms by which these mutations cause problems with the CFTR protein. $\Delta$F508, for instance, creates a protein that does not fold normally and is degraded by the cell. Several mutations, which are common in the Ashkenazi Jewish population, result in proteins that are too short because production is ended prematurely. Less common mutations produce proteins that do not use energy normally, do not allow chloride to cross the membrane appropriately, or are degraded at a faster rate than normal. Mutations may also lead to fewer copies of the CFTR protein being produced.

Structurally, CFTR is a type of gene known as an ABC gene. Its protein possesses two ATP-hydrolyzing domains which allows the protein to use energy in the form of ATP. It also contains two domains comprising 6 alpha helices apiece, which allow the protein to cross the cell membrane. A regulatory binding site on the protein allows activation by phosphorylation, mainly by cAMP-dependent protein kinase. The carboxyl terminal of the protein is anchored to the cytoskeleton by a PDZ domain interaction.

Reference to the human CFTR sequence is made by way of Genbank Accession No. NM_000492 (SEQ ID NO:114 and 115) as well as SEQ ID NOS:1-2.

III. TREATMENT OF CF WITH ZFNS

A. ZFNs Targeting $\Delta$508F

In one embodiment, the present invention provides for the treatment of CF using particular ZFNs identified herein. These ZFNs target a region of the CFTR that is adjacent to (w/1100 base of) the $\Delta$508F mutation. Reference to exon 10 of the CFTR sequence is made in FIG. 10.

B. Pharmaceutical Compositions and Routes of Administration

Pharmaceutical compositions of the present invention comprise an effective amount of one or more ZFNs dissolved or dispersed in a pharmaceutically acceptable carrier. The phrases "pharmaceutical or pharmacologically acceptable" refer to molecular entities and compositions that do not produce an adverse, allergic or other untoward reaction when administered to an animal, such as, for example, a human, as appropriate. The preparation of a pharmaceutical composition that contains at least one ZFN, and optionally an additional active ingredient, will be known to those of skill in the art in light of the present disclosure, as exemplified by Remington's Pharmaceutical Sciences, 18th Ed. Mack Printing Company (1990), incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The ZFNs may be admixed with different types of carriers depending on how they are be administered. The present invention can be administered buccally, intravenously, intradermally, transdermally, intrathecally, intraarterially, intraperitoneally, intranasally, intravaginally, intrarectally, topically, intramuscularly, intratumorally, into tumor vasculature, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., nanoparticles, liposomes), or by other method or any combination of the forgoing as would be known to one of ordinary skill in the art (see, for example, Remington's Pharmaceutical Sciences, 18th Ed. Mack Printing Company, 1990, incorporated herein by reference). In particular, the ZFNs is formulated into a syringeable composition for use in intravenous administration.

The ZFNs may be formulated into a composition in a free base, neutral or salt form or ester. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric, fumaric, or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective.

Further in accordance with the present invention, the composition of the present invention suitable for administration is provided in a pharmaceutically acceptable carrier with or without an inert diluent. A carrier should be assimilable and includes liquid, semi-solid, i.e., pastes, or solid carriers. Except insofar as any conventional media, agent, diluent or carrier is detrimental to the recipient or to the therapeutic effectiveness of the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include ZFNs, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally-occurring or synthetic (i.e., designed or produced by man). Lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof.

One of ordinary skill in the art would be familiar with the range of techniques that can be employed for dispersing a composition in a lipid vehicle. For example, the ZFNs may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, ZFNs pharmaceutical compositions may comprise, for example, at least about 0.1% of the ZFN, about 0.5% of the ZFN, or about 1.0% of the ZFN. In other embodiments, the ZFN may comprise between about 2% to about 75% of the weight of the unit, or between about 25% to about 60%, for example, and any range derivable therein. Naturally, the amount of the ZFN in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose of a ZFN may also comprise from about 0.1 microgram/kg/body weight, about 0.2 microgram/kg/body weight, about 0.5 microgram/kg/body weight, about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In particular embodiments of the present invention, the ZFNs are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

For oral administration, the compositions of the present invention may alternatively be incorporated with one or more excipients in the form of a mouthwash, dentifrice, buccal tablet, oral spray, gel or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet, gel or solution form that may be placed under the tongue, along the gum line, brushed on to teeth surfaces, or otherwise dissolved in the mouth. U.S. Pat. Nos. 6,074,674 and 6,270,750, both incorporated by reference, describe topical, sustained release compositions for periodontal procedures.

In further embodiments, ZFNs may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally. Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

Of particular relevance to the present invention is aerosol administration, also known as inhalation therapy, is the administration of ZFNs by an appropriate device that permits inhalation and absorption into the patient's lungs. Aerosol administration in itself is generally a safe practice, as long as the health care provider or user is well educated in its use. It is contraindicated in conditions where complete obstruction of the airway is present, as the administration route is completely blocked. Aerosol drug administration, or in some cases nebulized drug therapy, disperses drugs into the lungs or bronchial airways in the form of tiny droplets—often bound to water, oxygen, or another gaseous substance. Drugs are generally delivered by two means. The first is via a device called a nebulizer. The nebulizer is a mechanical pump (of which there are many types) that produces a fine mist in which the drug is dispersed via an appropriate nebulizer-compatible face mask. This fine mist is inhaled deep into the lungs for maximum effect. The second method of delivery is via a hand-held, nebulized aerosol device. These devices, also known as "puffers," use the effects of a pressurized gas to create and disperse the drug into a fine mist or spray, which is then inhaled. Both methods of aerosol inhalation are very effective when used correctly.

C. Combination Therapies

In some aspects of the present invention, other agents may be used in combination with ZFNs to provide a more effective therapy for CF. More generally, these agents would be provided in a combined amount to produce or increase any of the effects discussed herein. This process may involve contacting a subject with both agents at the same time. This may be achieved by contacting the cell or subject with a single composition or pharmacological formulation that includes both agents, or by contacting the cell or subject with two distinct compositions or formulations, at the same time, wherein one composition includes the intracellular Cathepsin L inhibitor and the other includes the second agent.

Alternatively, one agent may precede or follow the other by intervals ranging from minutes to weeks. In embodiments where the agents are applied separately to the cell or subject, one would generally ensure that a significant period of time did not expire between the time of each delivery, such that the agents would still be able to exert an advantageously combined effect on the cell or subject. In such instances, it is contemplated that one may contact the cell with both modalities within about 12-24 h of each other and, more preferably, within about 6-12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

Various combinations may be employed, the ZFN is "A" and the other agent is "B":

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

Administration protocols and formulation of such agents will generally follow those of standard pharmaceutical drugs, as discussed further below.

Many CF patients are on one or more antibiotics at all times, even when they are considered healthy, to suppress the infection as much as possible. Antibiotics are absolutely necessary whenever pneumonia is suspected or there has been a noticeable decline in lung function. Antibiotics are usually chosen based on the results of a sputum analysis and the patient's past response. Many bacteria common in cystic fibrosis are resistant to multiple antibiotics and require weeks of treatment with intravenous antibiotics such as vancomycin, tobramycin, meropenem, ciprofloxacin, and piperacillin. This prolonged therapy often necessitates hospitalization and insertion of a more permanent IV such as a PICC line or Port-a-Cath. Inhaled therapy with antibiotics such as tobramycin and colistin is often given for months at a time in order to improve lung function by impeding the growth of colonized bacteria. Inhaled therapy with the antibiotic aztreonam is also being developed and clinical trials have shown great promise. Oral antibiotics such as ciprofloxacin or azithromycin are given to help prevent infection or to control ongoing infection. Some individuals spend years between hospitalizations for antibiotics, whereas others require several antibiotic treatments each year.

Several common antibiotics such as tobramycin and vancomycin can cause hearing loss, damage to the balance system in the inner ear or kidney problems with long-term use. In order to prevent these side-effects, the amount of antibiotics in the blood are routinely measured and adjusted accordingly.

Several mechanical techniques are used to dislodge sputum and encourage its expectoration. In the hospital setting, physical therapy is utilized; a therapist percusses an individual's chest with his or her hands several times a day. Devices that recreate this percussive therapy include the ThAIRapy Vest and the intrapulmonary percussive ventilator (IPV). Newer methods such as Biphasic Cuirass Ventilation, and associated clearance mode available in such devices, now integrate a cough assistance phase, as well as a vibration phase for dislodging secretions. Biphasic Cuirass Ventilation is also shown to provide a bridge to transplantation. These are portable and adapted for home use. Physiotherapy is essential to help manage an individuals chest on a long term basis, and can also teach techniques for the older child and teenager to manage themselves at home. Aerobic exercise is of great benefit to people with cystic fibrosis. Not only does exercise increase sputum clearance but it also improves cardiovascular and overall health.

Aerosolized medications that help loosen secretions include dornase alfa and hypertonic saline. Dornase is a recombinant human deoxyribonuclease, which breaks down DNA in the sputum, thus decreasing its viscosity. N-Acetylcysteine may also decrease sputum viscosity, but research and experience have shown its benefits to be minimal. Albuterol and ipratropium bromide are inhaled to increase the size of the small airways by relaxing the surrounding muscles.

As lung disease worsens, breathing support from machines may become necessary. Individuals with CF may need to wear special masks at night that help push air into their lungs. These machines, known as bilevel positive airway pressure (BiPAP) ventilators, help prevent low blood oxygen levels during sleep. BiPAP may also be used during physical therapy to improve sputum clearance. During severe illness, people with CF may need to have a tube placed in their throats (a procedure known as a tracheostomy) and their breathing supported by a ventilator.

Lung transplantation often becomes necessary for individuals with cystic fibrosis as lung function and exercise tolerance declines. Although single lung transplantation is possible in other diseases, individuals with CF must have both lungs replaced because the remaining lung would contain bacteria that could infect the transplanted lung. A pancreatic or liver transplant may be performed at the same time in order to alleviate liver disease and/or diabetes. Lung transplantation is considered when lung function approaches a point where it threatens survival or requires assistance from mechanical devices. This point is typically when lung function declines to approximately 20 to 30 percent, however the there is a small time frame when transplantation is feasible as the patient must be healthy enough to endure the procedure.

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials & Methods

Construction of Zinc-Finger Pools.

A detailed description of how OPEN zinc-finger pools were constructed is provided in Supplementary Experimental Procedures. In brief, zinc-finger libraries were constructed using cassette mutagenesis to randomize the recognition helix of one finger in a threefinger domain. "B2H selection strains" harboring the target nine by site were constructed as described (Thibodeau-Beganny and Joung, 2007). Zinc-finger pools were obtained using two selection steps: First, randomized library members were introduced into a B2H selection strain and plated on histidine-deficient selective media (NM media) containing 3-AT, a competitive inhibitor of the HIS3 enzyme. Surviving colonies were scraped and infected with M13K07 helper phage to rescue zinc-finger-encoding phagemids as infectious phage particles. Second, rescued phagemids were used to infect fresh B2H selection cells and plated on NM media containing 3-AT and streptomycin. 95 surviving colonies were picked and inoculated into a 96-well block for growth and plasmid DNA isolated to obtain the final finger pools (FIG. 1A).

OPEN Selections.

A detailed description of how OPEN selections were performed is provided in Supplementary Experimental Procedures. In brief, for each target site, PCR-mediated fusion was used to create phage-based libraries consisting of random combinations of three finger pools (FIG. 1B) expressed as fusions to a fragment of the Gal11P protein (FIG. 1C). OPEN selections were performed in two steps. First, B2H selection strain cells were infected with randomized zinc-finger phage library and then plated on NM media containing 3-AT and streptomycin. Surviving colonies were scraped and infected with M13K07 helper phage to rescue the zinc-finger-encoding phagemids as phage. In a second step, this enriched phage library was then used to re-infect fresh B2H selection strain cells which were then plated on NM media containing a gradient of 3-AT and streptomycin. For a small number of the OPEN selections, the inventors performed selections in a single step (see below).

Quantitative Bacterial Two-Hybrid (B2H) Assays.

Zinc-finger-encoding plasmids identified from OPEN selections were co-transformed with an α-Gal4 expression plasmid into a "B2H reporter strain" harboring a single copy bacterial plasmid with a target binding site positioned upstream of a weak promoter driving lacZ expression. B2H reporter strains were constructed as described (Wright et al., 2006). β-galactosidase assays were performed in triplicate as described (Thibodeau et al., 2004).

Human cell-based EGFP-disruption assay. Human 293.EGFP cells harbor an integrated retroviral construct which constitutively expresses a β-galactosidase-EGFP fusion protein (FIG. 2C). 50,000 transfected cells were analyzed by flow cytometry two and five days post-transfection to determine the percentage of EGFP-negative cells. Statistical significance was determined using a two-sided student's t-test with unequal variance.

CEL I Nuclease Assay for NHEJ-Mediated Mutation.

Flp-In T-REx 293 cells (Invitrogen) were transfected with ZFN expression plasmids and genomic DNA was isolated three days post-transfection. Limited-cycle PCR was performed with radiolabeled nucleotides and VEGF-A- or HoxB13-specific primers. PCR products were treated with CEL I nuclease and then separated on 10% polyacrylamide gels and visualized using a phosphorimaging screen. All experiments were performed a minimum of two times.

Gene Targeting Assays.

Human Flp-In T-REx 293 and K562 cells were transfected with ZFN expression plasmids and donor constructs and genomic DNA harvest three and four days post-transfection. Limited-cycle PCR was performed with radiolabeled nucleotides and VEGF-A- or IL2Rγ-specific primers. PCR products digested with SalI (for VEGF-A) or BsrBI (for IL2Rγ) were separated on 10% polyacrylamide gels and visualized using a phosphorimaging screen. Additional details and Southern blot assays are described below.

Tobacco Transformation and Assay for Mutations.

The transformation of tobacco protoplasts by electroporation was carried out as previously described (Wright et al., 2005). Protoplasts were allowed to recover and then selected for kanamycin resistance and regenerated into plantlets as previously described (Wright et al., 2005). DNA was prepared from tissue harvested from individual plantlets using the Epicentre MasterPure Plant leaf DNA Purification Kit. SuRA and SuRB alleles were amplified by PCR, gel purified, and sequenced to identify mutations (see Supplementary Experimental Procedures for additional details).

Sequencing of Modified Genomic Alleles.

PCR products amplified from genomic DNA were cloned into the pCR4Blunt-TOPO plasmid using the Zero Blunt TOPO PCR Cloning Kit for Sequencing (Invitrogen). Plasmid DNA was isolated from transformants and sequenced using primers as described in Supplementary Experimental Procedures.

ZFN Toxicity Assays.

ZFN expression vectors, donor templates, and plasmid pmaxGFP (Amaxa) were transfected into K562 cells. Cells were assayed for GFP expression at days 1 and 7 posttransfection using a FACScan cytometer and for gene targeting efficiencies at days 4 and 7 post-transfection using the limited-cycle PCR/restriction digest assay. Variant heterodimer FokI domains were constructed by introducing the "+" and "−" mutations previously described in Miller et al. (2007).

Fluorescence In Situ Hybridization (FISH).

Two-color fluorescence in situ hybridization (FISH) was performed on 3:1 methanolacetic acid fixed cell lines using bacterial artificial chromosome clones RP11-710L16

(6p21.1; VEGFA) labeled in Spectrum Orange (Abbott-Vysis, Downer's Grove, Il.), or RP11-142P4 (14q31.1; copy number control) labeled in Spectrum Green using standard protocols. Images were captured using an Olympus BX61 fluorescent microscope equipped with a CCD camera, and analysis was performed with Cytovision software (Applied Imaging, San Jose, Calif.).

B2H Selection Media.

NM medium has been previously described (Thibodeau-Beganny and Joung, 2007). NM/CCK medium plates contain 100 µg/mL carbenicillin, 30 µg/mL chloramphenicol, 30 µg/mL kanamycin, and 1.5% Bacto-agar.

Construction of Zinc Finger Pools.

All master randomized zinc finger libraries were constructed in a standard framework consisting of three tandem repeats of the middle finger of the murine transcription factor Zif268 in which the recognition helix residues have been altered. For each library, recognition helix residues −1, 1, 2, 3, 5, and 6 were randomized using 24 codons (degenerate sequence 5'VNS3') encoding 16 amino acids (excluding cysteine and the aromatics). The theoretical complexity of each library is therefore $24^6 = ~2 \times 10^8$ members.

B2H selection strains each harbor: (1) a single copy episome bearing a target site of interest positioned upstream of a promoter which drives co-cistronic expression of two selectable markers (the yeast HIS3 gene and the bacterial aadA gene) and (2) a low copy number plasmid expressing the RNA polymerase α-subunit/yeast Gal4 hybrid protein (α-Gal4). Strains were constructed as previously described (Thibodeau-Beganny and Joung, 2007). The target binding site of each strain was verified by DNA sequencing.

Zinc finger pools were obtained using two selection steps. In a first step, $10^9$ ampicillin-transducing units (ATU) of randomized zinc finger phage library were introduced into $>3 \times 10^9$ B2H selection strain cells harboring a target subsite of interest. Transformed cells were plated on histidine-deficient NM/CCK medium plates containing 50 µM isopropyl β-d-thiogalactoside (IPTG) and 10 mM 3-aminotriazole (3-AT), a competitive inhibitor of the HIS3 enzyme. After incubation for 24 hours at 37° C. followed by 18 hours at room temperature, surviving colonies were scraped from the plates and infected with M13K07 helper phage to rescue the zinc finger-encoding phagemids as infectious phage. In a second step, this enriched phage library was then used to re-infect fresh B2H selection strain cells and the resulting transformants plated on NM/CCK medium plates containing 50 µM IPTG, 10 mM 3-AT, and 20 µg/ml streptomycin. After incubation at 37° C. for 48 hours, the inventors inoculated 95 surviving colonies into individual wells of a 96-well block containing 1 ml of Terrific Broth and 50 µg/ml carbenicillin. These cultures were grown overnight at 37° C. and then a 96-pin replicator was used to inoculate a second block of identical cultures. Glycerol was added to a final concentration of 15% to all wells in the first block and this was stored at −80° C. The second block was grown overnight at 37° C. and then the 95 cultures were pooled together. Plasmid DNA encoding the finger pools was isolated from 10 ml of the pooled culture using a QIAgen miniprep kit and for most pools a small number of random clones were sequenced with primer OK61. For finger pools against nine subsites, sequencing revealed no strong consensus (i.e., the sequences were diverse and did not resemble one another), suggesting that selective pressure for those sites was relatively weak under the initial selection conditions. For these nine subsites, the second step of selections were repeated and plated on higher stringency plates to obtain sequences that more closely resembled one another. The higher stringency plates used were NM/CCK medium plates containing 50 µM IPTG, 20 mM 3-AT, and 30 µg/ml streptomycin (for seven subsites: F1 GAT, F2 GAC, F2 GAG, F2 GCG, F2 TGA, F2 TAG, and F2 GTT) or 50 µM IPTG, 25 mM 3-AT, and 40 µg/ml streptomycin (for two subsites: F2 GAA, F2 TGG).

OPEN Selections.

Figure 6:
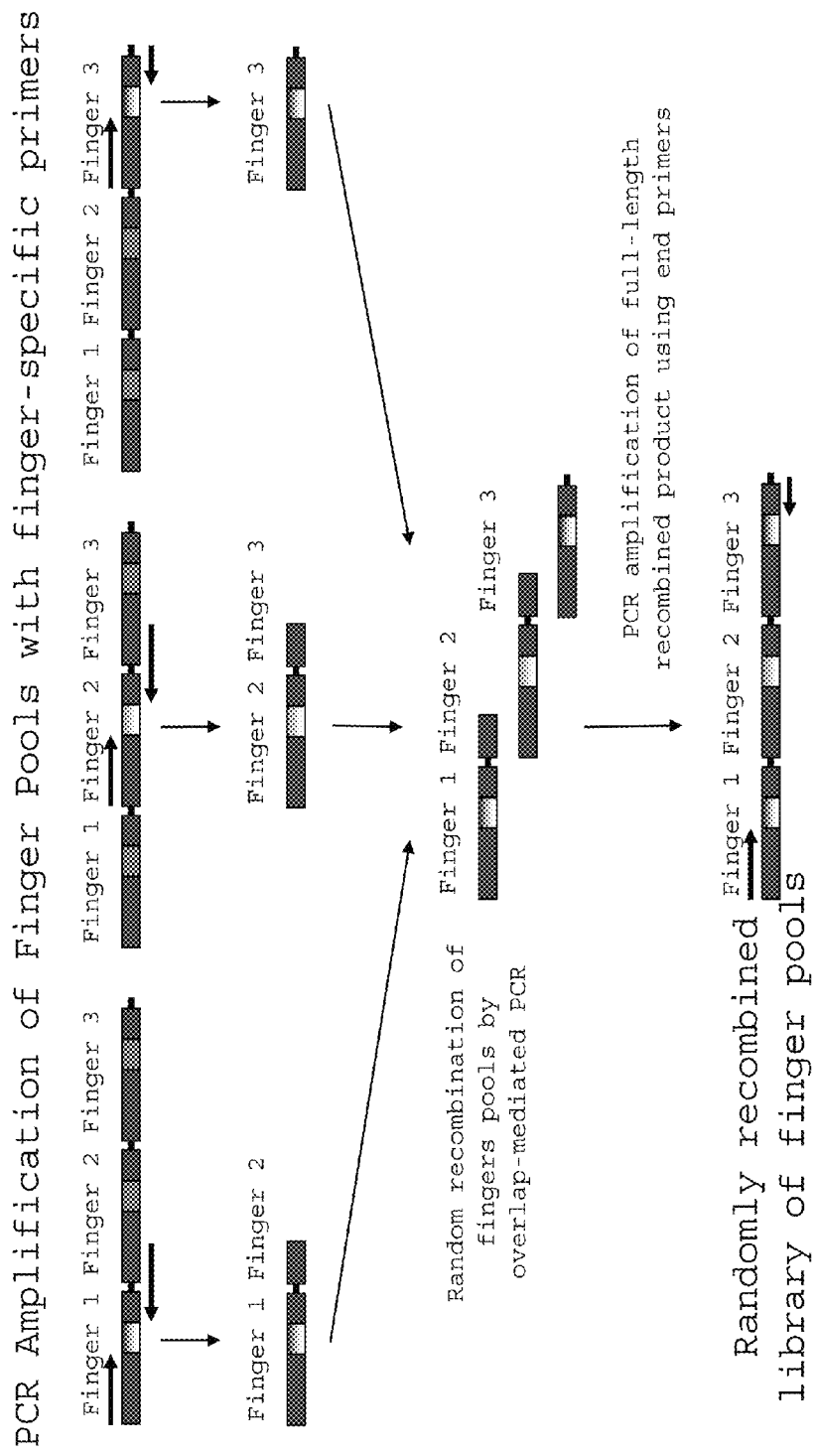
FIG. 6—PCR Strategy for Creating Recombined OPEN Libraries.

To create libraries for use in OPEN selections, finger pools were amplified by PCR (FIG. 6). For each amplification, first five and then 20 cycles of PCR were performed using the following primers and annealing temperatures (primer names; initial annealing temp; final annealing temp): for finger 1: OK1424 and OK1425; 55° C.; 59° C., for finger 2: OK1426 and OK1427; 52° C.; 57° C., for finger 3: OK1428 and OK1429; 41° C.; 56° C. Amplification of individual finger pools were isolated from 10% polyacrylamide gels and fused together by PCR. To do this, equal concentrations of the three finger pool fragments were fused using the following PCR conditions: 94° C., 5 minutes; 10 cycles of 94° C., 30 sec; 50° C., 30 sec; 72° C., 2 min; final extension 72° C., 7 min. This fusion product was purified using a QIAgen PCR purification kit and then amplified by PCR using primers OK1430 and OK1432 with 10 initial cycles of 94° C., 30 sec; 56° C., 30 sec; 72° C., 1 min and 20 additional cycles of 94° C., 30 sec; 64° C., 30 sec; 72° C., 1 min; final extension 72° C., 7 min. The final PCR product (encoding a library of three-finger arrays) was isolated on a 5% polyacrylamide gel and treated with Pfu polymerase and T4 polynucleotide kinase to create overhangs. This fragment was then ligated with BbsI-digested pBR-UV5-GP-FD2 vector backbone which results in a plasmid that expresses the zinc finger array as a FLAG-tagged Gal11P fusion in the B2H system. This ligation was then introduced into E. coli XL-1 Blue cells by electroporation and each library was constructed from $>3 \times 10_6$ independent transformants, ensuring at least three-fold oversampling of the theoretical library complexity of $~8.6 \times 10^5 (95^3)$.

Libraries were then converted into infectious M13 phage as previously described (Thibodeau-Beganny and Joung, 2007). All but six (see below) of the OPEN selections were performed in two stages. In the first stage, an OPEN three-finger library was introduced by infection into a B2H selection strain harboring the full target DNA sequence of interest. $>2.2 \times 10^6$ ATU of OPEN phage library were used to infect $>2 \times 10^8$ B2H selection strain cells and the resulting transformants were plated on two different NM/CCK medium plates containing 50 µM IPTG, 10 mM 3AT, and 20 ng/mL streptomycin or 50 µM IPTG, 25 mM 3AT, and 40 µg/mL streptomycin. After 36-48 hours of incubation, colonies were harvested from the highest stringency plate yielding at least 1000 colonies. These cells were infected with M13K07 helper phage to rescue zinc finger-encoding phagemids, thereby creating an enriched library. In the second stage, $2.5 \times 10^6$ ATU of this enriched library were used to infect $>2 \times 10^8$ fresh B2H selection strain cells and the resulting transformants plated on a 245×245 mm NM/CCK medium plate containing parallel gradients of 3-AT and streptomycin ranging from 0 mM to 80 mM and 0 µg/mL to 100 µg/mL, respectively.

Gradient plates were poured using the method of Szybalski (Bryson and Szybalski, 1952). After incubation at 37° C. for a minimum of 48 and a maximum of 96 hours, 12 surviving colonies were picked from the highest stringency edge of the plate and ZFP-encoding plasmids were isolated by plasmid miniprep and sequenced with primer OK61. For six of the sites, the inventors targeted using OPEN, selections were performed in a single step (instead of two steps). For five sites (EG223L, EG223R, EG292L, EG292R, and EG382L), $>3.1 \times 10^6$ ATU of OPEN phage library were used to infect $>4 \times 10^8$ B2H selection strain cells and the resulting transformants were plated on a series of NM/CCK medium plates containing 50 µM IPTG, 40 mM 3AT, and 60 µg/mL streptomycin, 50 µM IPTG, 60 mM 3AT, and 80 µg/mL streptomycin, 0 µM IPTG, 40 mM 3AT, and 60 µg/mL streptomycin or 0 µM IPTG, 60 mM 3AT, and 80 µg/mL streptomycin. For each target site, the inventors picked colonies from the highest stringency plates that yielded colonies. For one site (EG382R), $4.25 \times 10^8$ ATU of OPEN phage library were used to infect $>10^9$ B2H selection strain cells and the resulting transformants were plated on a 245×245 mm NM/CCK medium plate containing parallel gradients of 3-AT and streptomycin ranging from 0 mM to 80 mM and 0 µg/mL to 100 µg/mL, respectively. Colonies were picked from the highest stringency edge of the plate.

Construction of Modularly Assembled Zinc Finger Arrays.

Modularly assembled zinc finger arrays were assembled using the Zinc Finger Consortium Modular Assembly Kit v1.0 as previously described (Wright et al., 2006). For each target half-site in the EGFP reporter gene, the inventors assembled three-finger arrays using modules from the Barbas, Sangamo, and Toolgen archives but they did not mix and match modules across platforms because: (1) the Barbas group does not suggest use of their modules with others (Mandell and Barbas, 2006), (2) the Toolgen group discovered that their human zinc fingers worked best with one another but not as well with other engineered modules (Bae et al., 2003), and (3) the Sangamo modules were designed to be finger-position-specific and have non-canonical linkers joining them that differ from the TGEKP linker used by the Barbas and Toolgen modules (Liu et al., 2002).

ZFN Expression Vectors.

All zinc finger arrays were expressed as ZFNs using the Zinc Finger Consortium mammalian expression vector pST1374 (Wright et al., 2006). Zinc finger arrays were excised directly from B2H expression vectors on an XbaI/BamHI fragment and cloned into pST1374. In this configuration, zinc finger arrays are joined to the FokI nuclease domain by a four amino acid linker of sequence LRGS.

Human Cell-Based EGFP-Disruption Assay.

293.EGFP cells were transfected in triplicate in 24-well plates using calcium phosphate precipitation as previously described (Cathomen et al., 2001). Transfection cocktails included 300 ng each of a CMV promoter-controlled zinc finger nuclease expression vector, 100 ng pDS.RedExpress (Clontech, Mountain view, Calif.) and pUC118 to 1.5 µg. 600 ng of pRK5.SceI plasmid (Alwin et al., 2005), which expresses the meganuclease ISceI, was used in place of GFP-ZFN-encoding plasmids for negative controls. 50,000 cells were analyzed by flow cytometry two and five days post-transfection to determine the percentage of EGFP-negative cells. The number of REx-positive cells at day 2 was used to normalize for transfection efficiency.

CEL I Nuclease Assay for NHEJ-Mediated Mutation.

$2 \times 10^6$ human Flp-In T-REx 293 cells (Invitrogen) were transfected with pairs of ZFN-encoding plasmids (100 or 250 ng of each ZFN-encoding plasmid) using Lipofectamine 2000 (Invitrogen). Genomic DNA was isolated from nuclease-treated cells at 3 days post-transfection using the QIAgen Blood Mini kit. Limited-cycle PCR (24 cycles) was performed using Platinum PCR SuperMix Hi-Fidelity (Invitrogen) or its equivalent constituent components (Invitrogen) with 50 ng of genomic DNA as template, 8 µCi of each $[\alpha^{32}]$-dATP and dCTP, 1 µM each of gene-specific primers and 1.25 µl DMSO in a 25 µl reaction volume. PCR products were cleaned up using Sephadex G-50 columns (Roche) and then melted/re-annealed using the following conditions: 95° C. for 10 min; 95° C. to 85° C. cooling at a rate of −2° C./sec; 85° C. to 25° C. cooling at a rate of −0.1° C./see; rapid cool to 4° C. Re-annealed PCR products were diluted 1:3.75 in a buffer of 20 mM Tris-HCl (pH 8.8), 2 mM MgSO$_4$, 60 mM KCl, 0.1% Triton X-100 and treated with 1 µl CEL I enzyme (Surveyor nuclease S; Transgenomic) and 1 µl Surveyor Enhancer S (Transgenomic) in a 15 µl reaction incubated at 42° C. for 20 min. Products were visualized by electrophoresis on a 0.8 mm thick, 10% 1×TBE polyacrylamide gel which was dried down and exposed overnight to a phosphorimaging screen.

Gene Targeting Assays.

$2 \times 10^6$ Flp-In T-REx 293 cells were transfected with pairs of plasmids expressing ZFNs (7.5 µg of each ZFN-encoding plasmid) and 50 µg of donor plasmid using nucleofection with solution V and program Q001 (Amaxa). $2 \times 10^6$ K562 cells were transfected with ZFN expression plasmid pairs (5 or 7.5 µg of each) and matched donor construct (25 or 50 µg donor plasmid) using nucleofection with solution V and program T-16. Genomic DNA was harvested 3 or 4 days post-transfection for 293 or K562 cells, respectively, using a QIAgen Blood Mini kit. Transfection efficiencies were monitored by including a GFP-encoding plasmid in each transfection and determining the percentage of GFP-positive cells by flow cytometry one day post-transfection. For experiments in which cells were arrested in G2 phase, 0.2 µM vinblastine was added 24 hours post-transfection and then removed by washing three times with phosphate buffered saline 14-18 hours later. Limited-cycle PCR assays (24 cycles) were performed using Platinum PCR SuperMix Hi-Fidelity (Invitrogen) or its equivalent constituent components (Invitrogen) with 4 ng genomic DNA, 8 µCi of each $[\alpha^{32}P]$-dATP and dCTP, 1 µM each of gene-specific primers and 1.25 µl DMSO in a 25 µl reaction. Purified PCR product was digested with 25 units SalI or 10 units BsrBI restriction enzyme for 2 hours and the resulting products were visualized by electrophoresis on a 10% 1×TBE polyacrylamide gel. This gel was dried down and exposed overnight to a phosphorimaging screen. Quantification of bands was performed using Quantity One software (Bio-Rad).

For Southern blots, 15 µg of genomic DNA (15 µg) was digested with MscI and SalI restriction enzymes for 20 hrs, electrophoresed in 0.8% tris-acetate agarose gels (100 mM Tris-HCl, 10 mM EDTA, pH 8.0 with acetic acid), and transferred to Zeta-probe nylon membrane (BioRad) using 25 mM sodium phosphate (pH 6.5) according to the procedure of Southern (Southern, 1975) as modified for use with the Turbo-Blot downward transfer apparatus. The VEGF-A DNA probe was generated by PCR amplification of a cloned human VEGF-A DNA template which was subsequently labeled (25 ng) with $[\alpha^{32}P]$-dCTP) using Rediprime II random priming reagents (Amersham). Following hybridization (20 hrs) at 65° C. in 5 mL ExpressHyb solution (Clontech), the filters were washed with 0.1×SSC/0.1% SDS at 65° C. (2 hrs), blotted dry and exposed to a phosphorimager screen and/or film. The filters were scanned in the Typhoon 8600 phosphoimager and relative band intensities were quantified by volume analysis using ImageQuant software (GE Healthcare/Amersham).

Sequencing of Modified Genomic Alleles.

The region encompassing each potential ZFN cleavage site was amplified from genomic DNA isolated from populations of human Flp-In T-REx 293 or K562 cells that had been transfected with ZFN expression plasmids alone or with ZFN expression and donor plasmids. PCR conditions for these amplifications were the same as those used for the CEL I (for assessing NHEJ events) or limited-cycle PCR/restriction digest (for assessing gene targeting events) assays but with all components doubled to a final volume of 50 µl. CF877 was amplified using primers OK1711 and 1713. PCR reactions were purified using the QIAgen Minelute PCR Purification kit and eluted with 15 µl 0.1× EB buffer (QIAgen). PCR fragments were cloned into the pCR4Blunt-TOPO plasmid using the Zero Blunt TOPO PCR Cloning Kit for Sequencing (Invitrogen). The TOPO cloning reaction used 4 µl purified PCR product, 1 µl salt solution and 1 µl TOPO vector. 2 µl of TOPO reaction were transformed into One Shot Mach1-T1 chemically competent cells (Invitrogen) or chemically competent Top10 cells (Invitrogen) and plated on LB plates containing 50 µg/ml kanamycin. Plasmid DNAs from transformants were sequenced with a primer designed to bind internal to the PCR product.

Tobacco Transformation and Assay for Mutations.

The transformation of tobacco protoplasts by electroporation was carried out as previously described (Wright et al., 2005). Plasmids introduced into protoplasts (10 µg each) included those expressing ZFNs that recognize the left (pRW242) and right (pRW246) half sites of target 2163 in SuRA. Note that these constructs do not express the heterodimeric variants of FokI endonuclease. Also transformed into protoplasts was a plasmid expressing neomycin phosphotransferase (NPTII) (pDW998). The CaMV 35S promoter was used to drive expression of both the ZFNs and NPTII. Plasmid DNAs were linearized with BglII prior to transformation. Protoplasts were allowed to recover and then selected for kanamycin resistance and regenerated into plantlets as previously described (Wright et al., 2005).

DNA was prepared from tissue harvested from individual plantlets using the Epicentre MasterPure Plant Leaf DNA Purification Kit following the manufacturer's directions. An initial PCR screen for mutations at the site of ZFN cleavage was performed using primers to amplify a 445 bp fragment from both the SuRA and SuRB loci. PCR was performed with 100 ng of genomic DNA and the following PCR conditions: 94° C. 2 min, followed by 34 cycles of 94° C. 15 sec, 61° C. 15 sec, 72° C. 30 sec, and then 72° C. for 5 min. The reactions were run out on a 0.8% agarose gel, purified using a QIAgen QIAquick Gel Extraction kit, and sequenced. The resulting sequences were examined for double peaks, which not only indicate sequence differences between SuRA and SuRB, but also identify potential insertion/deletion events at the ZFN cleavage site in either or both loci.

DNA from candidate mutants was then PCR amplified using a set of nested, allele-specific primers in two consecutive PCR reactions to confirm the mutation and determine if it occurred in SuRA or SuRB. The primary reaction amplified a 2.15 kb fragment using approximately 100 ng of genomic DNA as template and primers for SuRA and SuRB. The second PCR reaction amplified a 2 kb fragment using 1 µl of the primary PCR reaction as template and primers SuRA and SuRB. All PCR reactions were performed using a Clontech Advantage cDNA Polymerase kit and the following PCR conditions: 94° C. 1 min, followed by 34 cycles of 94° C. 30 sec, 66° C. 30 sec, 68° C. 3 min, and then 68° C. for 5 min. The reactions were run out on a 0.8% agarose gel, purified with a QIAgen QIAquick Gel Extraction kit and sequenced with primer DVO4462.

ZFN Toxicity Assays.

ZFN expression plasmids and donor templates were transfected into K562 cells using nucleofection as described above. For these experiments, 5 µg of each ZFN expression plasmid, 25 µg of donor, and 15 ng of pmaxGFP (encoding a GFP variant; Amaxa) were included in each transfection. For controls, the inventors transfected: (1) 10 µg of plasmid encoding I-SceI meganuclease (Porteus and Baltimore, 2003) with 25 µg pUC118 and 15 ng of pmaxGFP, (2) 10 µg of plasmid encoding CAD (caspase-activated DNase) protein (Pruett-Miller et al., 2008) with 25 µg pUC118 and 15 ng of pmaxGFP, or (3) 35 µg of pUC118 and 15 ng of pmaxGFP. Cells were assayed for GFP expression at post-transfection days 1 and 7 with a FACScan cytometer. GFP ratios shown in FIG. 4J (green bars) were calculated using the formula:

$$\frac{(\%\ GFP+\text{in }ZFN\text{-transfected cells on day 7}/}{(\%\ GFP+\text{in }pUC\text{-transfected cells on day 7}/}$$
$$\%\ GFP+\text{in }pUC\text{-transfected cells on day 1})$$

In addition, genomic DNA was harvested using a QIAgen Blood Mini Prep kit on post-transfection days 4 and 7 and assayed for gene targeting using the limited-cycle PCR/restriction digest assay as described above. Gene targeting ratios shown in FIG. 4J (purple bars) were calculated by dividing the gene targeting rate on day 7 by the gene targeting rate on day 4. All assays (both GFP and gene targeting) were performed on at least three-independent samples and t-tests of significance were performed by comparing experimentally determined ratios to a fixed ratio value of 1 (i.e., no change in value).

Example 2

Results

OPEN: A Rapid and Robust Strategy for Engineering Zinc-Finger Arrays.

Previous work has suggested that context-dependent DNA-binding effects can occur within multi-finger arrays (i.e., the binding activity of one finger may be influenced by neighboring fingers) (Elrod-Erickson et al., 1996; Isalan et al., 1998; Wolfe et al., 1999). Failure to consider these context-dependent effects is a likely reason for the very low success rates observed with modular assembly strategies (Ramirez et al., 2008) which treat individual finger domains as independent units. Various groups have proposed strategies for engineering zinc-finger arrays that identify combinations of fingers from randomized libraries that work well together, thereby accounting for context-dependence.

Zinc-finger arrays engineered using these approaches possess high DNA-binding affinities and specificities (Greisman and Pabo, 1997; Hurt et al., 2003; Isalan et al., 2001) and function with high activities and low toxicities when expressed as ZFNs in human cells (Cornu et al., 2008; Pruett-Miller et al., 2008). However, all of these strategies require the construction of multiple randomized libraries typically $>10^8$ in size and are therefore impractical for routine use by all but a few laboratories that possess the required expertise.

The new OPEN method for engineering zinc-finger arrays considers context-dependent effects but also eliminates the need for specialized expertise in the construction and interrogation of multiple, very large randomized libraries. The practice of OPEN requires an archive of pre-selected zinc-finger pools, each targeted to a different three base pair sub-site at one of three finger positions within a three-finger array (FIGS. 1A and 1B). Each finger pool contains a mixture of zinc-fingers (maximum of 95) that is obtained by performing low stringency selections from very large zinc-finger libraries $>2\times10^8$ in size (see above). To use OPEN to identify a multi-finger array that binds to a given target DNA site, appropriate finger pools from the archive are recombined to create a small single library of variants which is then interrogated using plates containing gradients of selective agents (FIG. 1B). Because each finger pool is composed of no more than 95 different members, the combinatorial diversity of the library is relatively modest ($95^3=8.6\times10^5$ for a three-finger domain). Selections are performed using a simple bacterial two-hybrid (B2H) system in which binding of a zinc-finger domain to its cognate site triggers the expression of selectable marker genes (FIG. 1C) (Hurt et al., 2003; Joung et al., 2000). The inventors reasoned that this overall approach would identify combinations of fingers that work well together (thereby accounting for context-dependent effects on DNA-binding) while avoiding the need for the end-user to interrogate very large randomized libraries—a technically demanding and labor-intensive step.

Construction of an Initial Archive of OPEN Finger Pools.

Fully enabling the OPEN method requires an archive of 192 finger pools (64 possible three base pair target subsites for each position in a three finger protein). As an initial step toward full implementation of OPEN, pools were created that recognize subsites of the form 5'-GXX or 5'-TXX (where X is any base). GXX subsites were chosen to allow direct comparison of OPEN-generated three-finger domains with those made by modular assembly (Bae et al., 2003; Liu et al., 2002; Mandell and Barbas, 2006). TXX subsites were of interest because very few finger modules that bind to these sites have been reported (Mandell and Barbas, 2006). Using the approach outlined in FIG. 1A, finger pools were created for a total of 66 subsites (all possible 48 GXX subsites and 18 TXX subsites). For each finger pool, the inventors inoculated 95 surviving colonies into 96-well plates for growth and isolation of zinc-finger-encoding plasmid DNA (FIG. 1A). Even with this partial set of finger pools, OPEN can be used to target ~4% of all 262,144 potential nine base pair target sites, thereby enabling researchers on average to find approximately five full ZFN sites in any given kb of sequence. To simplify the identification of potential ZFN sites that can be targeted with the initial archive of OPEN finger pools, the inventors created a modified version of their pre-existing ZiFiT software which was originally designed for use with the modular assembly zinc-finger engineering method (Sander et al., 2007; Wright et al., 2006). This new version, Zinc Finger Targeter, V 2.0 (available on the world-wide-web at zincfingers.org), scans an input sequence and identifies all three-finger ZFN sites that can be targeted by OPEN.

Comparing ZFNs Made by Modular Assembly and OPEN Methods.

To compare the efficacy of the OPEN method with the well-described modular assembly approach, the inventors constructed multi-finger domains against five potential ZFN target sites in EGFP (ten "half-sites"; see FIG. 2A) using both strategies. Modularly assembled arrays were made using finger modules from three different archives (see above). OPEN selections were used to engineer zinc finger arrays for the ten EGFP half-sites as described in Experimental Procedures. All 10 OPEN selections yielded zinc-finger arrays which closely resemble one another), a result which suggests that the selections identified the best combinations of fingers for each target site.

Figure 2B:
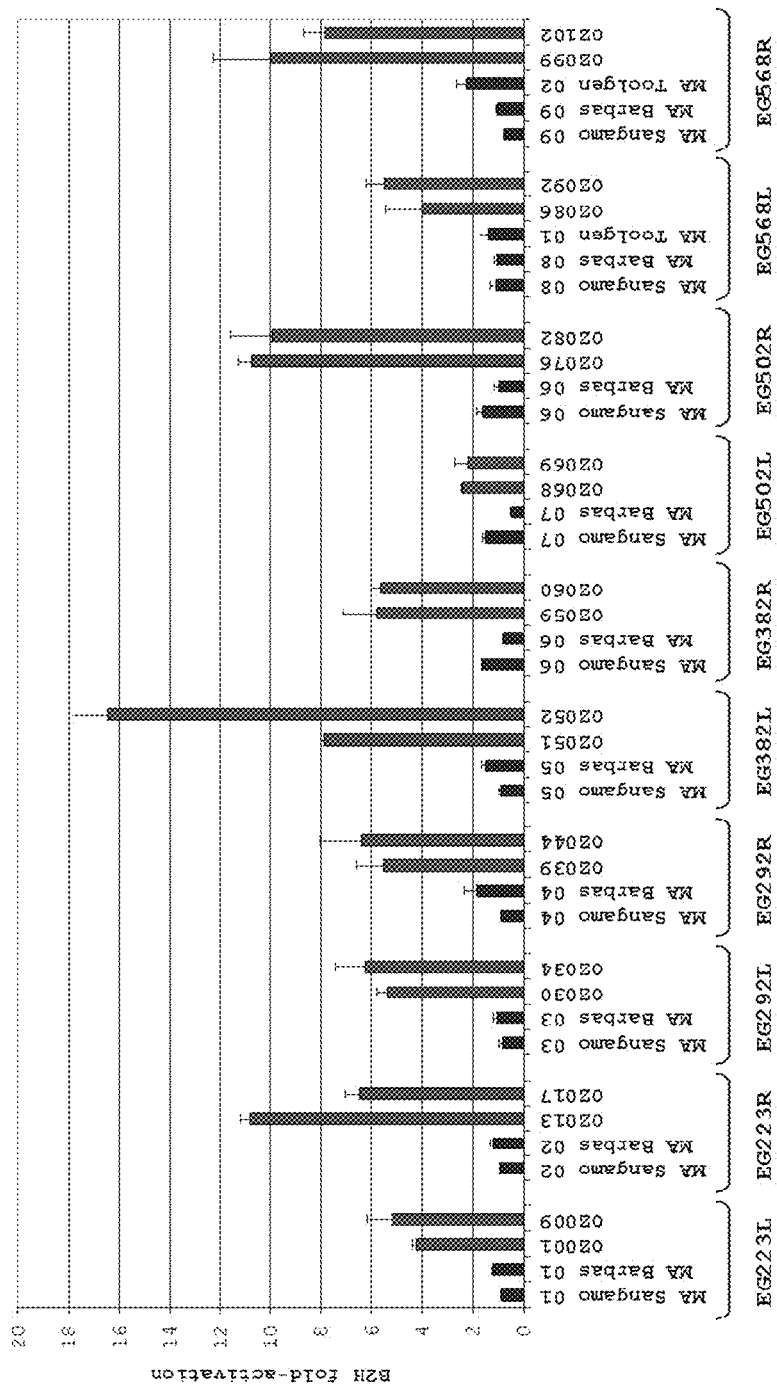

DNA-binding activities of the modularly assembled and OPEN-selected zinc-finger arrays targeted to EGFP sequences were assessed using a quantitative version of the B2H assay. Previous studies have shown that zinc-finger arrays with high affinities and specificities activate transcription more than three-fold in the B2H system (Hurt et al., 2003). As shown in FIG. 2B, all of the modularly assembled zinc-finger arrays tested on the 10 target half-sites failed to activate transcription by more than threefold. Western blotting verified that all modularly assembled zinc-finger arrays were expressed in these assays (data not shown). By contrast, OPEN selections yielded at least one—in most cases, many—zinc-finger array that activated transcription in the B2H by more than three-fold for nine of the 10 target half-sites (FIG. 2B). Although half-site EG502L did not yield OPEN zinc-finger arrays which activated by more than three-fold, the inventors note that the basal level of transcription from the B2H reporter bearing this site was high, a situation which can artifactually lower the apparent fold-activation observed.

Figure 2C:
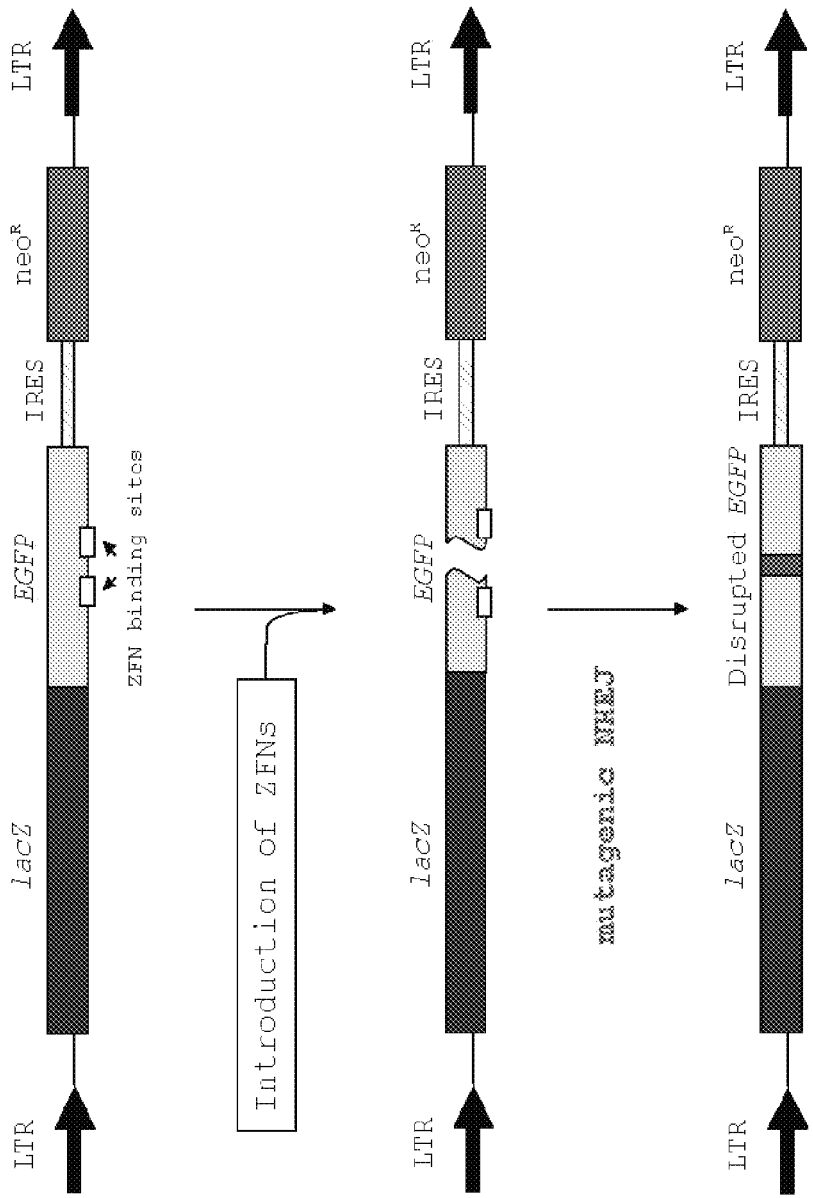
Figure 2D:
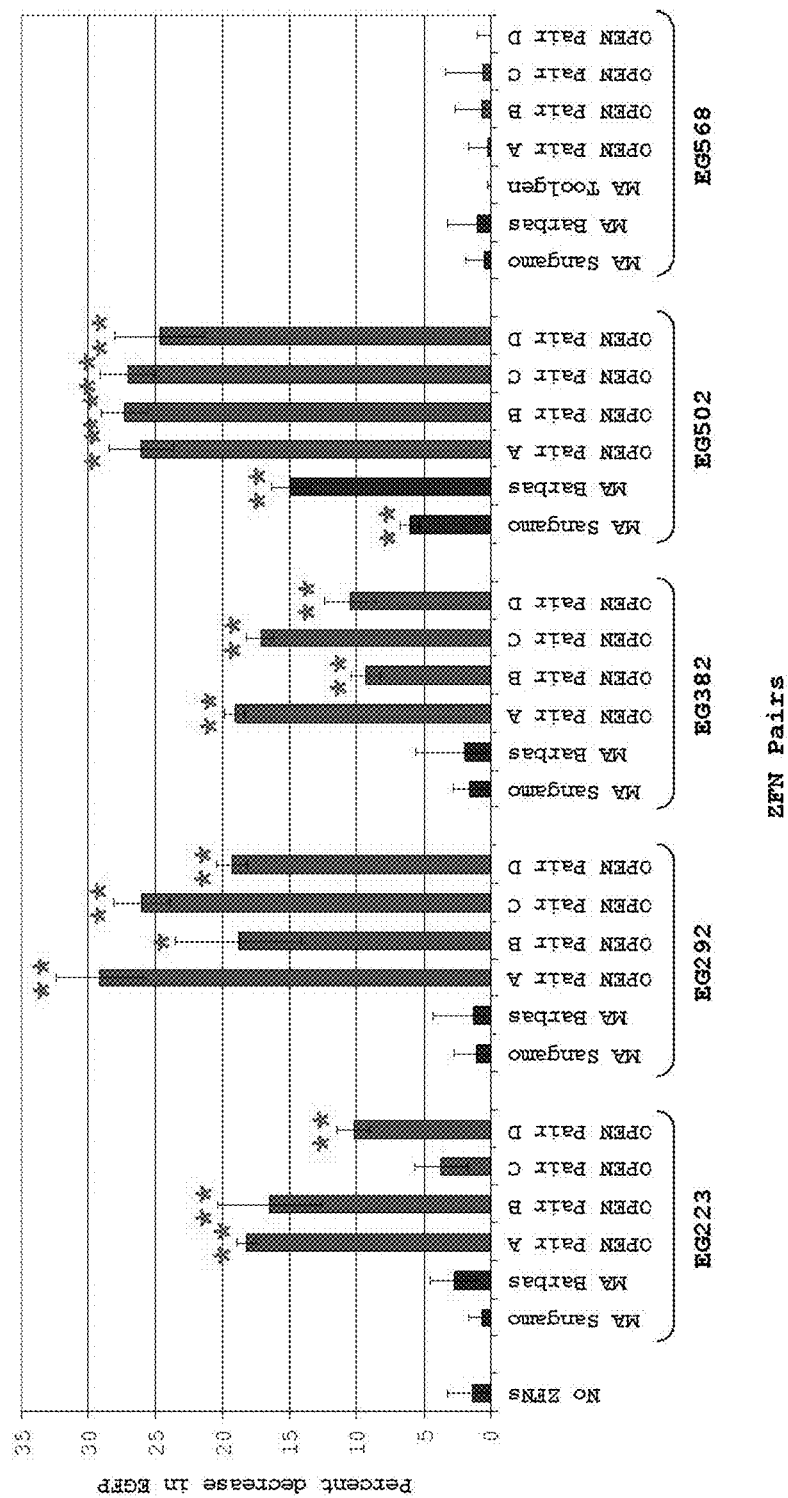

The EGFP zinc-finger arrays made by modular assembly and OPEN were next tested as ZFNs in human cells. Previous studies have shown that ZFNs can induce (via error-prone NHEJ) targeted insertions and deletions into human genes with high efficiency (Lombardo et al., 2007; Miller et al., 2007). Therefore, the inventors tested the activities of ZFNs using a human cell-based EGFP-disruption assay in which ZFN-induced DSBs lead to coding sequence alterations of a chromosomally integrated EGFP reporter gene (FIG. 2C). For each of the five full EGFP ZFN target sites, two or three pairs of modularly assembled ZFNs and four pairs of OPEN-selected ZFNs were chosen for testing. As shown in FIG. 2D, modular assembly yielded ZFN pairs with activities above background for only one of the five sites (EG502). By contrast, OPEN selection yielded active ZFN pairs for four of the five full ZFN target sites (EG223, EG292, EG382, and EG502). Although both methods yielded active ZFN pairs for the EG502 site, the pairs made by OPEN were significantly more active than the pairs made by modular assembly (FIG. 2D). Control Western blot experiments verified the expression of all ZFNs tested (data not shown). The inventors speculate that the EG568 ZFNs may be inactive due to the effects of methylation or chromatin at that site in the chromosomally integrated EGFP reporter because one of the modularly assembled and all of the OPEN ZFN pairs showed activity in an episomal-based version of this same assay (data not shown).

OPEN Selection of Zinc-Finger Arrays that Bind to Sequences in Endogenous Human and Plant Genes.

Figure 3A:
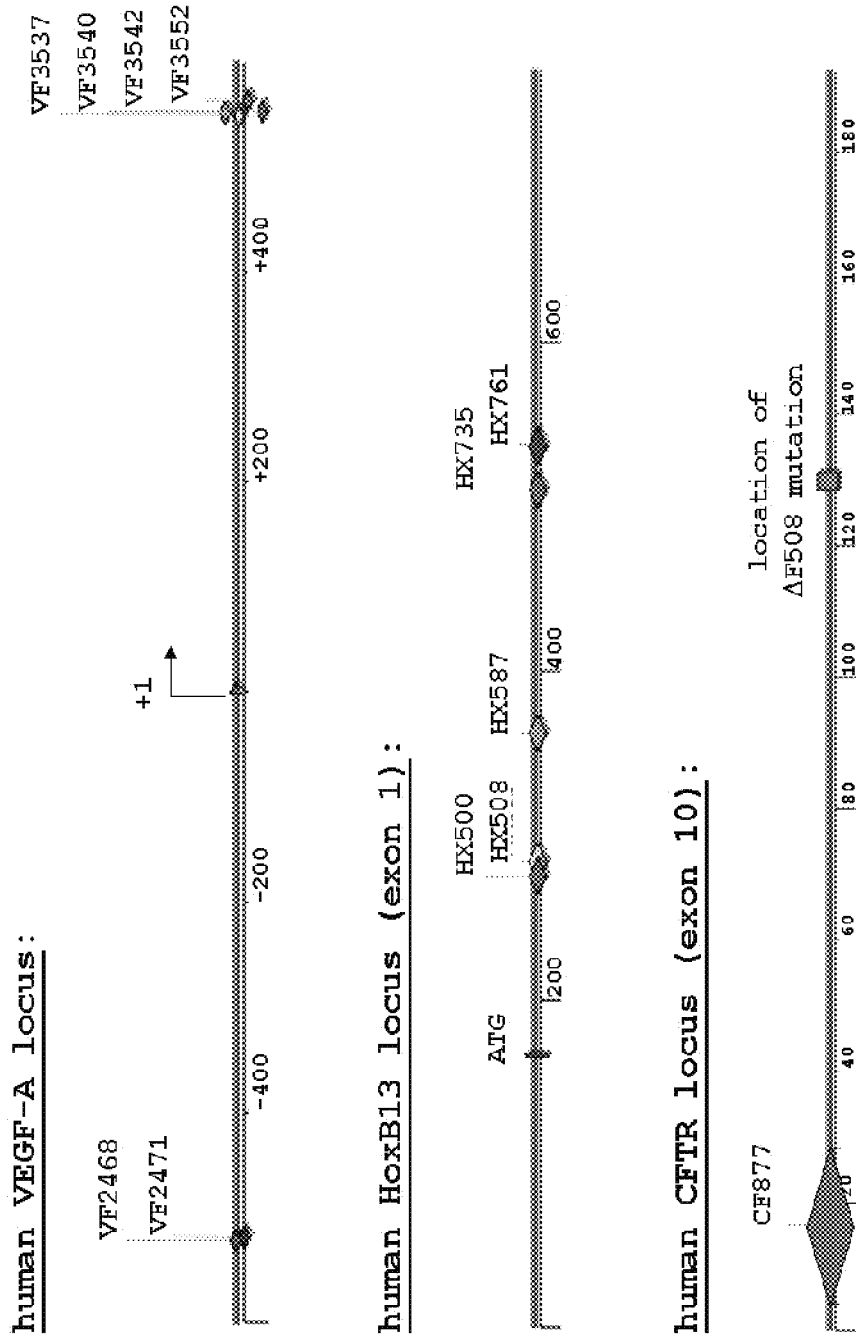

To further test the efficiency of the OPEN approach for engineering multi-finger arrays, ZiFiT 2.0 was used to identify 14 potential ZFN target sites in three endogenous human genes (CFTR, HoxB13, VEGF-A) and one endogenous plant gene (SuRA from *Nicotiana tobacum*) (FIG. 3A). The VEGF-A gene plays a critical role in angiogenesis, and the inventors targeted six different sites located within regions of open chromatin in its promoter (VF2468, VF2471, VF3537, VF3540, VF3542, and VF3552). The HoxB13 gene has been implicated as an important biomarker for resistance of breast cancers to the anti-hormonal drug tamoxifen (Ma et al., 2006; Ma et al., 2004), and the inventors targeted five sites (HX500, HX508, HX587, HX735, and HX761) within its first coding exon and one site (HX2119) within its last coding exon. The CFTR gene encodes a chloride channel that is mutated in people with cystic fibrosis (Welsh et al., 2001) and the inventors targeted a single site in exon 10 (CF877) that is positioned within 100 base pairs of the ΔF508 deletion. The tobacco SuRA and SuRB genes are highly similar and both encode acetolactate synthase, an enzyme which carries out the first step in branched chain amino acid synthesis and which is inhibited by several herbicides (Lee et al., 1988; McCourt et al., 2006); the inventors targeted a single site (SR2163) that is present in both the SuRA and SuRB genes.

OPEN selections were performed for the 28 different nine base pair sites, which together constitute the "half-sites" of the 14 full ZFN target sites. Twenty-five of the 28 OPEN selections yielded zinc-finger arrays whose sequences closely resembled one another, again suggesting that these selections identified the best combinations of fingers. However, one of these 25 selections (for half-site VF3540R) yielded fingers with sequences that appeared to bind to an alternative site. For 22 of the other 24 selections, the inventors obtained at least one zinc-finger array which activated lacZ expression by more than three-fold in the quantitative B2H assay; the two remaining selections were also deemed to be successful because their reporters possessed a high basal level of transcription which can artifually mask a higher true fold-activation. Using the finger arrays, the inventors constructed ZFN pairs for five full sites in VEGF-A, four full sites in HoxB13, one full site in CFTR, and one full site in the tobacco SuRA/ SuRB genes.

OPEN ZFNs Induce Highly Efficient Mutation of Endogenous Human and Plant Genes.

Figure 3B:
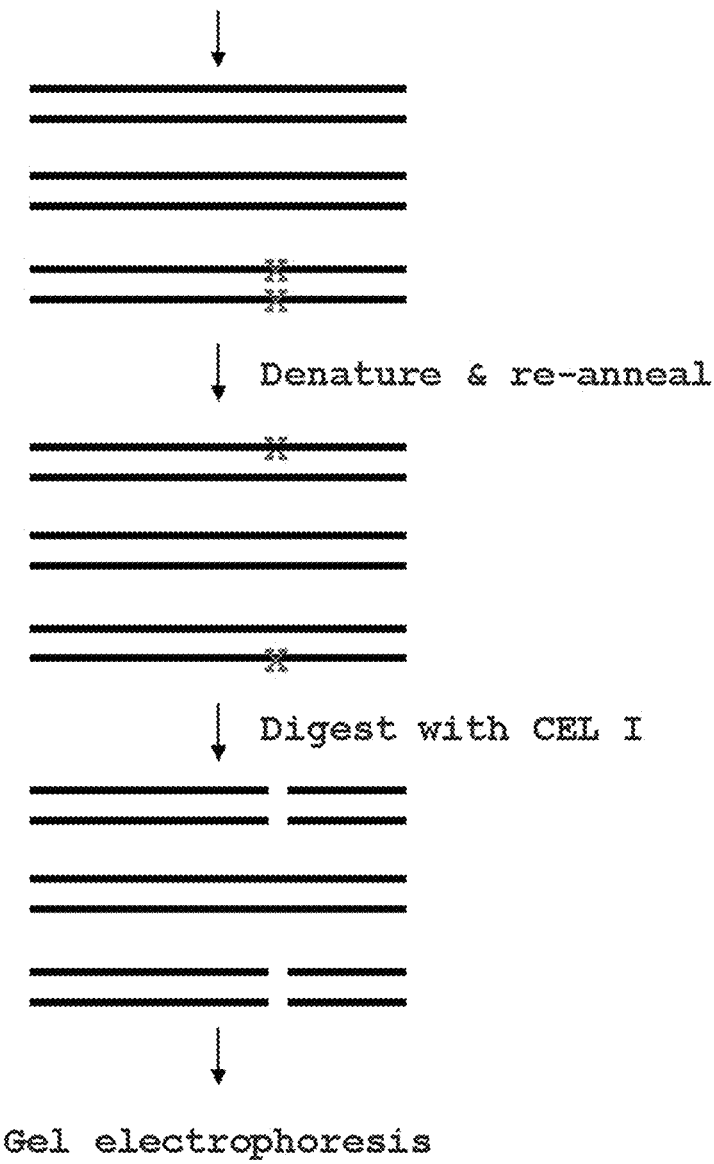
Figure 3C:
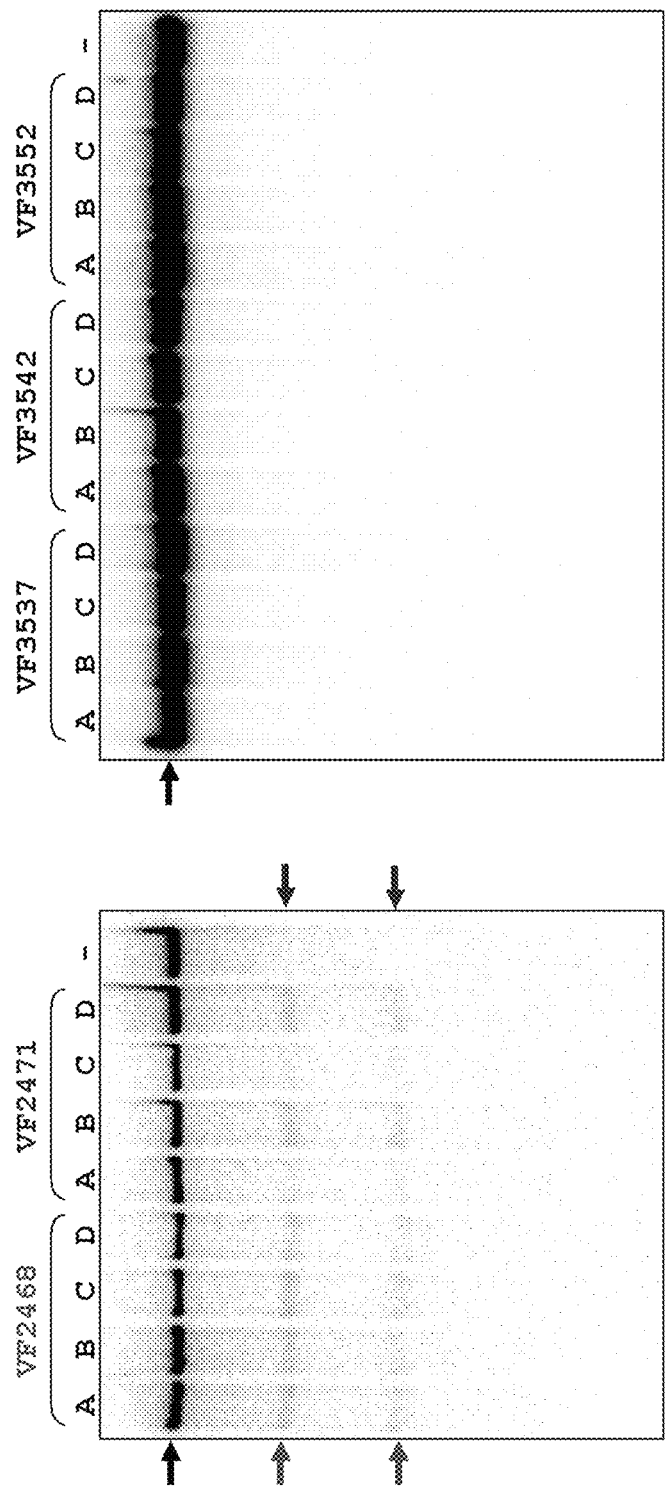
Figure 3D:
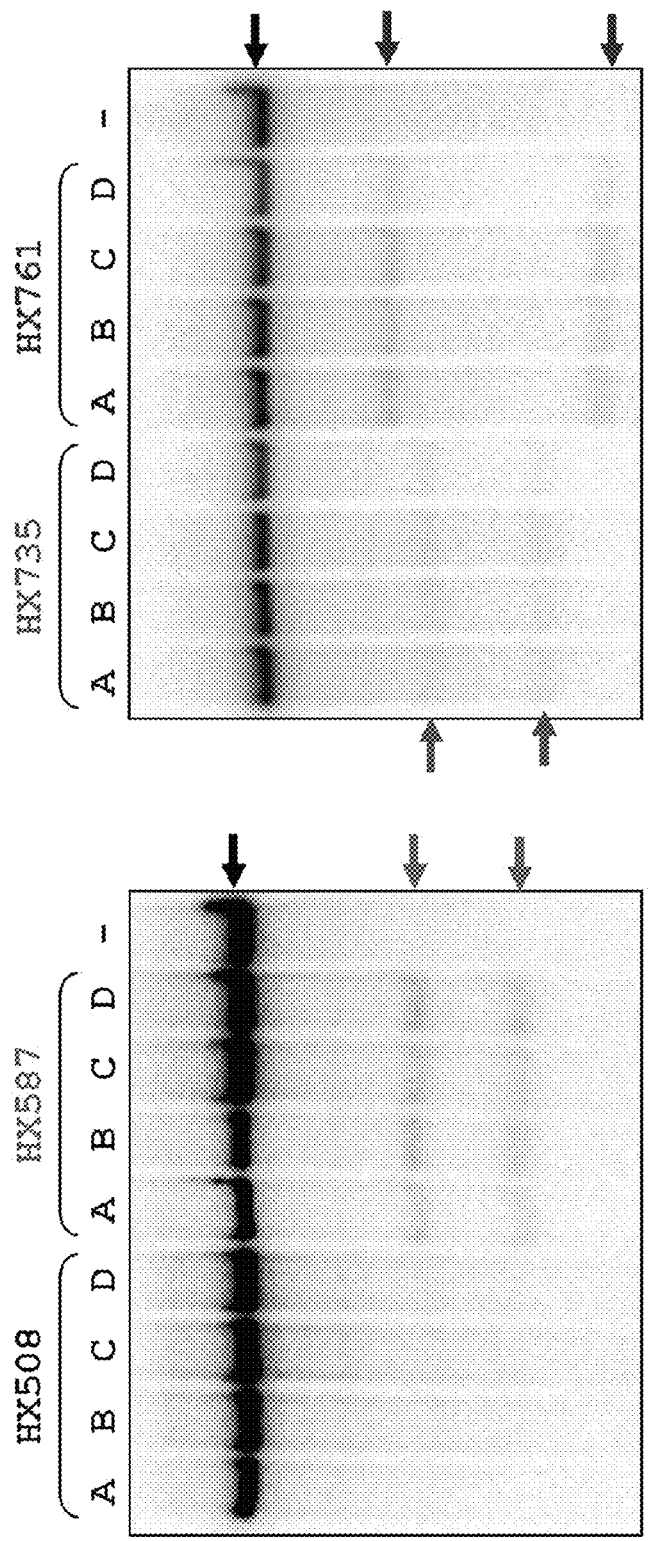

To test whether OPEN ZFNs can induce NHEJ-mediated mutations at the human VEGFA, HoxB13, and CFTR genes, the inventors employed a previously described mutation detection assay which uses the CEL I nuclease to detect ZFN-induced insertions or deletions (Lombardo et al., 2007; Miller et al., 2007). In this assay, limited-cycle PCR is used to amplify a locus of interest from the genomic DNA of a population of human cells transfected with ZFN expression vectors (FIG. 3B). The resulting PCR product is denatured and re-annealed and heteroduplex DNA will form if mutated alleles are present in the population. These DNA fragments can be cleaved at the site of mismatch by the CEL I enzyme into smaller products of predictable size. Using this assay, the inventors found that all four VF2468 and all four VF2471 ZFN pairs induced detectable mutation of the endogenous VEGF-A gene promoter in human 293 cells (FIG. 3C). None of the VF3537, VF3542, or VF3552 ZFN pairs induced detectable levels of mutation. In addition, mutations could be detected at the endogenous HoxB13 gene in 293 cells for all ZFN pairs tested at the HX587, HX735 and HX761 sites (FIG. 3D). No evidence of mutations was observed for any pairs tested at the HX508 site. DNA sequencing of HoxB13 alleles from cells modified by the HX587 and HX761 confirmed the presence of mutations at the appropriate ZFN cleavage site (data not shown and below). Due to the presence of a polymorphism in the middle of the CF877 site in both human 293 and K562 cells, the inventors could not assess the activity of the CF877 ZFN pairs (data not shown).

Figure 3E:
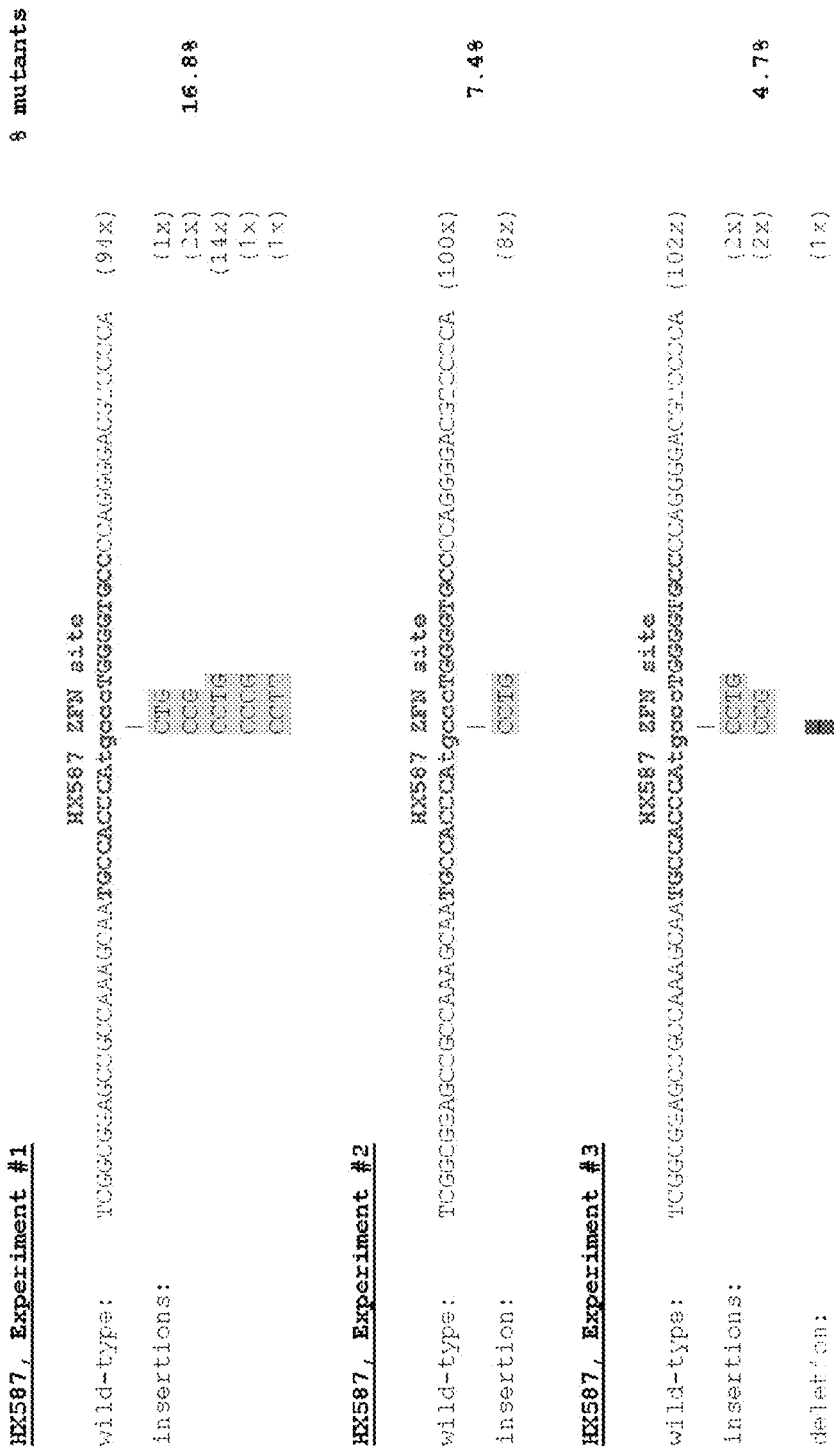
Figure 3F:
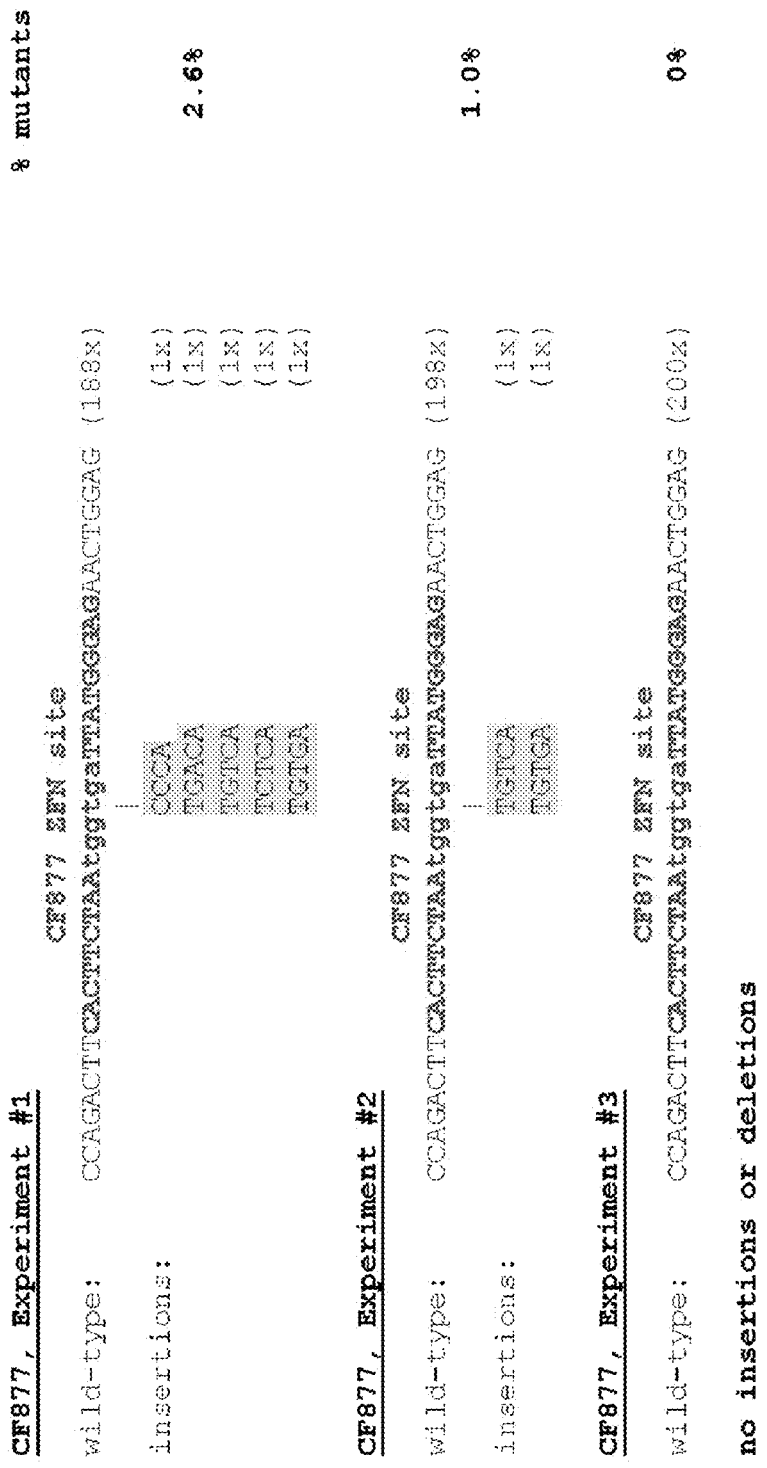

Although previous reports suggested that the CEL I assay can be used to quantify mutations in a population of alleles (Lombardo et al., 2007; Miller et al., 2007), in the inventors' hands this assay did not behave in a reproducibly quantitative manner. Therefore, they instead assessed the frequency of mutations induced by the OPEN ZFNs using a combination of limited-cycle PCR and DNA sequencing (see above). HX587 ZFN pair B and the CF877 ZFN pair were chosen for quantification. Insertion and deletion mutations were observed at the expected location in the middle of the HX587 site with an average frequency of 9.6% (FIG. 3E). For the CFTR locus, insertions at the CF877 cleavage site were observed with an average frequency of 1.2% (FIG. 3F), providing evidence that this pair of ZFNs was active in human cells. These mutation frequencies induced by OPEN ZFNs are comparable to rates of NHEJ-mediated mutation induced by ZFNs targeted to the human IL2Rγ gene in a previous study (Lombardo et al., 2007).

To test whether OPEN ZFNs function effectively in cells other than human, the inventors sought to modify an endogenous gene in plants. Tobacco protoplasts were transformed with a construct encoding the SR2163 ZFN pair as well as a construct that expresses kanamycin resistance (to identify cells successfully transformed with exogenous DNA). Kanamycin-resistant cells were selected and regenerated into individual plants, and the SR2163 site in each plant was examined for evidence of cleavage in both SuRA and SuRB using PCR amplification and DNA sequencing. Among 66 transgenic plants surveyed, three had mutations in SuRA, all of which were deletions of a single base (FIG. 3G). In one plant, both alleles of SuRA had the same deletion. This frequency of mutagenesis by NHEJ (~2% of potential target alleles) is comparable to what the inventors observed for other OPEN ZFNs in human cells.

OPEN ZFNs Induce Highly Efficient Gene Targeting of Endogenous Human Genes.

Figure 4A:
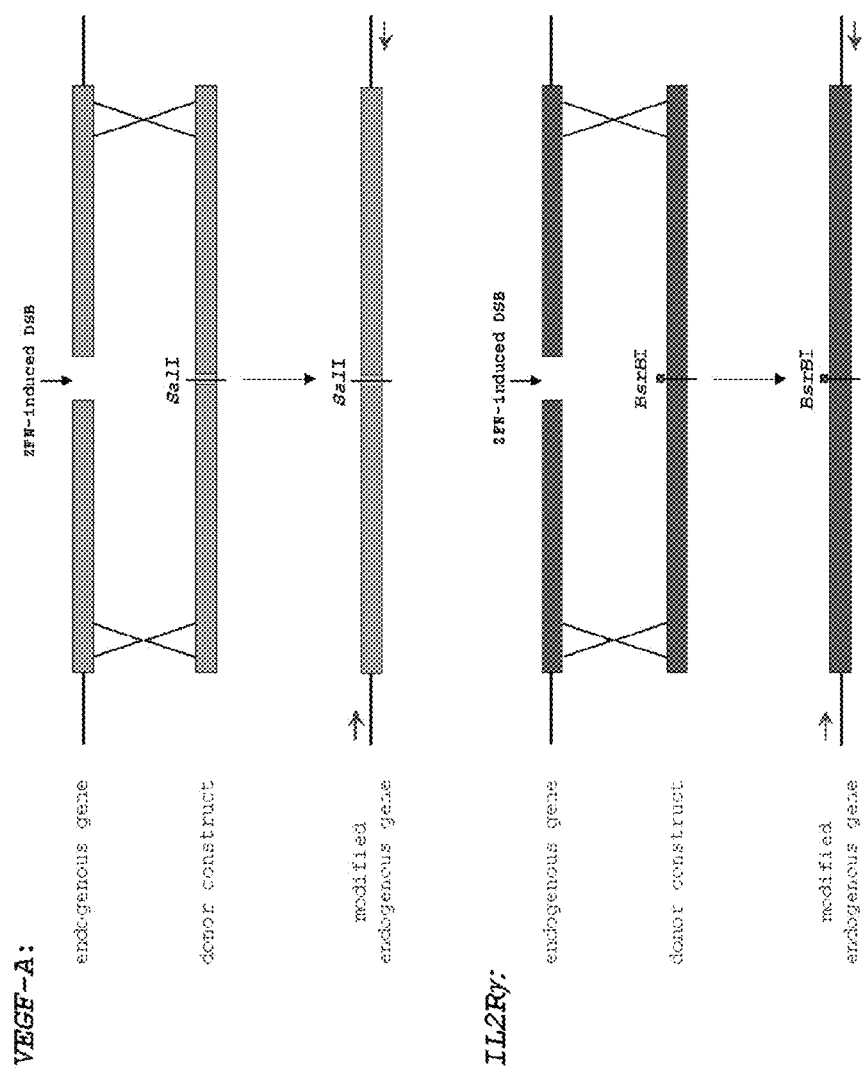
FIGS. 4A-K—Highly efficient gene targeting of endogenous human loci by OPEN ZFNs.
Figure 4B:
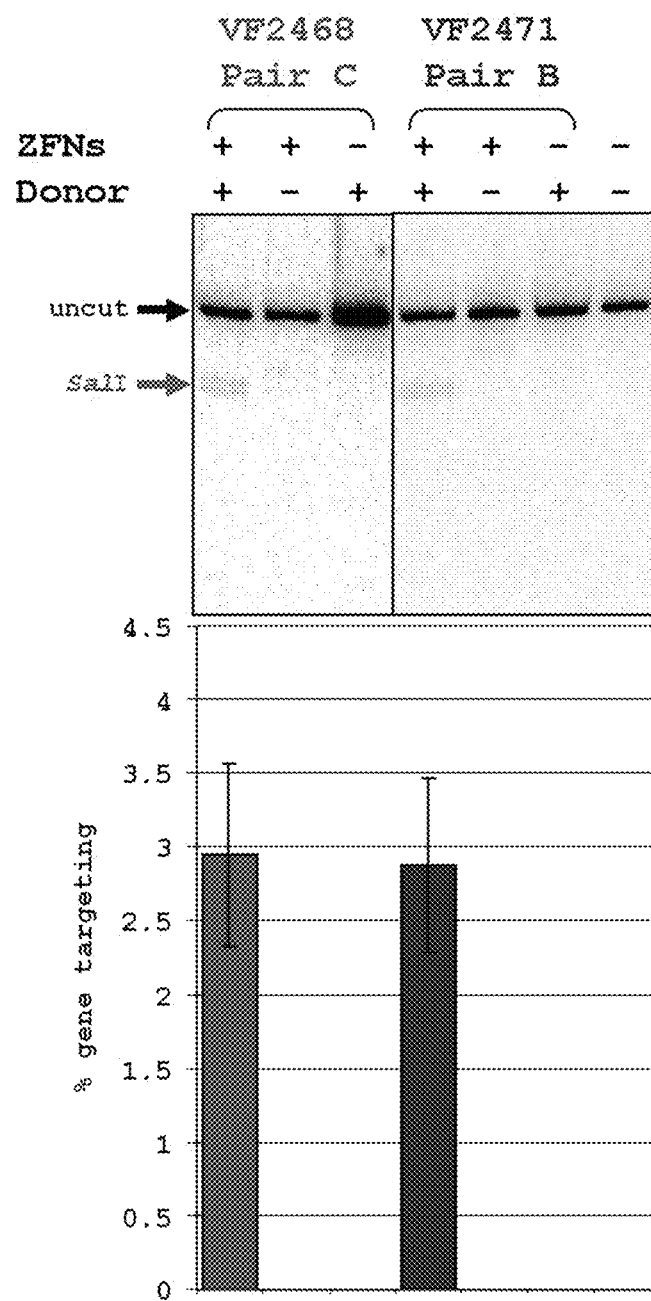

The inventors next tested whether their OPEN ZFNs could be used to induce high efficiency gene targeting at the endogenous VEGF-A gene in human 293 cells. For all gene targeting experiments performed, the inventors used a single ZFN pair for each of the two different target sites: VF2468 pair C and VF2471 pair B. They also constructed appropriate "donor templates" for the VF2468 and VF2471 sites which each contain 1.5 kb of genomic DNA sequence centered on the cleavage site and introduce an 11 bp insertion encoding a SalI restriction site at the center of the cleavage site (FIG. 4A). 293 cells were transfected with expression plasmids encoding ZFN expression vectors and the appropriate donor plasmid and the frequency of successful gene targeting was measured three days post-transfection using a previously described limited-cycle PCR/restriction digest assay (see above) (Urnov et al., 2005). Mean gene targeting frequencies of 2.95% and 2.88% were obtained with the VF2468 and VF2471 ZFN pairs, respectively, with controls demonstrating the requirement for both the donor plasmid and ZFN expression plasmids (FIG. 4B).

Figure 4C:
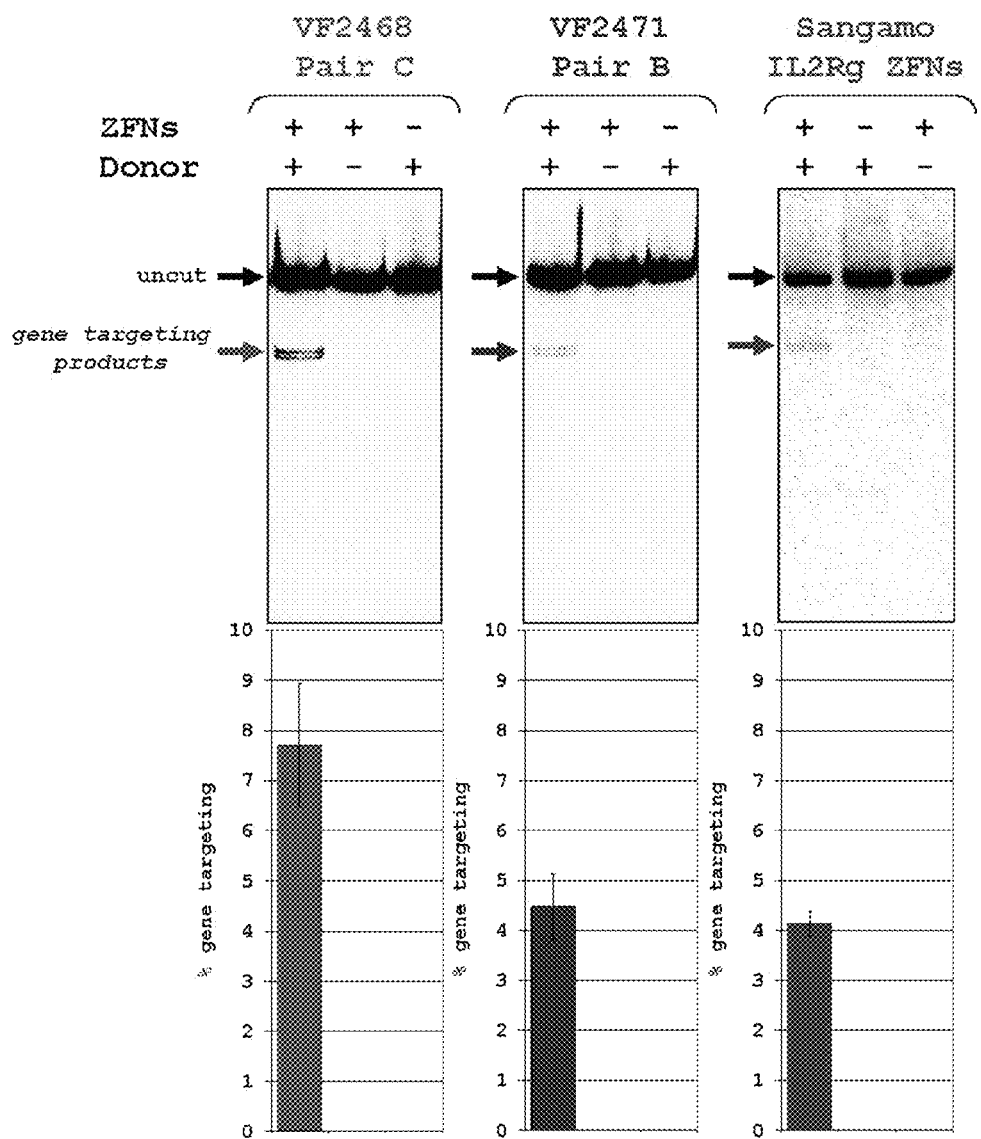
Figure 4D:
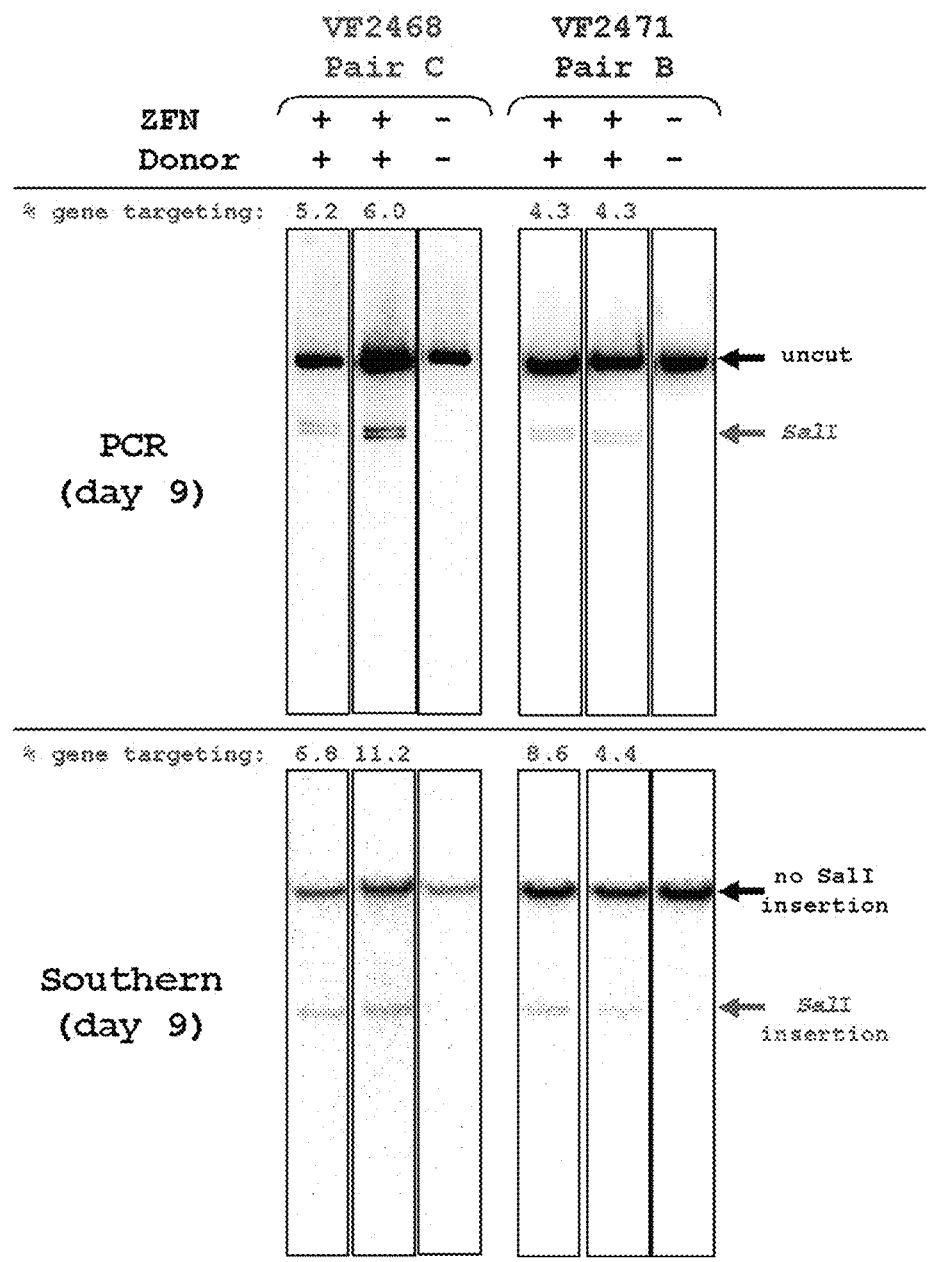
Figure 4E:
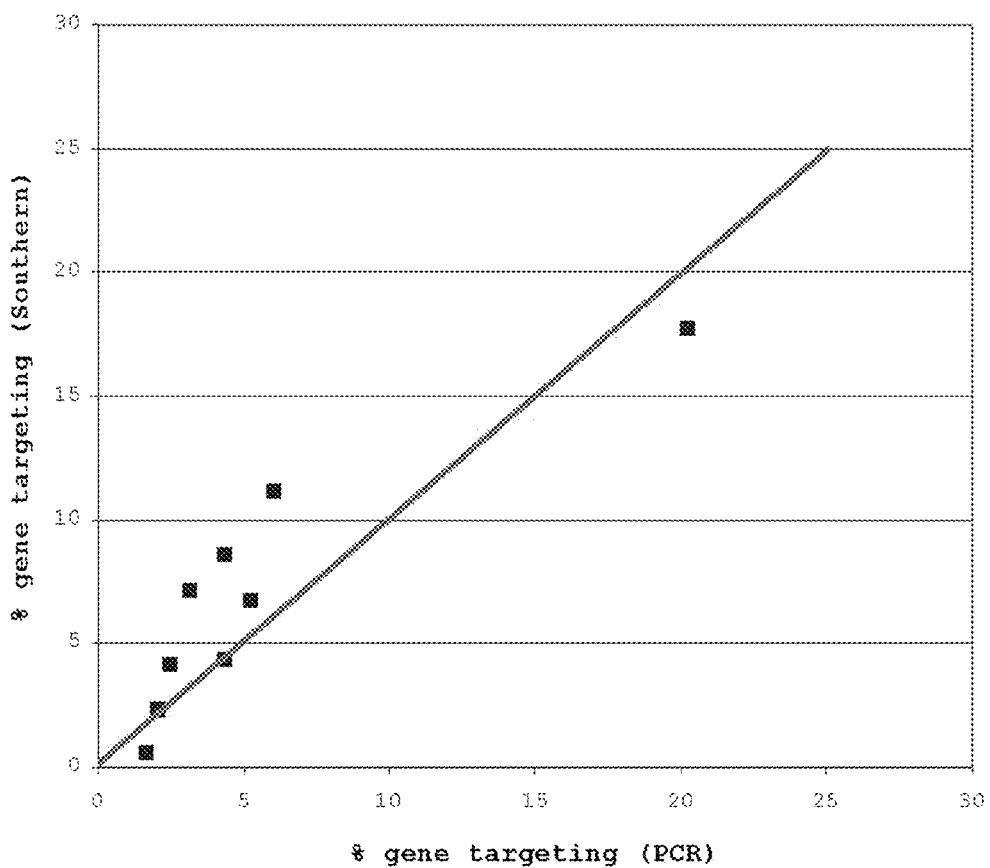

The inventors also tested whether their VF2468 and VF2471 ZFN pairs could mediate high efficiency gene targeting in K562 cells, another human cell line. To perform a side-by-side comparison with a previously published IL2Rγ-specific ZFN pair (Miller et al., 2007), the inventors cloned DNA sequences encoding these nucleases into the ZFN expression vectors and also constructed a donor plasmid containing 1.5 kb of genomic IL2Rγ sequence centered on a translationally silent point mutation that creates a BsrBI restriction site at the ZFN cleavage site (Urnov et al., 2005) (FIG. 4A). Mean gene targeting efficiencies of 7.7%, 4.5% and 4.1% were observed with the VF2468, VF2471, and IL2Rγ ZFNs, respectively (FIG. 4C). The IL2Rγ ZFNs induced gene targeting rates similar to those previously published (Urnov et al., 2005). Increasing the concentrations of ZFN expression vectors and donor plasmid did not appreciably improve gene targeting efficiencies for any of the three pairs tested (data not shown). Control experiments demonstrated that efficient gene targeting required the presence of both the donor construct and ZFN expression vectors (FIG. 4C). To confirm that the results accurately quantified gene targeting frequencies, the inventors performed both PCR-based assays and Southern blotting on genomic DNA harvested from cells modified by VF2468 and VF2471 ZFNs. The two methods gave similar results, but the PCR-based assay tended to underestimate gene targeting rates relative to Southern blots (FIGS. 4D and 4E). They conclude that the IL2Rγ-specific ZFNs and the OPEN VEGF-A ZFNs induce comparable gene targeting frequencies in human cells.

Figure 4F:
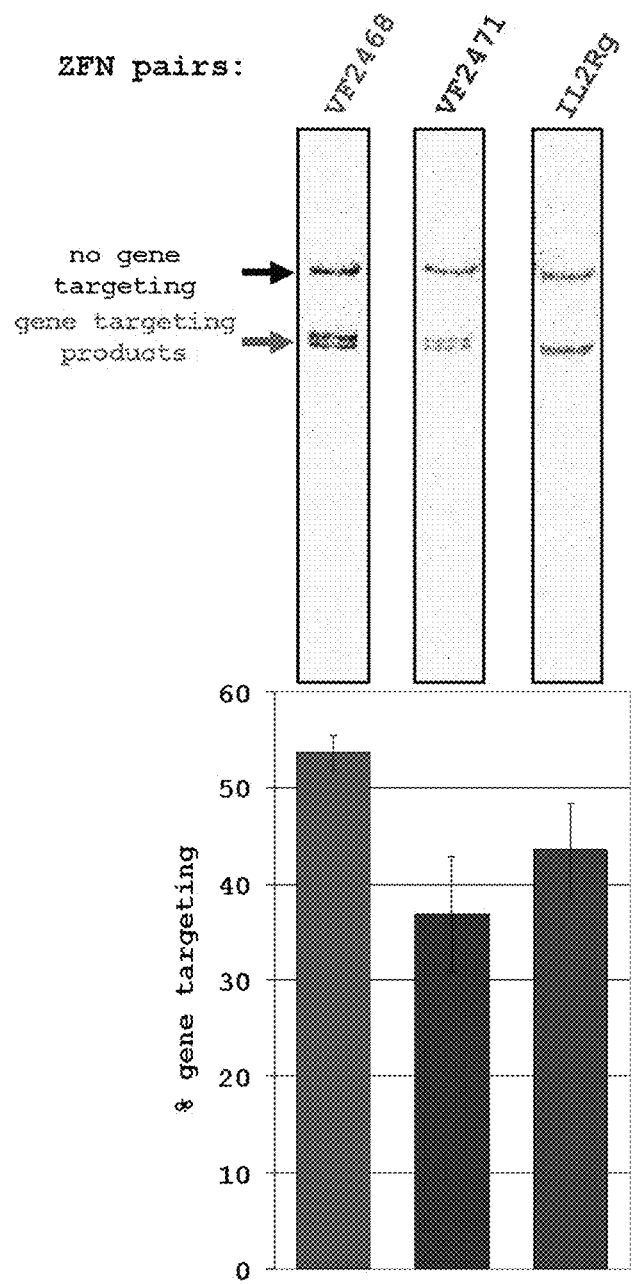
Figure 4G:
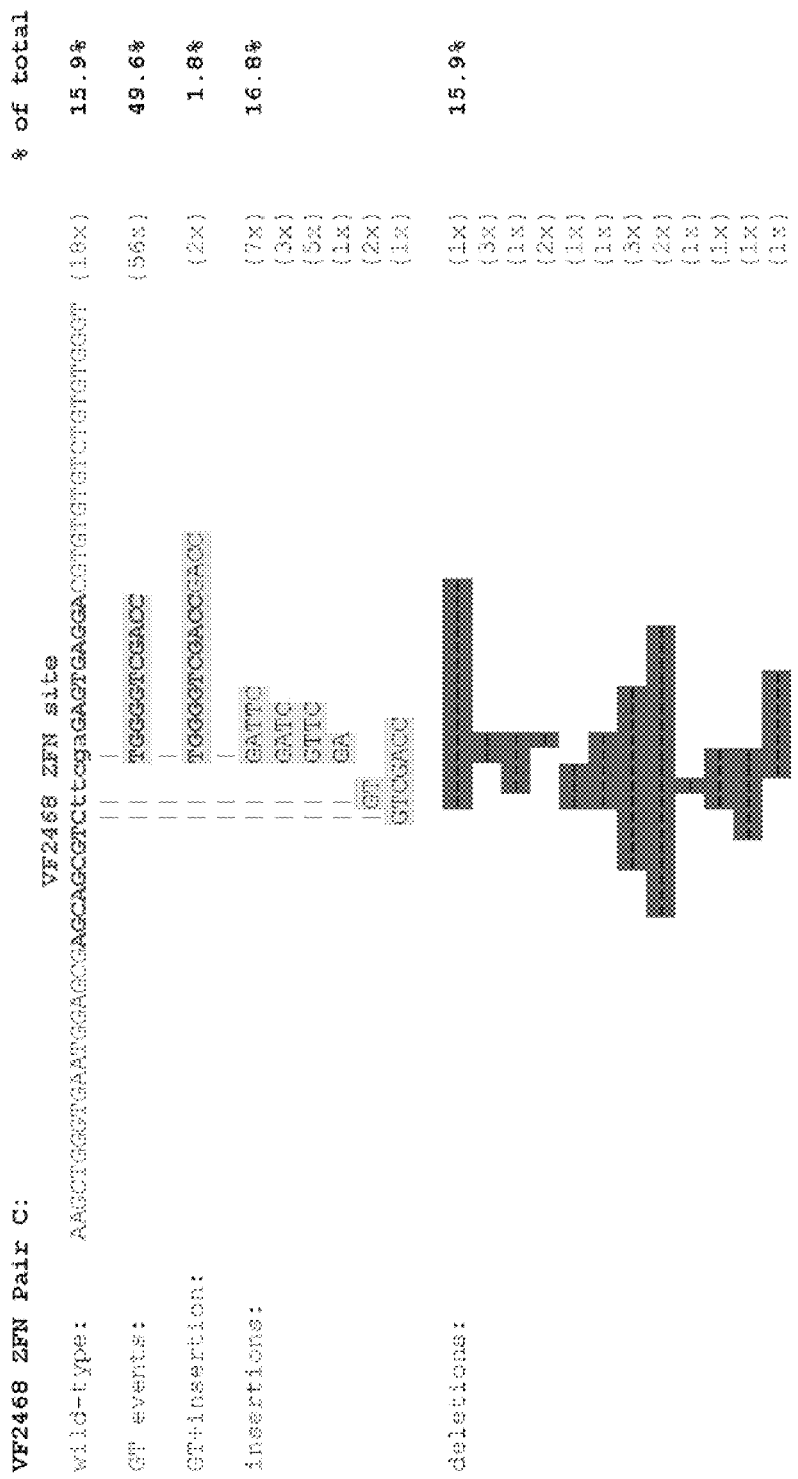
Figure 4H:
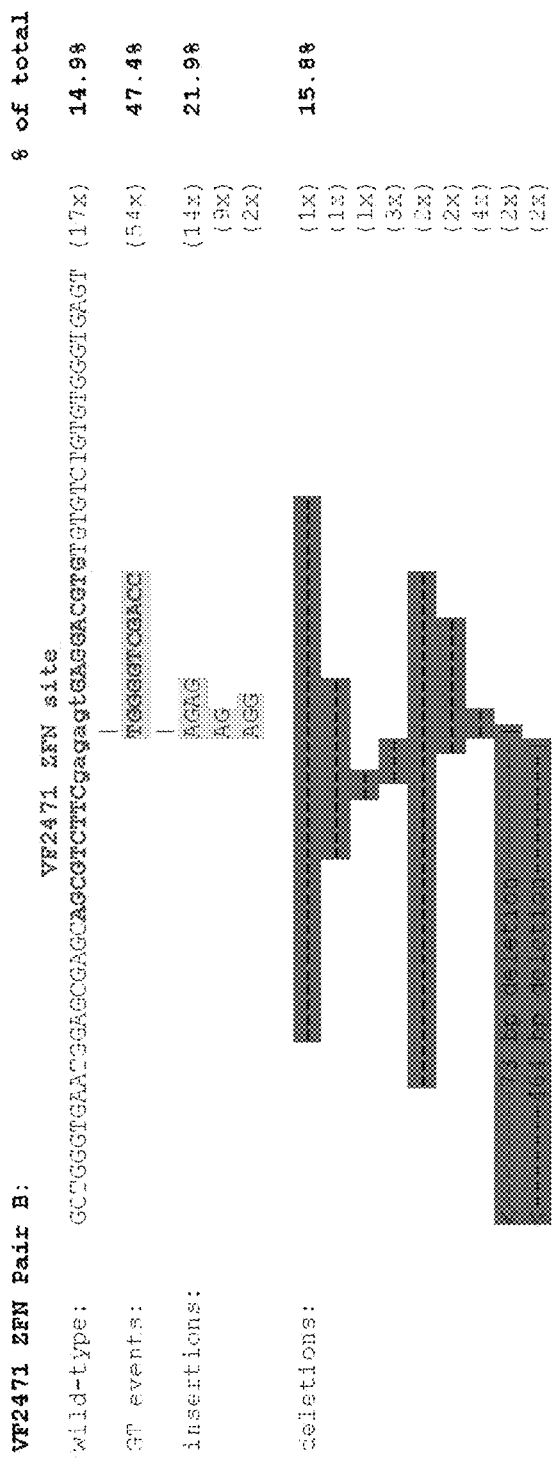
Figure 4I:
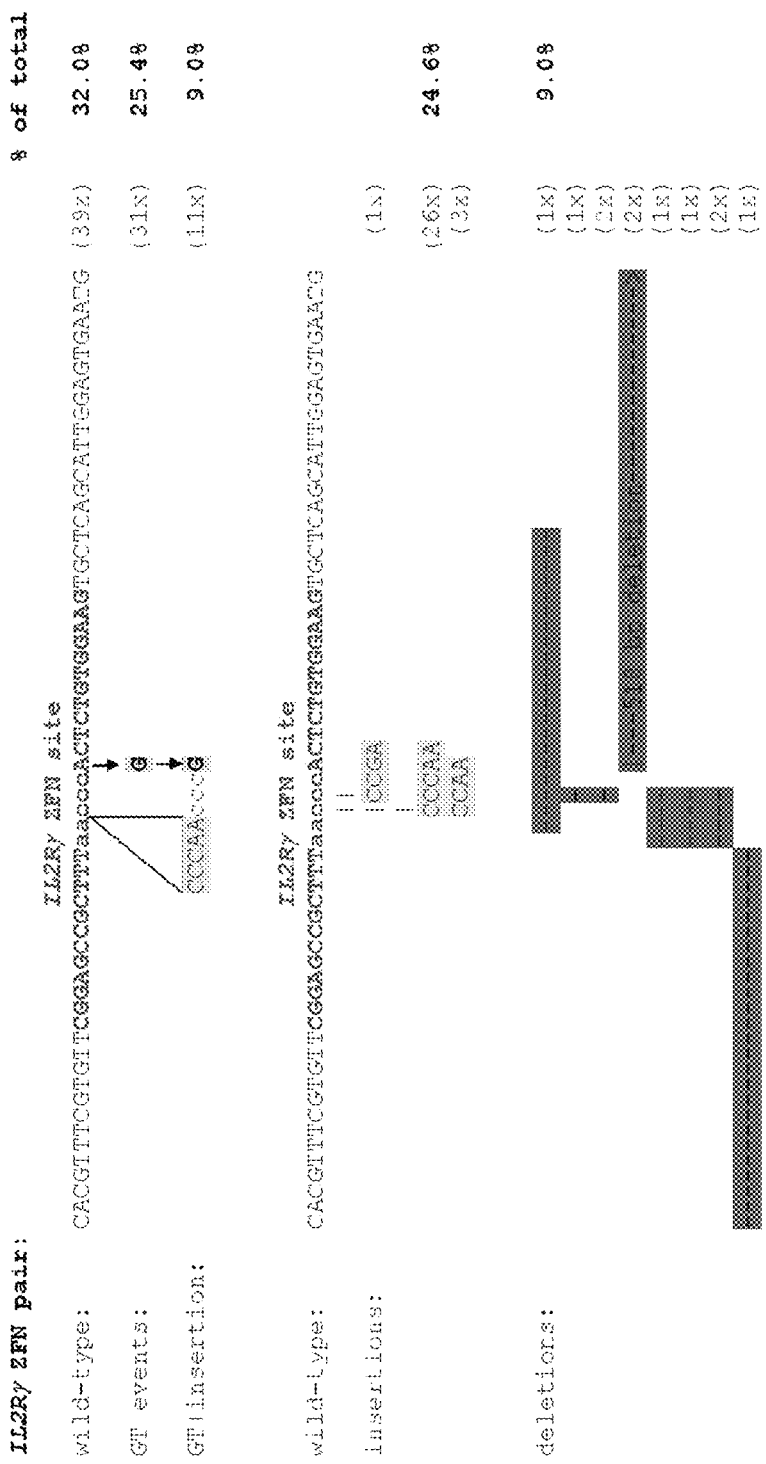

In a previous study, higher rates of gene targeting were observed if cells were transiently arrested in G2 phase with vinblastine (Urnov et al., 2005). The inventors also observed ~8-fold higher rates of gene targeting in vinblastine-treated K562 cells assayed at four days posttransfection with the limited-cycle PCR/restriction digest assay: 54%, 37%, and 44% mean gene targeting efficiencies with VF2468, VF2471, and IL2Rγ ZFNs, respectively (FIG. 4F). Notably, however, vinblastine treatment greatly reduced the number of viable cells. Sequencing of VEGF-A or IL2Rγ alleles amplified from genomic DNA of these vinblastine-treated cells revealed gene targeting events at the expected locations and with frequencies that matched well with the results of limited-cycle PCR assays (FIGS. 4G-4I). For all three target sites, the inventors also observed high frequencies of insertion and deletion events at the ZFN cleavage sites, presumably caused by error-prone NHEJ.

Unexpectedly, the inventors found that 1.8% and 9.0% of the alleles from cells treated with VF2468 and IL2Rγ ZFNs, respectively, contained evidence of both gene targeting and NHEJ-mediated insertion events at a single allele. They note that these doubly altered alleles could only be found by sequencing and would not have been detected in previously published studies that used PCR-based or Southern blot assays to detect gene targeting events (Lombardo et al., 2007; Urnov et al., 2005).

Toxicity Profiles of OPEN ZFNs.

Figure 4J:
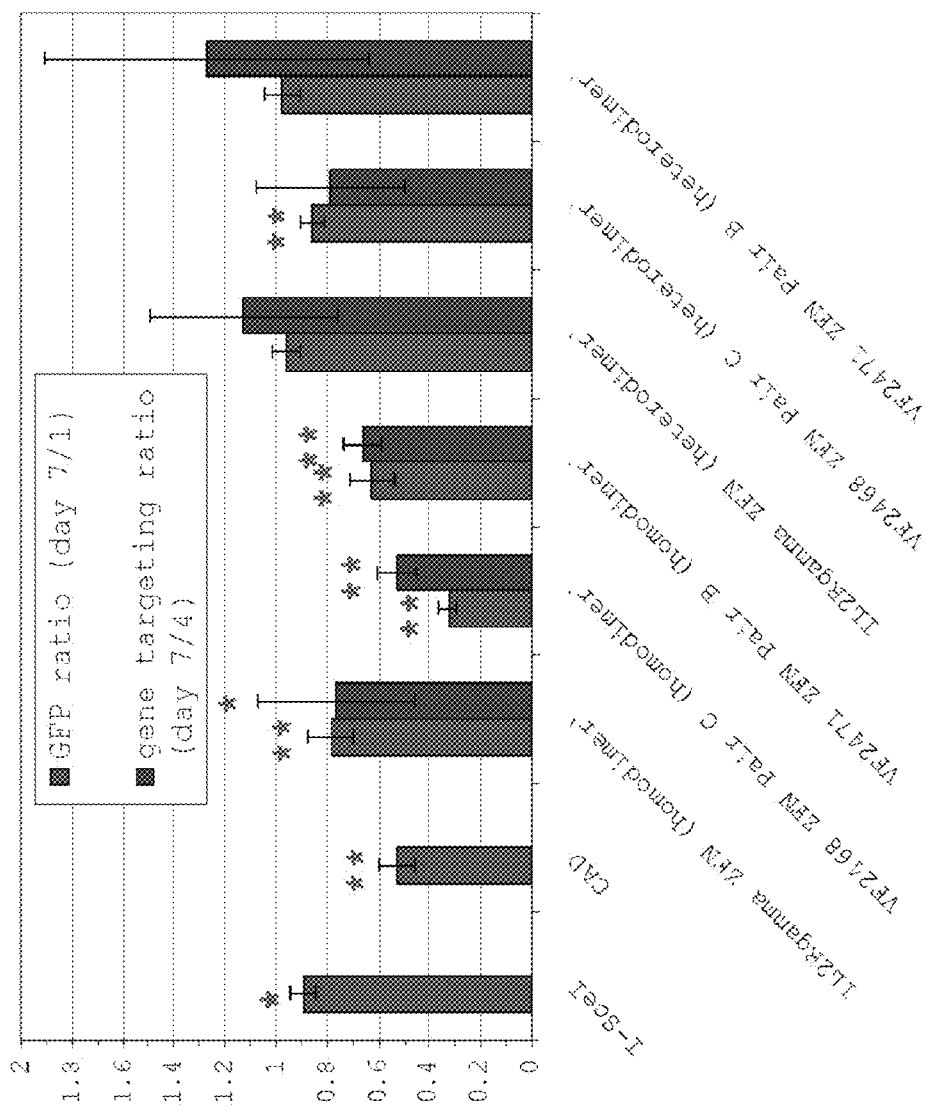

Some three-finger ZFNs made by modular assembly or rational design can cause cellular toxicity, an effect most likely due to unintended, off-target cleavage events (Cornu et al., 2008; Porteus and Baltimore, 2003). By contrast, optimized IL2Rγ-targeted ZFNs, which possess four-finger arrays, cause minimal toxicity (Miller et al., 2007; Urnov et al., 2005). The inventors therefore wished to compare the relative toxicities of the three-finger OPEN VEGF-A ZFNs with the four-finger IL2Rγ ZFNs. Cell survival assays were conducted in which K562 cells were transfected with ZFN expression vector pairs, an appropriately matched donor plasmid, and a plasmid expressing GFP. GFP-positive cells were assayed 1 and 7 days post-transfection and the percentage of gene targeting events was assessed 4 and 7 days post-transfection. Previous studies have demonstrated that toxic ZFNs reduce the percentage of GFP-positive cells (Cornu et al., 2008; Pruett-Miller et al., 2008) and the percentage of cells that have undergone a gene targeting event (Porteus and Baltimore, 2003) over time. All three ZFN pairs showed significant reductions in the relative number of GFP-positive cells by post-transfection day 7, with the IL2Rγ and VF2471 ZFN pairs exhibiting similar levels of toxicity and the VF2468 ZFN pair exhibiting a greater level of toxicity which rivaled that induced by the control CAD (caspase-activated DNase) protein (FIG. 4J, green bars). As expected, analogous decreases were also observed in the percentage of gene targeting events measurable in the cell populations (FIG. 4J, purple bars).

Figure 4K:
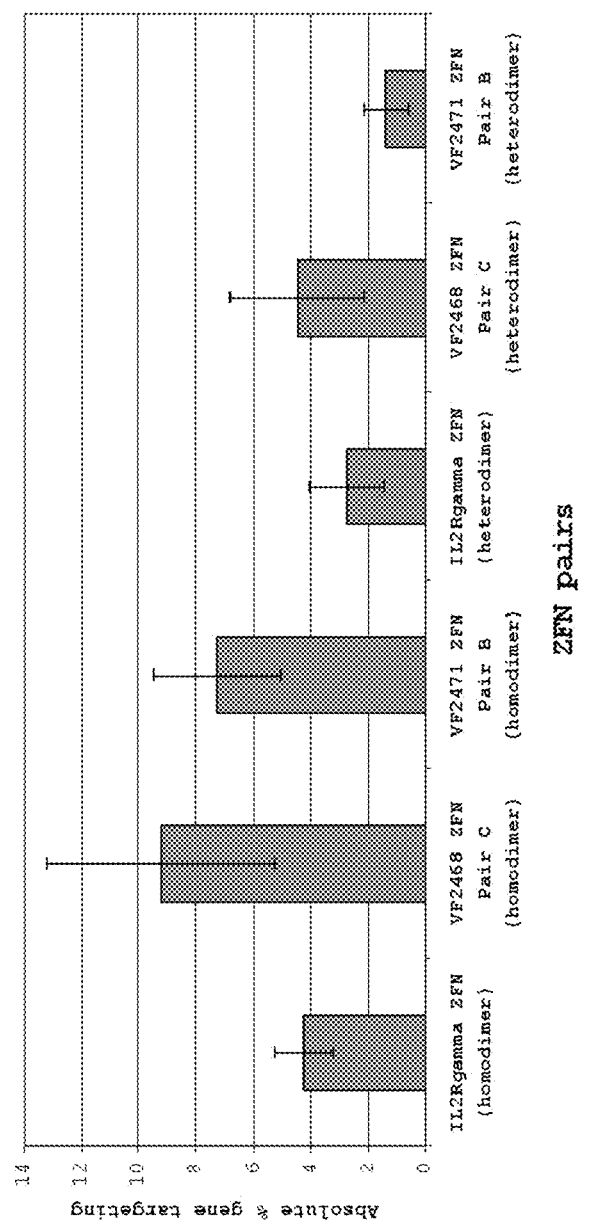

The use of obligate heterodimeric FokI nuclease domain variants can significantly reduce ZFN-associated toxicity (Miller et al., 2007; Szczepek et al., 2007). The inventors examined the toxicities of the Sangamo IL2Rγ and the OPEN VF2468 and VF2471 ZFNs harboring these variant FokI domains. Both the variant IL2Rγ ZFN pair and the variant VF2471 ZFN pair showed no significant toxicity as judged by the GFP toxicity assay (FIG. 4J, green bars). In addition, the variant VF2468 ZFN pair revealed minimal toxicity (FIG. 4J) of a level comparable to that of I-SceI, a highly specific meganuclease used as a "nontoxic" control in previous studies (Porteus and Baltimore, 2003). Comparable effects were also observed for these variant nucleases when examining the relative percentage of gene targeting events in the cell populations (FIG. 4J, purple bars). The absolute gene targeting frequencies induced by the three variant ZFN pairs were comparable at day 4 (FIG. 4K), demonstrating that the absence of observable toxicity is not due to lack of ZFN activity. The inventors conclude that the three-finger OPEN ZFNs can exhibit toxicity profiles comparable to that of an optimized four-finger ZFN, particularly when they are expressed in an obligate heterodimer framework.

OPEN ZFNs Mediate Stable Multi-Allelic Changes in Human Cells.

To test whether OPEN ZFN-induced gene targeting events are stably maintained, limiting dilution cloning was used to isolate single cell clones from K562 cell populations that had been modified with homodimeric VF2468 or VF2471 ZFNs. 30 days following transfection, two vinblastine-treated K562 cell populations showed high frequencies of gene targeting: 45% and 26% with the VF2468 and VF2471 ZFN pairs, respectively (FIG. 5A). Of note, the VF2468 ZFN-treated cells also showed evidence of a 625 bp deletion (FIG. 5A, blue asterisks), a finding confirmed by sequencing of alleles from these cells (data not shown). FISH analysis indicated that K562 cells harbor four alleles of the VEGF-A gene (FIG. 5B), and the inventors therefore wished to determine how many of these alleles were altered in individual cells within the population. Using dilution cloning, the inventors isolated 27 and 28 single cell clones for the VF2468 and VF2471 ZFN-treated cell populations, respectively. Genotype analysis of individual clones from the VF2471 ZFN-treated cells revealed clones in which no, one, two, or three VEGF alleles had undergone a gene targeting event (FIG. 5A, lower right panel). Individual clones from VF2468 ZFN-treated cells harbored no, one, three, or four alleles that had undergone a gene targeting event with some of the clones also containing the 625 bp deletion (FIG. 5A, lower left panel). All individual cell clones were genotyped more than forty days post-transfection, demonstrating that gene targeting events the inventors observed are stably maintained. As a control, they performed FISH analysis on three clones in which all VEGF-A alleles in each cell had undergone the VF2468 ZFN-induced gene targeting event and confirmed the continued presence of four copies of VEGF-A per cell (FIG. 5B). Taken together, these results demonstrate that OPEN ZFNs can be used to induce permanent alterations in as many as four alleles in a single human cell.

Using Zinc Finger Nucleases (ZFNs) constructed by the methods above, the inventors generated ZFN pairs that bind to the CFTR gene and create double-strand breaks (DSBs) at a site 123 nucleotides from the ΔF508 deletion (Tables 1-2). To assess whether these ZFNs could introduce targeted DSBs within the endogenous human CFTR gene, the inventors looked for the introduction of small insertions or deletions (indels) which result from error-prone repair by non-homologous end joining (NHEJ). When they introduced plasmids encoding ZFNs by nucleofection, the rate of NHEJ-mediated indels observed was 1.2% as assessed by DNA sequencing.

TABLE 1A

CFTR ZINC FINGER DOMAINS (LEFT ARM)

| | GTG | GAA | TTA | | | |
|---|---|---|---|---|---|---|
| OZ107CF877L 2-step gradient | RKHILDT (SEQ ID NO: 3) | QGGNLVR (SEQ ID NO: 4) | QQTGLAA (SEQ ID NO: 5) | 1.92 | 0.58 | + |
| OZ108CF877L 2-step gradient | RKSVLLV (SEQ ID NO: 6) | QGGNLVR (SEQ ID NO: 7) | QTTGLKS (SEQ ID NO: 8) | 2.31 | 0.51 | |
| OZ109CF877L 2-step gradient | RTSSLKR (SEQ ID NO: 9) | RREHLTR (SEQ ID NO: 10) | QPTGLTA (SEQ ID NO: 11) | 2.83 | 0.20 | |
| OZ110CF877L 2-step gradient | RNFILQR (SEQ ID NO: 12) | QGGNLVR (SEQ ID NO: 13) | QVNGLKA (SEQ ID NO: 14) | 1.61 | 0.15 | + |
| OZ111CF877L 2-step gradient | RKGVLRI (SEQ ID NO: 15) | QGGNLVR (SEQ ID NO: 16) | QQTGLNV (SEQ ID NO: 17) | 2.20 | 1.90 | + |
| OZ112CF877L 2-step gradient | RTSSLKR (SEQ ID NO: 18) | RREHLTR (SEQ ID NO: 19) | QPTGLTA (SEQ ID NO: 20) | 2.52 | 0.55 | |
| OZ113CF877L 2-step gradient | RKSVLHN (SEQ ID NO: 21) | QGGNLVR (SEQ ID NO: 22) | QTTGLKS (SEQ ID NO: 23) | 1.61 | 0.20 | |
| OZ114CF877L 2-step gradient | RNFILQR (SEQ ID NO: 24) | QGGNLVR (SEQ ID NO: 25) | QQTGLAA (SEQ ID NO: 26) | 2.95 | 0.18 | |
| OZ115CF877L 2-step gradient | RNFILQR (SEQ ID NO: 27) | QGGNLVR (SEQ ID NO: 28) | QVNGLKA (SEQ ID NO: 29) | 2.71 | 0.12 | |
| OZ116CF877L 2-step gradient | RRHVLER (SEQ ID NO: 30) | QGGNLVR (SEQ ID NO: 31) | QQTGLNV (SEQ ID NO: 32) | 2.53 | 0.38 | |
| OZ117CF877L 2-step gradient | RKSVLLV (SEQ ID NO: 33) | QGGNLVR (SEQ ID NO: 34) | QQTGLAA (SEQ ID NO: 35) | 3.87 | 0.33 | |
| OZ118CF877L 2-step gradient | RNFILQR (SEQ ID NO: 36) | QGGNLVR (SEQ ID NO: 37) | QQTGLNV (SEQ ID NO: 38) | 3.55 | 0.08 | |

TABLE 1B

CFTR ZINC FINGER DOMAINS (RIGHT ARM)

| | GAG | TGG | TTA | | |
|---|---|---|---|---|---|
| OZ119CF877R 2-step gradient | RQSNLSR (SEQ ID NO: 39) | RKEHLDI (SEQ ID NO: 40) | QMTGLNA (SEQ ID NO: 41) | 2.78 | 0.35 |
| OZ120CF877R 2-step gradient | RQSNLAR (SEQ ID NO: 42) | RKEHLVG (SEQ ID NO: 43) | QASGLNS (SEQ ID NO: 44) | 2.53 | 0.01 |
| OZ121CF877R 2-step gradient | RQSNLSR (SEQ ID NO: 45) | RKEHLSI (SEQ ID NO: 46) | QRTGLTA (SEQ ID NO: 47) | 2.91 | 0.19 |
| OZ122CF877R 2-step gradient | TTHNLMR (SEQ ID NO: 48) | RADHLKV (SEQ ID NO: 49) | QGTGLRA (SEQ ID NO: 50) | 4.72 | 0.59 |
| OZ123CF877R 2-step gradient | TKHNLVR (SEQ ID NO: 51) | RREHLNI (SEQ ID NO: 52) | QTSGLTA (SEQ ID NO: 53) | 5.03 | 0.63 |
| OZ124CF877R 2-step gradient | TKHNLVR (SEQ ID NO: 54) | RREHLNI (SEQ ID NO: 55) | QTSGLTA (SEQ ID NO: 56) | 4.41 | 0.20 |
| OZ125CF877R 2-step gradient | TKHNLVR (SEQ ID NO: 57) | RQEHLNI (SEQ ID NO: 58) | QPTGLKV (SEQ ID NO: 59) | 4.00 | 0.85 |
| OZ126CF877R 2-step gradient | TAHNLMR (SEQ ID NO: 60) | RREHLTI (SEQ ID NO: 61) | QMTGLNA (SEQ ID NO: 62) | 2.57 | 0.28 |
| OZ127CF877R 2-step gradient | RMSNLDR (SEQ ID NO: 63) | RREHLTI (SEQ ID NO: 64) | QGTGLRA (SEQ ID NO: 65) | 1.60 | 0.02 |
| OZ128CF877R 2-step gradient | TTHNLMR (SEQ ID NO: 66) | RKEHLSI (SEQ ID NO: 67) | QMTGLNA (SEQ ID NO: 68) | 2.12 | 0.07 |

TABLE 1B-continued

CFTR ZINC FINGER DOMAINS (RIGHT ARM)

| | | GAG | TGG | TTA | | |
|---|---|---|---|---|---|---|
| OZ129CF877R | 2-step gradient | RQSNLSR (SEQ ID NO: 69) | RKEHLDI (SEQ ID NO: 70) | QMTGLNA (SEQ ID NO: 71) | 2.55 | 0.07 |
| OZ130CF877R | 2-step gradient | RPHNLLR (SEQ ID NO: 72) | RADHLKV (SEQ ID NO: 73) | QTTGLNA (SEQ ID NO: 74) | 2.47 | 0.22 |
| OZ131CF877R | 2-step gradient | KHSNLTR (SEQ ID NO: 75) | RREHLTI (SEQ ID NO: 76) | QPTGLRA (SEQ ID NO: 77) | 2.08 | 0.12 |
| OZ132CF877R | 2-step gradient | RQSNLSR (SEQ ID NO: 78) | RSEHLAI (SEQ ID NO: 79) | QRVGLHA (SEQ ID NO: 80) | 1.28 | 0.05 |
| OZ133CF877R | 2-step gradient | KHSNLTR (SEQ ID NO: 81) | RADHLKV (SEQ ID NO: 82) | QNTGLHA (SEQ ID NO: 83) | 3.24 | 0.05 |
| OZ134CF877R | 2-step gradient | RQSNLSR (SEQ ID NO: 84) | RNEHLVL (SEQ ID NO: 85) | QKTGLRV (SEQ ID NO: 86) | 3.71 | 0.19 |
| OZ135CF877R | 2-step gradient | KHSNLTR (SEQ ID NO: 87) | RREHLTI (SEQ ID NO: 88) | QMTGLNA (SEQ ID NO: 89) | 2.25 | 0.07 |
| OZ136CF877R | 2-step gradient | KHSNLTR (SEQ ID NO: 90) | RREHLTI (SEQ ID NO: 91) | QMTGLNA (SEQ ID NO: 92) | 2.16 | 0.06 |
| OZ137CF877R | 2-step gradient | RHSNLTR (SEQ ID NO: 93) | RQEHLNI (SEQ ID NO: 94) | QMTGLNA (SEQ ID NO:95) | 2.26 | 0.04 |
| OZ138CF877R | 2-step gradient | KKTNLTR (SEQ ID NO: 96) | RREHLTI (SEQ ID NO: 97) | QQTGLNV (SEQ ID NO: 98) | 2.52 | 0.41 |
| OZ139CF877R | 2-step gradient | KHSNLTR (SEQ ID NO: 99) | RKEHLSI (SEQ ID NO: 100) | QMTGLNA (SEQ ID NO: 101) | 2.74 | 0.03 |
| OZ140CF877R | 2-step gradient | KHSNLTR (SEQ ID NO: 102) | RKEHLTI (SEQ ID NO: 103) | QRTGLSI (SEQ ID NO: 104) | 2.99 | 0.48 |
| OZ141CF877R | 2-step gradient | KHGNLTR (SEQ ID NO: 105) | RREHLTI (SEQ ID NO: 106) | QQTGLNV (SEQ ID NO: 107) | 2.87 | 0.08 |
| OZ142CF877R | 2-step gradient | KHSNLTR (SEQ ID NO: 108) | RKEHLDI (SEQ ID NO: 109) | QMTGLNA (SEQ ID NO: 110) | 2.73 | 0.16 |

Figure 8:
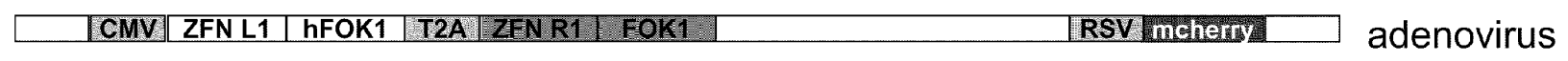

The inventors hypothesized that a viral vector could more efficiently deliver ZFN pairs to airway epithelial cells and thereby improve the observed indel rate. One ZFN was delivered by an adenovirus that also encoded an eGFP reporter gene; and the partner ZFN-encoding adenovirus encoded an mCherry reporter gene (FIG. 8). In both viral vectors, the ZFNs were driven by CMV promoter with the fluorophores driven by the RSV promoter. This approach enabled the inventors to use FACS to quantify the number of cells that express both ZFNs in the pair. Using multiplicities of infection (MOI) of 250 for each virus, they delivered ZFNs to CF bronchial epithelial cells homozygous for the ΔF508 mutation. The inventors found that on average 40% of the cells were doubly-positive for expression of the fluorescent reporter genes. Surveyor nuclease (CEL-1) assays of infected cells (without sorting) showed that ZFNs induced NHEJ-mediated indels with an average efficiency of 6% of alleles.

To further improve the efficiency of ZFN-induced indel formation, the inventors have designed an adenoviral vector expressing a ZFN pair joined by an intervening picornavirus T2A sequence. In addition, to extend results beyond introduction of targeted NHEJ-mediated indels, the inventors have constructed an adenoviral vector carrying a DNA donor repair template for performing homologous recombination-based gene targeting and a Cerulean fluorescent reporter gene driven by RSV. Experiments are underway to transduce CF epithelia with ZFN and donor vectors to stimulate homologous recombination and to thereby correct the ΔF508 locus. In summary, adenoviral delivery of ZFNs improves the efficiency of ZFN delivery to airway epithelial cells, and increases the NHEJ frequency near the ΔF508 locus of CFTR.

Figure 7:
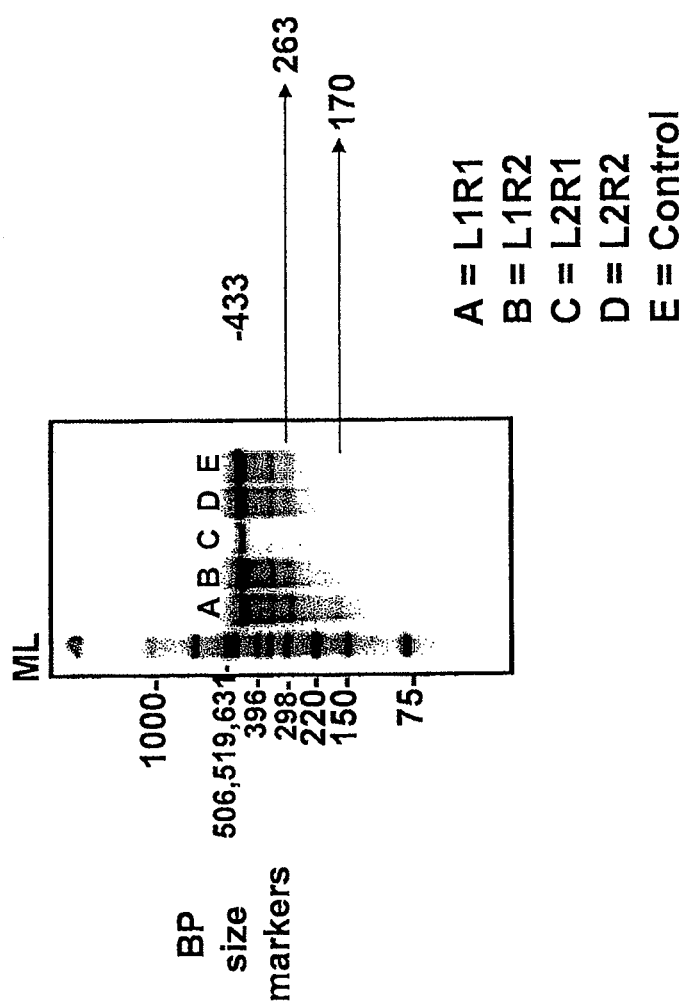
FIG. 7—Surveyor nuclease (Cel I) assay autoradiograph. A CF airway epithelial cell line homozygous for the ΔF508 CFTR mutation was transduced with a serotype 5 adenovirus vector expressing the indicated ZFN pairs (L1R1, L1R2, etc.). Assay performed 72 hr post transduction with adenovirus vector. Expected products following ZFN cleavage are 263 and 170 nt. Experimental conditions indicated for lanes A-E. Signal detected by phosphorimager.
Figure 9:
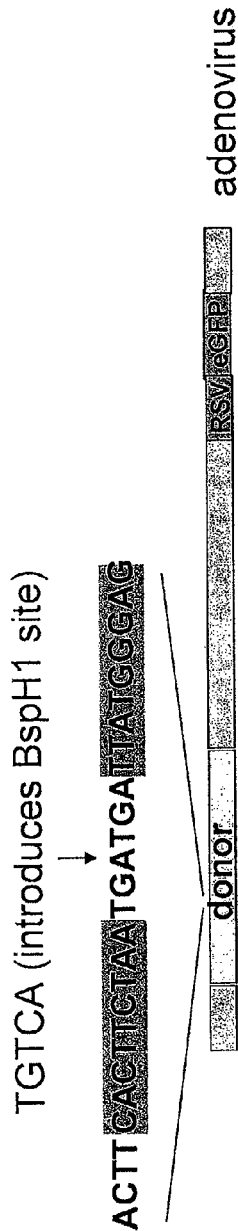
FIG. 9—Repair DNA donor template for exon 10 of CFTR. (SEQ ID NO:130) Donor template is 1320 nucleotides long. 350 nts of left arm and 970 nts of right arm. It is packaged in an adenoviral vector but could be delivered by other vectors (viral or non-viral). The 9 nucleotides highlighted in green on the sequence indicate the regions where the ZFNs bind. In between the two ZFN is a 6-nucleotide spacer. The TGTCA fragment contained in the donor repair template is introduced between the spacer region TGATGA which will introduce the unique BspH1-TCATGA only in the donor.

The inventors also screened the ZFN pairs for activity by expressing them using adenoviral vectors in CFBE cells (an immortalized human airway epithelial cell line homozygous for the ΔF508 mutation, CFBE41o (CFBE) cells) using the surveyor (Cel I) nuclease assay as described above. As shown in Lane A, the combination of L1, R1 gave the greatest evidence of cutting activity (FIG. 7). The inventors have also generated a donor vector carrying a 1320 kb portion of wild-type CFTR sequence, and an engineered unique restriction site BspH1 into the donor, as well as unique silent mutations (FIG. 9).

FIG. 11A depicts an adenoviral vector expressing the ZFN pair targeting the CF877 site as a single expression cassette with an intervening picornavirus T2A sequence. FIG. 11B shows the frequency of NHEJ increased in a dose-dependent manner from ~10% at MOI of 50 to ~29% at MOI of 250 in CFBE41o-cells.

Figure 12:
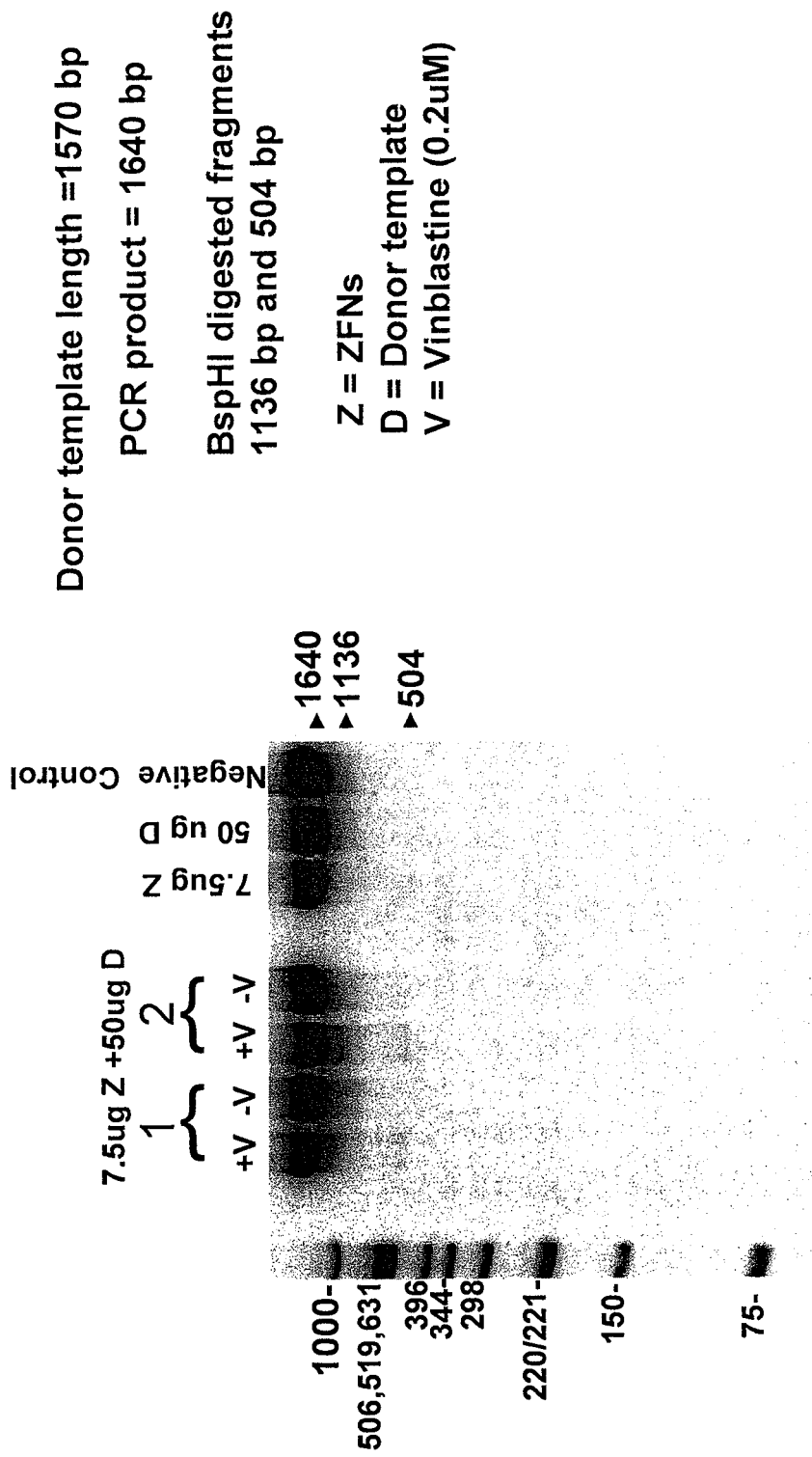
FIG. 12—Radioactive assay for homologous recombination (HR). K-562cells were nucleofected (Amaxa T-16, soln V) with ZFNs and donor DNA or ZFNs only. The donor template is ~1.5 kb and has a 5 bp insertion in spacer region between the ZFN binding site where the ZFNs cleave the genomic DNA. This insertion (TGTCA) creates a unique BspH1 site in the donor. The genomic DNA is harvested 4 days post nucleofection. PCR using primers binding outside of the donor template and radiolabeled dNTPs is followed by BspH I digestion. In the experiments with 24 hrs post nucleofection, the cells were treated with vinblastine (0.2 μM) for 16 hrs. The presence of fragments at 1136 and 504 bp indicates HR. HR was confirmed by DNA sequencing.

FIG. 12 shows a radioactive assay for homologous recombination (HR). K-562cells were nucleofected (Amaxa T-16, soln V) with ZFNs and donor DNA or ZFNs only. The donor template is ~1.5 kb and has a 5 bp insertion in spacer region between the ZFN binding site where the ZFNs cleave the genomic DNA. This insertion (TGTCA) creates a unique BspH1 site in the donor. The genomic DNA is harvested 4 days post nucleofection. PCR using primers binding outside of the donor template and radiolabeled dNTPs is followed by BspH I digestion. In the experiments with '+V', 24 hrs post-nucleofection, the cells were treated with vinblastine (0.2 µM) for 16 hrs. The presence of fragments at 1136 and 504 bp indicates HR. HR was confirmed by DNA sequencing.

Figure 13:
FIG. 13—Radioactive assay for homologous recombination (HR) in epithelia. CFBE (CF ΔF508/ΔF508 bronchial epithelial cells) were co-transduced with adenoviral vectors expressing the ZFN pair (AdZ) and the homologous recombination donor (AdD) or with AdZ only. The donor template is ~1.5 kb and has a 5 bp insertion in spacer region between the ZFN binding sites. This insertion (TGTCA) creates a unique BspH1 site in the donor. The genomic DNA is harvested 4 days post transduction. PCR using primers binding outside of the donor template and radiolabeled dNTPs is followed by BspH I digestion. The presence of fragments at 1136 and 504 bp indicates HR. Direct DNA sequencing also documented HR in cells receiving AdZ and AdD, but not AdZ alone.

FIG. 13 shows a radioactive assay for homologous recombination (HR) in epithelia. CFBE (CF ΔF508/ΔF508 bronchial epithelial cells) were co-transduced with adenoviral vectors expressing the ZFN pair (AdZ) and the homologous recombination donor (AdD) or with AdZ only. The donor template is ~1.5 kb and has a 5 bp insertion in spacer region between the ZFN binding sites. This insertion (TGTCA) creates a unique BspH1 site in the donor. The genomic DNA is harvested 4 days post transduction. PCR using primers binding outside of the donor template and radiolabeled dNTPs is followed by BspH I digestion. The presence of fragments at 1136 and 504 bp indicates HR. Direct DNA sequencing also documented HR in cells receiving AdZ and AdD, but not AdZ alone.

Together, FIGS. 11-13 show that delivery of the ZFN pair targeting exon 10 of CFTR by adenoviral vector dramatically increases the frequency of double stranded breaks as assessed by identification of insertions and deletions at the site of cutting by direct sequencing. In addition, these data now provide evidence of homologous recombination at the CFTR exon 10 site, both in in K562 cells transduced with plasmid vectors and electroporation, and in CF epithelial cells transduced with adenoviral vectors to deliver the donor and the ZFN pair.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

V. REFERENCES

The following references, to the extent that they provide exemplary procedural or other details supplementary to those set forth herein, are specifically incorporated herein by reference:

U.S. Pat. No. 4,683,202
U.S. Pat. No. 4,684,611
U.S. Pat. No. 4,879,236
U.S. Pat. No. 4,952,500
U.S. Pat. No. 5,302,523
U.S. Pat. No. 5,322,783
U.S. Pat. No. 5,384,253
U.S. Pat. No. 5,464,765
U.S. Pat. No. 5,466,468
U.S. Pat. No. 5,538,877
U.S. Pat. No. 5,538,880
U.S. Pat. No. 5,550,318
U.S. Pat. No. 5,563,055
U.S. Pat. No. 5,580,859
U.S. Pat. No. 5,589,466
U.S. Pat. No. 5,591,616
U.S. Pat. No. 5,610,042
U.S. Pat. No. 5,656,610
U.S. Pat. No. 5,702,932
U.S. Pat. No. 5,736,524
U.S. Pat. No. 5,780,448
U.S. Pat. No. 5,789,215
U.S. Pat. No. 5,871,986
U.S. Pat. No. 5,925,565
U.S. Pat. No. 5,928,906
U.S. Pat. No. 5,935,819
U.S. Pat. No. 5,945,100
U.S. Pat. No. 5,981,274
U.S. Pat. No. 5,994,624
U.S. Pat. No. 6,074,674
U.S. Pat. No. 6,270,750
PCT Appln. WO 94/09699
PCT Appln. WO 95/06128
Alwin et al., *Mol. Ther.*, 12:610-617, 2005.
Ausubel et al., In: *Current Protocols in Molecular Biology*, John, Wiley & Sons, Inc, NY, 1994; 1996.
Bae et al., *Nat. Biotechnol.*, 21:275-280, 2003.
Baichwal and Sugden, In: *Gene Transfer*, Kucherlapati (Ed.), Plenum Press, NY, 117-148, 1986.
Beerli and Barbas, *Nat. Biotechnol.*, 20:135-141, 2002.
Beumer et al., *Genetics*, 172:2391-2403, 2006.
Bibikova et al., *Genetics*, 161:1169-1175, 2002.
Bibikova et al., *Science*, 300:764, 2003.
Bryson and Szybalski, *Proc. Natl. Acad. Sci. USA*, 98:14991-14996, 1952.
Carbonelli et al., *FEMS Microbiol. Lett.*, 177(1):75-82, 1999.
Cathomen et al., *Proc. Natl. Acad. Sci. USA*, 98(26):14991-14996. 2001
Chandler et al., *Proc. Natl. Acad. Sci. USA*, 94(8):3596-601, 1997.
Chen and Okayama, *Mol. Cell Biol.*, 7(8):2745-2752, 1987.
Cocea, *Biotechniques*, 23(5):814-816, 1997.
Cornu et al., *Mol. Ther.*, 16:352-358, 2008.
Coupar et al., *Gene*, 68:1-10, 1988.
Durai et al., *Nucleic Acids Res.*, 33:5978-5990, 2005.
Elrod-Erickson et al., *Structure*, 4:1171-1180, 1996.
Fechheimer et al., *Proc Natl. Acad. Sci. USA*, 84:8463-8467, 1987.
Fraley et al., *Proc. Natl. Acad. Sci. USA*, 76:3348-3352, 1979.
Friedmann, *Science*, 244:1275-1281, 1989.
Gopal, *Mol. Cell Biol.*, 5:1188-1190, 1985.
Graham and Van Der Eb, *Virology*, 52:456-467, 1973.
Greisman and Pabo, *Science*, 275:657-661, 1997.
Harland and Weintraub, *J. Cell Biol.*, 101(3):1094-1099, 1985.
Hermonat and Muzycska, *Proc. Natl. Acad. Sci. USA*, 81:6466-6470, 1984.
Horwich et al. *J. Virol.*, 64:642-650, 1990.
Hurt et al., *Proc. Natl. Acad. Sci. USA*, 100:12271-12276, 2003.
Inouye and Inouye, *Nucleic Acids Res.*, 13:3101-3109, 1985.
Isalan and Choo, *Methods Enzymol.*, 340:593-609, 2001.
Isalan et al., *Biochemistry*, 37:12026-12033, 1998.
Isalan et al., *Nat. Biotechnol.*, 19:656-660, 2001.
Jasin, *Trends Genet.*, 12:224-228, 1996.
Joung et al., *Proc. Natl. Acad. Sci. USA*, 97:7382-7387, 2000.
Kaeppler et al., *Plant Cell Reports*, 9:415-418, 1990.
Kaneda et al., *Science*, 243:375-378, 1989.

Kato et al, *J. Biol. Chem.*, 266:3361-3364, 1991.
Lee et al., *Embo J.*, 7:1241-1248, 1988.
Levenson et al., *Hum. Gene Ther.*, 9(8):1233-1236, 1998.
Liu et al., *J. Biol. Chem.*, 277:3850-3856, 2002.
Lloyd et al., *Proc. Natl. Acad. Sci. USA*, 102:2232-2237, 2005.
Lombardo et al., *Nat. Biotechnol.*, 25:1298-1306, 2007.
Ma et al., *Cancer Cell*, 5:607-616, 2004.
Ma et al., *J. Clin. Oncol.*, 24: 4611-4619, 2006.
Macejak and Sarnow, *Nature*, 353:90-94, 1991.
Mandell and Barbas, *Nucleic Acids Res.*, 34:W516-523, 2006.
McCourt et al., *Proc. Natl. Acad. Sci. USA*, 103:569-573, 2006.
Miller et al., *Nat. Biotechnol.*, 25:778-785, 2007.
Moehle et al., *Proc. Natl. Acad. Sci. USA*, 104:3055-3060, 2007.
Morton et al., *Proc. Natl. Acad. Sci. USA*, 103:16370-16375, 2006.
Nicolas and Rubinstein, In: *Vectors: A survey of molecular cloning vectors and their uses*, Rodriguez and Denhardt, eds., Stoneham: Butterworth, 494-513, 1988.
Nicolau and Sene, *Biochim. Biophys. Acta,* 721:185-190, 1982.
Nicolau et al., *Methods Enzymol.*, 149:157-176, 1987.
Omirulleh et al., *Plant Mol. Biol.*, 21(3):415-428, 1993.
Pelletier and Sonenberg, *Nature*, 334(6180):320-325, 1988.
Porteus and Baltimore, *Science*, 300:763, 2003.
Porteus and Carroll, *Nat. Biotechnol.*, 23:967-973, 2005.
Potrykus et al., *Mol. Gen. Genet.*, 199(2):169-177, 1985.
Pruett-Miller et al., *Molec. Therapy*, 16(4):707-17, 2008.
Ramirez et al., *Nature Methods,* 5(5):374-375, 2008.
Remington's Pharmaceutical Sciences, 18th Ed., Mack Printing Company, 1289-1329, 1990.
Remington's Pharmaceutical Sciences" 15th Ed., Mack Printing Company, 1035-1038 and 1570-1580, 1990.
Ridgeway, In: *Vectors: A Survey of Molecular Cloning Vectors and Their Uses*, Rodriguez et al. (Eds.), Stoneham: Butterworth, 467-492, 1988.
Rippe, et al., *Mol. Cell Biol.*, 10:689-695, 1990.
Sambrook et al., In: *Molecular cloning: a laboratory manual*, 2nd Ed., Cold Spring Harbor Laboratory Press, Cold Spring Harbor, N.Y., 1989.
Sander et al., *Nucleic Acids Res.*, 35:W599-605, 2007.
Scott, *Nat. Biotechnol.*, 23:915-918, 2005.
Segal et al., *Biochemistry*, 42:2137-2148, 2003.
Segal, *Methods*, 26:76-83, 2002.
Southern, *J. Mol. Biol.*, 98:503-517, 1975.
Szczepek et al., *Nat. Biotechnol.*, 25:786-793, 2007.
Temin, In: *Gene Transfer*, Kucherlapati (Ed.), NY, Plenum Press, 149-188, 1986.
Thibodeau et al., *Biotechniques,* 36:410-415, 2004.
Thibodeau-Beganny and Joung, *Methods in Molec. Biol.*, 408:317-334, 2007.
Urnov et al., *Nature,* 435:646-651, 2005.
Welsh et al., In: *The Metabolic and Molecular Basis of Inherited Disease*, Vogelstein (Ed.), McGraw-Hill, Inc., NY, 5121-5189, 2001.
Wolfe et al., *J. Mol. Biol.*, 285:1917-1934, 1999.
Wong et al., *Gene,* 10:87-94, 1980.
Wright et al., *Plant J.*, 44:693-705, 2005.
Wright et al., *Nat. Protoc.*, 1:1637-1652, 2006.

The invention claimed is:

1. A method of promoting recombination within a CTFR gene in a human cell comprising contacting said cell with a first zinc three-finger binding domain that targets a nucleotide sequence TTAGAAGTG (SEQ ID NO:132) and a second zinc three-finger binding domain that targets a nucleotide sequence TTATGGGAG (SEQ ID NO:133), wherein each of said first and second zinc three-finger binding domains are linked to a non-specific nuclease, wherein said first zinc three-finger binding domain comprises a sequence selected from SEQ ID NOS:3-5, 6-8, 9-11, 12-14, 15-17, 18-20, 21-23, 24-26, 27-29, 30-32, 33-35 and 36-38 for TTA-GAAGTG (SEQ ID NO:132) and said second zinc three-finger binding domain comprises a sequence selected from the group consisting of SEQ ID NOS:39-41, 42-44, 45-47, 48-50, 51-53, 54-56, 57-59, 60-62, 63-65, 66-68, 69-71, 72-74, 75-77, 78-80, 81-83, 84-86, 87-89, 90-92, 91-93, 94-96, 97-99, 100-102, 103-105, 106-108, and 109-111 for TTATGGGAG (SEQ ID NO:133).

2. The method of claim 1, wherein said human cell is a lung epithelial cell, and intestinal epithelial cell, a biliary duct epithelial cell, a gall bladder epithelial cell or pancreatic epithelial cell.

3. The method of claim 2, wherein said epithelial lung cell or pancreatic cell comprises a CFTR gene with a ΔF508 mutation.

4. The method of claim 3, wherein said epithelial lung cell or pancreatic epithelial cell is located in a living human subject.

5. The method of claim 4, wherein contacting comprises administering said first and second zinc three-finger binding domains to lung or pancreatic tissue of said subject.

6. The method of claim 5, wherein administration to lung tissue comprises inhalation or topical instillation.

7. The method of claim 5, wherein administration to pancreatic tissue comprises injection.

8. The method of claim 1, wherein contacting comprises administering to said subject an expression vector comprising a first nucleic acid segment encoding a first zinc three-finger binding domain that targets TTAGAAGTG (SEQ ID NO: 132) and a second nucleic acid segment encoding a second zinc three-finger binding domain that targets TTATGGGAG (SEQ ID NO: 133), said nucleic acids under the control of one or more promoters operable in a eukaryotic cell.

9. The method of claim 8, wherein said vector is a viral vector.

10. The method of claim 9, wherein said viral vector is an adenoviral vector, an adeno-associated viral vector, a pox viral vector, a herpes viral vector, a retroviral vector, a lentiviral vector.

11. The method of claim 10, wherein the lentiviral vector is an integrase-deficient vector.

12. The method of claim of claim 8, wherein each of said nucleic acid segments is under the control of a separate promoter active in said eukaryotic cell.

13. The method of claim 8, wherein both of said nucleic acid segments are under the control of the same promoter.

14. The method of claim 12, wherein said nucleic acid segments are separated by a transcription termination signal.

15. The method of claim 13, wherein said nucleic acid segments are separated by an internal ribosome entry site and/or a picornavirus T2A sequence.

* * * * *

UNITED STATES PATENT AND TRADEMARK OFFICE
CERTIFICATE OF CORRECTION

PATENT NO.          : 8,846,578 B2                                        Page 1 of 1
APPLICATION NO.     : 12/905824
DATED               : September 30, 2014
INVENTOR(S)         : Paul McCray et al.

It is certified that error appears in the above-identified patent and that said Letters Patent is hereby corrected as shown below:

On the title page, item (56) References Cited - Other Publications, delete the 15th reference on page 2 "Porteus and Carroll, "Gene targeting using zinc finger nucleases," *Nat. Biotechonl.*, 23:967-673, 2005." and replace with --Porteus and Carroll, "Gene targeting using zinc finger nucleases," *Nat. Biotechnol.*, 23:967-973, 2005.-- therefor.

In the Claims

In claim 1, column 103, line 28, delete "CTFR" and replace with --CFTR-- therefor.

In claim 2, column 103, line 47, delete "and" and replace with --an-- therefor.

Signed and Sealed this
Twenty-seventh Day of January, 2015

Michelle K. Lee
*Deputy Director of the United States Patent and Trademark Office*